(12) United States Patent
Wisdom et al.

(10) Patent No.: US 8,455,471 B2
(45) Date of Patent: Jun. 4, 2013

(54) COMPOSITIONS OF CHK1 INHIBITORS AND CYCLODEXTRIN

(75) Inventors: Wendy A. Wisdom, Edmonds, WA (US); Anita A. Colvin, North Bend, WA (US); Sandy Koppenol, Lake Forest Park, WA (US)

(73) Assignee: ICOS Corporation, Bothell, WA (US)

(*) Notice: Subject to any disclaimer, the term of this patent is extended or adjusted under 35 U.S.C. 154(b) by 639 days.

(21) Appl. No.: 12/442,529

(22) PCT Filed: Oct. 2, 2007

(86) PCT No.: PCT/US2007/080150
§ 371 (c)(1),
(2), (4) Date: Mar. 24, 2009

(87) PCT Pub. No.: WO2008/067027
PCT Pub. Date: Jun. 5, 2008

(65) Prior Publication Data
US 2010/0022512 A1    Jan. 28, 2010

Related U.S. Application Data

(60) Provisional application No. 60/853,056, filed on Oct. 20, 2006.

(51) Int. Cl.
*A61K 31/33* (2006.01)

(52) U.S. Cl.
USPC ........................................ 514/183

(58) Field of Classification Search
USPC ........................................ 514/183
See application file for complete search history.

(56) References Cited

U.S. PATENT DOCUMENTS

| 4,672,112 A | 6/1987 | Matolcsy |
| 5,376,645 A | 12/1994 | Stella |
| 6,046,177 A | 4/2000 | Stella |
| 7,067,506 B2 | 6/2006 | Keegan et al. |

FOREIGN PATENT DOCUMENTS

| CN | 1813739 | 9/2006 |
| EP | 0717638 | 3/2002 |
| WO | WO 91/11200 | 8/1991 |
| WO | WO 0207772 | 1/2002 |
| WO | WO 03015828 | 2/2003 |
| WO | WO 2005/027907 A1 * | 3/2005 |
| WO | WO 2006105262 | 10/2006 |

OTHER PUBLICATIONS

Han 'Advances in the Characterization of Pharmaceutical Hydrates' Trends in Bio/Pharmaceutical Industry, vol. 3, p. 25-29, 2006.*
Stella et al 'Prodrugs: Challenges and Rewards, Part 1' Biotechnology: Pharmaceutical Aspects, p. 24, 2007.*
Vippagunta et al 'Crystalline Solids' Advanced Drug Delivery Reviews, vol. 48, p. 3-26, 2001.*
Loftsson Thorsteinn et al: "Cyclodextrins in Drug Delivery" Expert Opinion on Drug Delivery, Ashley Publications, vol. 2, No. 2, Mar. 1, 2005, pp. 335-351.
Cooper et al., Org. Biomol. Chem., 3:1863 (2005).
Liu et al., J. Org. Chem., 69:173 (2004).
Rekharsky et al., J. Am. Chem. Soc., 124:12361 (2002).
Wang et al., J. Org. Chem. 70:8703 (2005).

* cited by examiner

*Primary Examiner* — Brandon Fetterolf
*Assistant Examiner* — Christopher R Stone
(74) *Attorney, Agent, or Firm* — Danica Hostettler; Elizabeth A. McGraw

(57) ABSTRACT

Compositions containing at least one Chk1 inhibitor and at lease one cyclodextrin are disclosed. Also disclosed are methods of treating a cancer or potentiating a cancer treatment with a composition comprising at least one Chk1 inhibitor and at least one cyclodextrin.

7 Claims, No Drawings

US 8,455,471 B2

COMPOSITIONS OF CHK1 INHIBITORS AND CYCLODEXTRIN

This application is a national stage entry under 35 U.S.C. §371 of PCT/US2007/080150, filed Oct. 2, 2007, which claims benefit of Provisional Application No. 60/853,056, filed Oct. 20, 2006.

FIELD OF THE INVENTION

The present invention relates to compositions comprising a Chk1 inhibitor. More particularly, the present invention relates to compositions comprising (a) a Chk1 inhibitor and (b) a cyclodextrin; methods of treating a cancer and/or potentiating a cancer treatment using these compositions; and methods of treating non-cancerous disorders involving aberrantly proliferating cells using these compositions.

BACKGROUND

The biochemical, physiological, and clinical effects of Chk1 inhibitors suggest their utility in a variety of disease states in which modulation of Chk1 and control of the cell cycle is desired. See Sanchez et al., *Science*, 277:1497 (1997); Chen et al., *Oncogene*, 18:249 (1999); Lui et al., *Genes Dev.*, 14:1448 (2000); Tenzer et al., *Curr. Med. Chem. Anti-Cancer Agents*, 3:35 (2003); and Mack et al., *Cancer Chemother. Pharmacol.*, 51(4):337 (2003). Such disease states include cancers and diseases involving non-cancerous, aberrantly proliferating cells, such as psoriasis, renal disease, and systemic lupus erythematosus.

Chk1 inhibitors have been disclosed, including aryl- and heteroaryl-substituted urea compounds; methylxanthines and related compounds; ureidothiophenes; N-pyrrolopyridinyl carboxamides; antisense Chk1 oligonucleotides; Chk1 receptor antagonists; heteroaromatic carboxamide derivatives; aminothiophenes; (indazolyl)benzimidazoles; benzimidazole quinolinones; heterocyclic-hydroxyimino-fluorenes; scytoneman derivatives, such as scytonemin; heteroarylbenzamides; indazoles; indolacarbazoles; chromane derivatives; paullones; indenopyrazoles; flavones; peptide derivatives of peptide loop of serine threonine kinases; oxindoles; diazepinoindolones; pyrimidines; urea compounds; pyrrolocarbazoles; benzofuroisoindoles; and azacyclopentafluorenes.

The therapeutic benefit of Chk1 inhibitors can be achieved through administration to a subject in need thereof, but the routes of the administration and the associated vehicles used have not been sufficiently investigated. The poor solubility of many Chk1 inhibitors has impeded the development of pharmaceutically acceptable means of administering these compounds. Additionally, some Chk1 inhibitors have been shown exhibit side effects such as hemolysis in animal models. Moreover, some Chk1 inhibitors are unstable in certain formulations and can degrade to inactive, or more concerning, toxic derivatives, prior to or during administration, thereby decreasing the effectiveness of the Chk1 inhibitor for its intended purpose.

Thus, there remains a need for compositions containing Chk1 inhibitors that provide sufficient solubility and stability, while minimizing undesired side effects. The present disclosure addresses such concerns.

SUMMARY

The present invention provides compositions comprising (a) at least one Chk1 inhibitor and (b) at least one cyclodextrin; methods of treating a cancer and/or potentiating a cancer treatment using these compositions; and methods of treating diseases involving non-cancerous, aberrantly proliferating cells using these compositions.

Therefore, one aspect of the invention provides compositions comprising (a) at least one Chk1 inhibitor and (b) at least one cyclodextrin. In various embodiments, the Chk1 inhibitors can be disubstituted urea compounds, wherein each nitrogen (N and N') of the urea moiety is monosubstituted and each substituent is optionally substituted and selected from the group consisting of aryl, heteroaryl, cycloalkyl, heterocycloalkyl, and $C_{1-6}$ alkyl substituted with a heteroaryl or aryl moiety. Specific disubstituted urea compounds include those disclosed in U.S. Pat. No. 7,067,506; WO 06/012308; WO 06/014359; WO 06/021002; International Patent Application No. PCT/US06/11584; U.S. Provisional Patent Application No. 60/818,008, filed Jun. 30, 2006; U.S. Patent Publication No. 2004/0014765; WO 03/101444; U.S. Pat. No. 7,056,925; WO 04/014876; WO 06/0725891; WO 05/215556; Fan et al., *Cancer Res.* 55:1649 (1995); WO 03/029241; WO 03/028731; WO 03/028724; WO 01/57206; U.S. Pat. No. 6,211,164; WO 04/004785; WO 00/16781; WO 03/037886; WO 03/029242; WO 03/004488; U.S. Patent Publication No. 2004/0092535; WO 04/018419; WO 02/16326; U.S. Pat. No. 6,495,586; WO 01/53274; WO 01/53268; Tenzer et al., *Curr. Med. Chem. Anti-Cancer Agents,* 3:35 (2003); WO 02/070515; Schultz, et al., *J. Med. Chem.*, 42:2909 (1999); WO 99/17769; Sedlacek et al., *Int. J. Oncol.* 9:1143 (1996); WO 98/53050; WO 03/051838; WO 04/063198; WO 04/048343; WO 03/091255; WO 06/074281; WO 02/100356; WO 04/002481; WO 03/093297; WO 05/103036; WO 05/16909; WO 04/97426; WO 04/87707; WO 05/9435); WO 06/74281; and WO 06/74207, each incorporated herein by reference.

In various embodiments, the cyclodextrins are α-cyclodextrins, β-cyclodextrins, γ-cyclodextrins, and/or δ-cyclodextrins. In some embodiments, the cyclodextrins are modified cyclodextrins. Specific modifications include, but are not limited to, hydroxyalkyl ethers and sulfoalkyl ethers. In some embodiments, the modified cyclodextrins are sulfobutylether-1-β-cyclodextrin, sulfobutylether-4-β-cyclodextrin, sulfobutylether-7-β-cyclodextrin, and/or hydroxypropylether β-cyclodextrin. In one embodiment, the modified cyclodextrin comprises sulfobutylether-7-β-cyclodextrin.

In some embodiments, the compositions disclosed herein can have a mole ratio of Chk1 inhibitor to cyclodextrin of up to the total number of complexation sites available on the cyclodextrin. In other embodiments, the compositions disclosed herein can have a mole ratio of Chk1 inhibitor to cyclodextrin greater than the total number of complexation sites available on the cyclodextrin. The structure of the cyclodextrin will influence the maximum number of sites for complexation. In various embodiments, the mole ratio of Chk1 inhibitor to cyclodextrin is up to about 9:1. In other embodiments, the mole ratio of Chk1 inhibitor to cyclodextrin is up to about 5:1. In still other embodiments, the mole ratio of Chk1 inhibitor to cyclodextrin is at least about 1:2.

The present compositions can be administered to a subject in need thereof via a variety of routes. In specific embodiments, the route of administration is dermal, subcutaneous, intramuscular, intra-articular, pulmonal, buccal, sublingual, nasal, via inhalation, percutaneous, vaginal, oral, parenteral, rectal, intravenous, topical, intradermal, ophthalmic, and/or intraperitoneal.

The disclosed compositions can further include a pH adjusting agent and/or a pharmaceutically acceptable excipient. Specific pH adjusting agents include, but are not limited to, buffers, acids, and bases. In some embodiments, the pH of the composition, when in an aqueous solution, is from about 2 to about 8. In various embodiments, the pH of the composition, when in an aqueous solution, is from about 3 to about 5. In some embodiments, the pH of the solution is from about 4 to about 4.7.

In various embodiments, the compositions of the invention are substantially anhydrous. In some embodiments, the amount of water in the compositions is less than about 5%, based upon the total weight of the composition. In various embodiments, the amount of water is less than about 2%. In still other embodiments, the amount of water is less than about 1%. In some embodiments, the compositions are lyophilized and/or spray-dried.

In other embodiments, the present compositions also are in liquid form, using, e.g., an aqueous and/or an alcohol or other organic solvent solution. Regardless of the form of the compositions, for routes of administration requiring a liquid formulation, solid forms of the composition are typically reconstituted, dissolved, or diluted in a suitable liquid carrier prior to administration to an individual.

The present compositions also can include one or more additional active ingredients as determined by, e.g., a medical professional. Nonlimiting examples of contemplated additional active ingredients include an antiemetic agent, a cytoprotective agent, an antinecrotic agent, an imaging agent, an anticancer agent, and an agent suitable for treating non-cancerous indications involving aberrantly proliferating cells. In some embodiments, the anticancer agent is a Chk1 activator.

Another aspect of the invention provides methods of potentiating a cancer treatment or treating a cancer by administering to an individual in need thereof a therapeutically effective amount of an anticancer agent and a therapeutically effective amount of a composition disclosed herein. In some embodiments, the anticancer agent and the composition disclosed herein are administered sequentially, while in other embodiments, the anticancer agent and the composition are administered simultaneously. In specific embodiments, the anticancer agent is administered prior to the compositions disclosed herein.

In some embodiments, when an anticancer agent and a Chk1 inhibitor are administered to an individual, either from the same formulation or in a sequential or simultaneous manner from different formulations, the amount of administered anticancer agent can be reduced compared to the amount of the same anticancer agent that would be required in the absence of the Chk1 inhibitor to achieve a comparable therapeutic result. Therefore, in some embodiments, the therapeutically effective amount of the anticancer agent, when based upon simultaneous or sequential use of a Chk1 inhibitor, is less than a therapeutically effective amount of the same anticancer agent in the absence of administration of the Chk1 inhibitor.

In some embodiments, the anticancer agent is a Chk1 activator. In various embodiments, the anticancer agent is a chemotherapeutic, a radiotherapeutic, or both. In specific embodiments, the chemotherapeutic agent can be an alkylating agent, an antimetabolite, a hormone or antagonist thereof, an antibody, or mixtures thereof. The chemotherapeutic agent can be, for example, pemetrexed, gemcitabine, cisplatin, methotrexate, trimetrexate, or mixtures thereof. Examples of alkylating agents include nitrogen mustards, such as mechlorethamine, cyclophosphamide, ifosfamide, melphalan, or chlorambucil. Other examples of chemotherapeutics include nitrosoureas, such as carmustine, lomustine, or semustine; ethylenimines and/or methyl-melamines, such as triethylenemelamine, triethylene thiophosphoramide, or hexamethylmelamine; alkyl sulfonates, such as busulfan; and triazines, such as dacarbazine. Other anticancer agents include antimetabolites, such as folic acid analogs (e.g., methotrexate, trimetrexate, or pemetrexed); pyrimidine analogs (e.g., 5-fluorouracil, fluorodeoxyuridine, gemcitabine, cytosine arabinoside, 5-azacytidine, or 2,2'-difluorodeoxycytidine); purine analogs (e.g., 6-mercaptopurine, 6-thioguanine, azathioprine, 2'-deoxycoformycin, erythrohydroxynonyladenine, a fludarabine salt, or 2-chlorodeoxyadenosine); and/or type I topoisomerase inhibitors (e.g., camptothecin, topotecan, or irinotecan). In some embodiments, the anticancer agent can be derived from a natural product, such as epipodophylotoxins (e.g., etoposide or teniposide); and/or vinca alkaloids (e.g., vinblastine, vincristine, or vinorelbine). In certain embodiments, the anticancer agent can be an antibiotic, such as actinomycin D, doxorubicin, or bleomycin. In various embodiments, the anticancer agent can be a radiosensitizer, such as 5-bromodeoxyuridine, 5-iododeoxyuridine, or bromodeoxycytidine. In some embodiments, the anticancer agent can be a platinum coordination complex, such as cisplatin, carboplatin, or oxaliplatin. The anticancer agent can be hydroxyurea and/or a methylhydrazine derivative, such as N-methylhydrazine or procarbazine. In some embodiments, radiotherapeutic agent can be gamma-radiation, X-ray radiation, ultraviolet radiation, visible radiation, infrared radiation, and microwave radiation.

The compositions and methods disclosed herein are useful in treating and/or ameliorating conditions involving aberrantly proliferating cells, including cancer. In specific embodiments, the compositions and methods disclosed herein are useful for treating cancers, such as non-small cell lung cancer, myxoid and round cell carcinomas, locally advanced tumors, metastatic cancer, Ewing's sarcoma, cancer metastases, lymphatic metastases, squamous cell carcinomas, esophageal squamous cell carcinomas, oral carcinomas, multiple myelomas, acute lymphocytic leukemias, acute nonlymphocytic leukemias, chronic lymphocytic leukemias, chronic myelocytic leukemias, hairy cell leukemias, effusion lymphomas (body cavity-based lymphomas), thymic lymphoma lung cancers, small cell carcinomas of the lung, cutaneous T-cell lymphomas, Hodgkin's lymphomas, non-Hodgkin's lymphomas, cancers of the adrenal cortex, ACTH-producing tumors, nonsmall cell lung cancers, breast cancers, small cell carcinomas, ductal carcinomas, stomach cancers, colon cancers, colorectal cancers, polyps associated with colorectal neoplasias, pancreatic cancers, liver cancers, bladder cancers, primary superficial bladder tumors, invasive transitional cell carcinomas of the bladder, muscle-invasive bladder cancers, prostate cancers, ovarian carcinomas, primary peritoneal epithelial neoplasms, cervical carcinomas, uterine endometrial cancers, vaginal cancers, cancers of the vulva, uterine cancers and solid tumors in the ovarian follicle, testicular cancers, penile cancers, renal cell carcinomas, intrinsic brain tumors, neuroblastomas, astrocytic brain tumors, gliomas, metastatic tumor cell invasions in the central nervous system, osteomas and osteosarcomas, malignant melanomas, tumor progressions of human skin keratinocytes, squamous cell cancers, thyroid cancers, retinoblastomas, neuroblastomas, peritoneal effusions, malignant pleural effusions, mesotheliomas, Wilms's tumors, gall bladder cancers, trophoblastic neoplasms, hemangiopericytomas, Kaposi's sarcomas or other cancers treatable with chemotherapy agents or inhibitors of cell cycle checkpoint proteins. In various embodiments, the cancer is a colorectal cancer, a head and neck cancer, a pancreatic cancer, a breast cancer, a gastric cancer, a bladder cancer, a vulvar cancer, a leukemia, a lymphoma, a melanoma, a renal cell carcinoma, an ovarian cancer, a brain tumor, an osteosarcoma, or a lung carcinoma.

Another aspect of the invention provides methods of treating non-cancerous disorders involving aberrantly proliferating cells via administration of compositions disclosed herein. Non-cancerous disorders include, but are not limited to, atherosclerosis, restenosis, vasculitis, nephritis, retinopathy, renal disease, proliferative skin disorders, psoriasis, keloid scarring, actinic keratosis, Stevens-Johnson Syndrome, rheumatoid arthritis, systemic-onset juvenile chronic arthritis, osteoporosis, systemic lupus erythematosus, hyperproliferative diseases of the eye, proliferative vitreoretinopathy (PVR), hemangio-proliferative diseases, ichthyosis, and papillomas.

Yet another aspect of the invention provides use of a composition comprising at least one disubstituted urea compound and at least one cyclodextrin for the manufacture of a medicament for the treatment of a disorder involving aberrantly proliferating cells. In some embodiments, the disorder comprises a cancer. In other embodiments, the disorder comprises non-cancerous aberrantly proliferating cells.

Another aspect of the invention provides a kit comprising a first container comprising a composition as disclosed herein and instructions for administering the composition to a subject in need thereof. In some embodiments, the kit further comprises an anticancer agent. In some specific embodiments, the anticancer agent is in the first container, while in other embodiments, the anticancer agent is in a second container.

DETAILED DESCRIPTION

Disclosed herein are compositions comprising (a) a Chk1 inhibitor and (b) a cyclodextrin. More particularly, disclosed herein are compositions comprising at least one Chk1 inhibitor and at least one cyclodextrin, and methods of treating a cancer or potentiating a cancer treatment via administration of these compositions to an individual in need thereof. Further disclosed herein are methods of treating diseases involving non-cancerous, aberrantly proliferating cells via administration of a present composition to an individual in need thereof.

Chk1 inhibitors have been found to be effective in cancer treatments protocols when tested in animals, but have exhibited undesirable side effects and/or low solubility.

It has been discovered that, in various embodiments, a composition comprising at least one Chk1 inhibitor and at least one cyclodextrin increases solubility of the Chk1 inhibitor in water, and/or decreases toxicity of the Chk1 inhibitor toward untargeted cells (e.g., endothelial cells), and/or enhances the stability of the Chk1 inhibitor prior to administration and/or upon administration to an individual in need thereof.

Chk1 Inhibitors

"Chk1 inhibitor" means any agent, whether now known or after-discovered, whether naturally occurring, isolated from nature, or man-made, that is capable of at least partially abrogating cell cycle checkpoint activity of Chk1. Such agents can be alternatively referred to as "capable of inhibiting Chk1." Such agents include, but are not limited to, small molecule compounds, biologics, and antisense agents. One specific example of a class of Chk1 inhibitors is a disubstituted urea compound, wherein each nitrogen of the urea compound is substituted with one or more aryl and/or heteroaryl moieties.

If more than one Chk1 inhibitor is used, the Chk1 inhibitors can be co-administered or administered at separate times as determined by the attending physician or laboratory technician. One way to determine Chk1 inhibitor activity is by assessing Chk1 activity, both in the presence and absence of the suspected Chk1 inhibitor. Such assessments are readily apparent to those of skill in the art. See, e.g., U.S. Pat. No. 7,067,506, incorporated herein by reference.

Compounds useful in the present invention as Chk1 inhibitors include, but are not limited to, disubstituted ureas. Disubstituted ureas, as used herein, refers to urea compounds having one substituent at each nitrogen (N and N') wherein each substituent is optionally substituted and selected from the group consisting of aryl, heteroaryl, cycloalkyl, heterocycloalkyl, and $C_{1-6}$ alkyl substituted with a heteroaryl or aryl moiety. In some embodiments, the urea compounds comprise two aryl substituents, while in other embodiments, the urea compounds comprise one aryl and one heteroaryl substituent, and in still other embodiment, the urea compounds comprise two heteroaryl substituents. Specific examples of disubstituted ureas include, but are not limited to, those described or claimed in the following publications, the entire disclosures of which are incorporated herein by reference:

aryl and heteroaryl substituted urea compounds described in any one of the following patents and patent applications: U.S. Pat. No. 7,067,506; WO 2002/070494; WO 06/012308; WO 06/014359; WO 06/021002; International Patent Application No. PCT/US06/11584; and U.S. Provisional Patent Application No. 60/818,008, filed Jun. 30, 2006;

diaryl urea compounds described in U.S. Patent Publication No. 2004/0014765;

diaryl urea compounds described in WO 03/101444;

diaryl urea compounds described in U.S. Pat. No. 7,056,925 and WO 04/014876;

disubstituted urea compounds described in WO 06/0725891; and macrocyclic disubstituted urea compounds described in WO 05/215556.

Other compounds useful as Chk1 inhibitors include methylxanthines and related compounds (Fan et al., *Cancer Res.* 55:1649 (1995)); ureidothiophenes (WO 03/029241 and WO 03/028731); N-pyrrolopyridinyl carboxamides (WO 03/028724); antisense Chk1 oligonucleotides (WO 01/57206 and U.S. Pat. No. 6,211,164); genes which modulate Chk1 (WO 04/004785); Chk1 receptor antagonists (WO 00/16781); heteroaromatic carboxamide derivatives (WO 03/037886); aminothiophenes (WO 03/029242); (indazolyl) benzimidazoles (WO 03/004488); benzimidazole quinolinones (U.S. Patent Publication No. 2004/0092535 and WO 04/018419); heterocyclic-hydroxyimino-fluorenes (WO 02/16326); scytoneman skeleton containing derivatives (scytonemin) (U.S. Pat. No. 6,495,586); heteroarylbenzamides (WO 01/53274); indazole compounds (WO 01/53268); indolacarbazoles (Tenzer et al., supra); chromane derivatives (WO 02/070515); paullones (Schultz, et al., *J. Med. Chem.,* 42:2909 (1999)); indenopyrazoles (WO 99/17769); flavones (Sedlacek et al., *Int. J. Oncol.* 9:1143 (1996)); peptide derivatives of peptide loop of serine threonine kinases (WO 98/53050); oxindoles (WO 03/051838); diazepinoindolones (WO 04/063198); pyrimidines (WO 04/048343); pyrrolocarbazoles, benzofuroisoindoles, and azacyclopentafluorenes (WO 03/091255); fused pyrazoles (WO 06/074281); naphthyridines (WO 02/100356); aryl carbonyl derivatives (WO 04/002481); substituted pyridine derivatives (WO 03/093297); pyrimidin4-yl-1H-indazol-5-yl-amines (WO 05/103036); substituted thiophenes (WO 05/16909); substituted pyran derivatives (WO 04/97426), pyrazolopyrimidine derivatives (WO 04/87707); aminopyrazole derivatives (WO 05/9435); and fused pyrazoles (WO 06/74281 and WO 06/74207), each incorporated herein by reference.

Specific classes of Cbk1 inhibitors include, but are not limited to, the classes set forth below.

I. Diarylurea Compounds Described in WO 02/070494 i) A Compound Having a Formula (I):

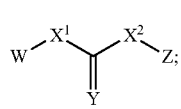

wherein $X^1$ is null, —O—, —S—, —CH$_2$—, or —N(R$^1$)—; $X^2$ is —O—, —S—, or —N(R$^1$)—; Y is O or S; or =Y represents two hydrogen atoms attached to a common carbon atom; W is selected from the group consisting of heteroaryl, aryl, heterocycloalkyl, cycloalkyl, and C$_{1-6}$ alkyl substituted with a heteroaryl or aryl group;

Z is selected from the group consisting of hydro, aryl, and heteroaryl; wherein said aryl groups of W and Z are independently optionally substituted with one to four substituents represented by R$^2$, said heteroaryl groups of W and Z are independently optionally substituted with one to four substituents represented by R$^5$, and said heterocycloalkyl and cycloalkyl groups of W are independently optionally substituted with one to two substituents represented by R$^6$;

R$^1$ is selected from the group consisting of hydro, C$_{1-6}$alkyl, C$_{2-6}$alkenyl, C$_{2-6}$alkynyl, and aryl;

each R$^2$ is independently selected from the group consisting of halo, optionally substituted C$_{1-6}$alkyl, C$_{2-6}$alkenyl, OCF$_3$, NO$_2$, CN, N(R$^3$)$_2$, OR$^3$, CO$_2$R$^3$, C(O)N(R$^3$)$_2$, C(O)R$^3$, N(R$^1$)COR$^3$, N(R$^1$)C(O)OR$^3$, N(R$^3$)C(O)OR$^3$, N(R$^3$)C(O)C$_{1-3}$alkyleneC(O)R$^3$, N(R$^3$)C(O)C$_{1-3}$alkyleneC(O)OR$^3$, N(R$^3$)C(O)C$_{1-3}$alkyleneOR$^3$, N(R$^3$)C(O)C$_{1-3}$ alkyleneNHC(O)OR$^3$, N(R$^3$)C(O)C$_{1-3}$alkyleneSO$_2$NR$^3$, C$_{1-3}$alkyleneOR$^3$, and SR$^3$;

each R$^3$ is independently selected from the group consisting of hydro, C$_{1-6}$alkyl, C$_{2-6}$alkenyl, cycloalkyl, aryl, heteroaryl, SO$_2$R$^4$, C$_{1-6}$alkyl substituted with one or more of halo, hydroxy, aryl, heteroaryl, heterocycloalkyl, N(R$^4$)$_2$, and SO$_2$R$^4$, C$_{1-3}$alkylenearyl, C$_{1-3}$alkyleneheteroaryl, C$_{1-3}$alkyleneC$_{3-8}$heterocycloalkyl, C$_{1-3}$alkyleneSO$_2$aryl, optionally substituted C$_{1-3}$alkyleneN(R$^4$)$_2$, OCF$_3$, C$_{1-3}$alkyleneN(R$^4$)$_3{}^+$, C$_{3-8}$heterocycloalkyl, and CH(C$_{1-3}$alkyleneN(R$^4$)$_2$)$_2$, or two R$^3$ groups are taken together to form an optionally substituted 3- to 6-membered aliphatic ring;

each R$^4$ is independently selected from the group consisting of hydro, C$_{1-6}$alkyl, cycloalkyl, aryl, heteroaryl, C$_{1-3}$alkylenearyl, and SO$_2$C$_{1-6}$alkyl, or two R$^4$ groups are taken together to form an optionally substituted 3- to 6-membered ring;

each R$^5$ is independently selected from the group consisting of C$_{1-6}$alkyl, aryl, N(R$^3$)$_2$, OR$^3$, halo, N$_3$, CN, C$_{1-3}$alkylenearyl, C$_{1-3}$alkyleneN(R$^3$)$_2$, C(O)R$^3$, and

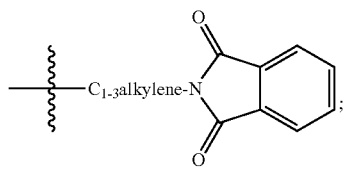

each R$^6$ is independently selected from the group consisting of halo and C$_{1-6}$alkyl; and pharmaceutically acceptable salts, prodrugs, or solvates thereof.

ii) A Compound Having a Formula (II)

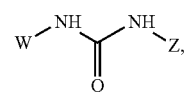

wherein W is selected from the group consisting of heteroaryl, aryl, heterocycloalkyl, cycloalkyl, and C$_{1-6}$ alkyl substituted with a heteroaryl or aryl group;

Z is selected from the group consisting of aryl, and heteroaryl;

wherein said aryl groups of W and Z are independently optionally substituted with one to four substituents represented by R$^2$, said heteroaryl groups of W and Z are independently optionally substituted with one to four substituents represented by R$^5$, and said heterocycloalkyl and cycloalkyl groups of W are independently optionally substituted with one to two substituents represented by R$^6$;

R$^1$ is selected from the group consisting of hydro, C$_{1-6}$alkyl, C$_{2-6}$alkenyl, C$_{2-6}$alkynyl, and aryl;

each R$^2$ is independently selected from the group consisting of halo, optionally substituted C$_{1-6}$alkyl, C$_{2-6}$alkenyl, OCF$_3$, NO$_2$, CN, NC, N(R$^3$)$_2$, OR3, CO$_2$R$^3$, C(O)N(R$^3$)$_2$, C(O)R$^3$, N(R$^1$)COR$^3$, N(R$^1$)C(O)OR$^3$, N(R$^3$)C(O)OR$^3$, N(R$^3$)C(O)C$_{1-3}$alkyleneC(O)R$^3$, N(R$^3$)C(O)C$_{1-3}$alkyleneC(O)OR$^3$, N(R$^3$)C(O)C$_{1-3}$alkyleneOR$^3$, N(R$^3$)C(O)C$_{1-3}$ alkyleneNHC(O)OR$^3$, N(R$^3$)C(O)C$_{1-3}$alkyleneSO$_2$NR$^3$, C$_{1-3}$alkyleneOR$^3$, and SR$^3$;

each R$^3$ is independently selected from the group consisting of hydro, C$_{1-6}$alkyl, C$_{2-6}$alkenyl, cycloalkyl, aryl, heteroaryl, SO$_2$R$^4$, C$_{1-6}$alkyl substituted with one or more of halo, hydroxy, aryl, heteroaryl, heterocycloalkyl, N(R$^4$)$_2$, and SO$_2$R$^4$, C$_{1-3}$alkylenearyl, C$_{1-3}$alkyleneheteroaryl, C$_{1-3}$alkyleneC$_{3-8}$heterocycloalkyl, C$_{1-3}$alkyleneSO$_2$aryl, optionally substituted C$_{1-3}$alkyleneN(R$^4$)$_2$, OCF$_3$, C$_{1-3}$alkyleneN(R$^4$)$_3{}^+$, C$_{3-8}$heterocycloalkyl, and CH(C$_{1-3}$lkyleneN(R$^4$)$_2$)$_2$, or two R$^3$ groups are taken together to form an optionally substituted 3- to 6-membered aliphatic ring;

each R$^4$ is independently selected from the group consisting of hydro, C$_{1-6}$alkyl, cycloalkyl, aryl, heteroaryl, C$_{1-3}$alkylenearyl, and SO$_2$C$_{1-6}$alkyl, or two R$^4$ groups are taken together to form an optionally substituted 3- to 6-membered ring;

R$^5$ is selected from the group consisting of C$_{1-6}$alkyl, aryl, N(R$^3$)$_2$, OR$^3$, halo, N$_3$, CN, C$_{1-3}$alkylenearyl, C$_{1-3}$alkyleneN(R$^3$)$_2$, C(O)R$^3$, and

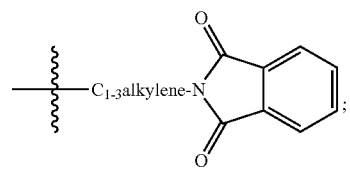

each R$^6$ is independently selected from the group consisting of halo and C$_{1-6}$alkyl; or a pharmaceutically acceptable salt, prodrug, or solvate thereof.

iii) A Compound Having a Formula (III):

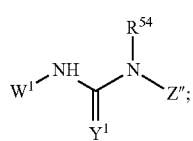

wherein Y¹ is O or S;
W¹ is selected from the group consisting of

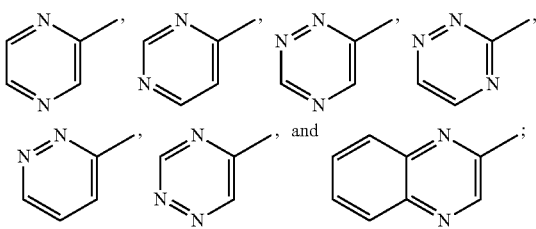

optionally substituted with from one to four substituents selected from the group consisting of $C_{1-6}$alkyl, aryl, N$(R^{51})_2$, OR$^{51}$, N$_3$, CN, C(O)R$^{51}$, $C_{1-3}$alkylenearyl, $C_{1-3}$alkyleneN$(R^{52})_2$, halo, and

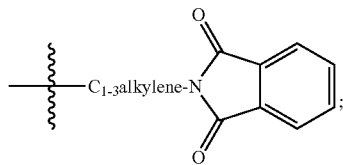

Z" is selected from the group consisting of:

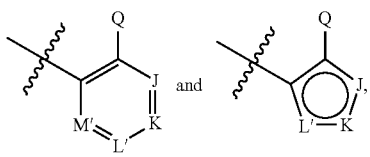

wherein:
Q is selected from the group consisting of hydro, OR$^{51}$, SR$^{51}$, and N$(R^{51})_2$, with the proviso that Q is hydro only when at least one of J, K, L', and M' is N, O, or S;
J, K, and L', independently, are selected from the group consisting of CR$^{53}$, NR$^{53}$, O, and S;
M' is selected from the group consisting of CR$^{55}$, NR$^{55}$, O, and S, with the proviso that Z" is different from a pyridone;
wherein: R$^{51}$, independently, is selected from the group consisting of hydro, $C_{1-6}$alkyl, $C_{2-6}$alkenyl, cycloalkyl, aryl, heteroaryl, SO$_2$R$^{52}$, $C_{1-6}$alkyl substituted with one or more of halo, hydroxy, aryl, heteroaryl, heterocycloalkyl, N$(R^{52})_2$, and SO$_2$R$^{52}$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN$(R^{52})_2$, OCF$_3$, $C_{1-3}$alkyleneN$(R^{52})_3^+$, $C_{3-8}$heterocycloalkyl, and CH$(C_{1-3}$alkyleneN$(R^{52})_2)_2$, or two R$^{51}$ groups are taken together to form an optionally substituted 3- to 6-membered aliphatic ring;

R$^{52}$ is selected from the group consisting of hydro, $C_{1-6}$alkyl, cycloalkyl, aryl, heteroaryl, $C_{1-3}$alkylenearyl, and SO$_2$C$_{1-6}$alkyl, or two R$^{52}$ groups are taken together to form an optionally substituted 3- to 6-membered ring;
R$^{53}$ is independently selected from the group consisting of null, hydro, halo, optionally substituted $C_{1-6}$alkyl, $C_{2-6}$alkenyl, OCF$_3$, NO$_2$, CN, NC, N$(R^{51})_2$, OR$^{51}$, CO$_2$R$^{51}$, C(O)N$(R^{51})_2$, C(O)R$^{51}$, N(R$^{54}$)C(O)R$^{51}$, N(R$^{54}$)C(O)OR$^{51}$, N(R$^{51}$)C(O)OR$^{51}$, N(R$^{51}$)C(O)$C_{1-3}$alkyleneC(O)R$^{51}$, N(R$^{51}$)C(O)$C_{1-3}$alkyleneC(O)OR$^{51}$, N(R$^{51}$)C(O)$C_{1-3}$alkyleneOR$^{51}$, N(R$^{51}$)C(O)$C_{1-3}$alkyleneNHC(O)OR$^{51}$, N(R$^{51}$)C(O)$C_{1-3}$alkyleneSO$_2$NR$^{51}$, CF$_3$, $C_{1-3}$alkyleneN(R$^{52}$)SO$_2$aryl, $C_{1-3}$alkyleneN(R$^{52}$)SO$_2$heteroaryl, $C_{1-3}$alkyleneOC$_{1-3}$alkylenearyl, $C_{1-3}$alkyleneN(R$^{52}$)$C_{1-3}$alkylenearyl, $C_{1-3}$alkyleneN(R$^{52}$)$C_{1-3}$alkyleneheteroaryl, $C_{1-3}$alkyleneN(R$^{52}$)C(O)R$^{52}$, $C_{1-3}$alkyleneN(R$^{52}$)C(O)$C_{1-3}$-alkyenleOR$^{52}$, $C_{1-3}$alkyleneN(R$^{52}$)C(O)aryl, $C_{1-3}$alkylene-N(R$^{52}$)C(O)$C_{1-3}$alkyleneN(R$^{52}$)$_2$, $C_{1-3}$alkyleneN(R$^{52}$)C(O)heteroaryl, $C_{1-3}$alkyleneOR$^{51}$, and SR$^{51}$, wherein R$^{51}$ and R$^{52}$ are as defined above;
R$^{55}$ is selected from the group consisting of null, hydro, optionally substituted $C_{1-6}$alkyl, and halo; and
R$^{54}$ is selected from the group consisting of hydro, $C_{1-6}$alkylC$_{2-6}$alkenyl, $C_{2-6}$alkynyl, and aryl;
provided that when Q' is hydro or OCH$_3$, at least one of R$^{53}$ is different from hydro, CH$_3$, OCH$_3$, and halo;
or a pharmaceutically acceptable salt, prodrug, or solvate thereof.

II. Diarylurea Compounds Described in WO 06/012308
i) A Compound Having a Formula (IV):

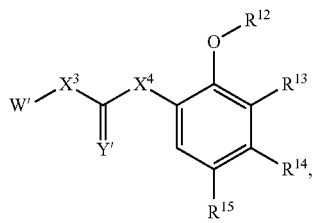

wherein X$^3$ is null, —O—, —S—, —CH$_2$—, or —N(R$^7$)—;
X$^4$ is —O—, —S—, or —N(R$^7$)—;
Y' is O or S; or =Y' represents two hydrogen atoms attached to a common carbon atom;
W' is selected from the group consisting of heteroaryl, aryl, heterocycloalkyl, cycloalkyl, and $C_{1-6}$alkyl substituted with a heteroaryl or aryl group, wherein said aryl group W' is optionally substituted with one to four substituents represented by R$^8$, said heteroaryl group W' is optionally substituted with one to four substituents represented by R$^{11}$, and said heterocycloalkyl and cycloalkyl groups W' are optionally substituted with one or two $C_{1-6}$alkyl substituents;
each R$^7$ is independently selected from the group consisting of hydro, $C_{1-6}$alkyl, $C_{2-6}$alkenyl, $C_{2-6}$alkynyl, and aryl;
each R$^8$ is independently selected from the group consisting of heteroaryl, halo, optionally substituted $C_{1-6}$alkyl, $C_{2-6}$alkenyl, OCF$_3$, NO$_2$, CN, NC, N$(R^9)_2$, OR$^9$, CO$_2$R$^9$, C(O)N$(R^9)_2$, C(O)R$^9$, N(R$^7$)COR$^9$, N(R$^7$)C(O)OR$^9$, N(R$^7$)C(O)$C_{1-6}$alkyleneC(O)R$^9$, N(R$^7$)C(O)$C_{1-6}$alkyleneC(O)OR$^9$, N(R$^7$)C(O)$C_{1-6}$alkyleneOR$^9$, N(R$^7$)C(O)$C_{1-6}$alkyleneNHC(O)OR$^9$, N(R$^7$)C(O)$C_{1-6}$alkyleneSO$_2$NR$^9$, $C_{1-6}$alkyleneOR$^9$, and SR$^9$;

each $R^9$ is independently selected from the group consisting of hydro, $C_{1-6}$alkyl, $C_{2-6}$alkenyl, cycloalkyl, aryl, heteroaryl, $SO_2R^{10}$, halo, $C_{1-6}$alkyl substituted with one or more of halo, hydroxy, aryl, heteroaryl, heterocycloalkyl, $N(R^{10})_2$, and $SO_2R^{10}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{10}$)$_2$, OCF$_3$, $C_{1-6}$alkyleneN(R$^{10}$)$_3^+$, $C_{3-8}$heterocycloalkyl, and CH(C$_{1-6}$alkyleneN(R$^{10}$)$_2$)$_2$, or two $R^9$ groups are taken together to form an optionally substituted 3- to 8-membered aliphatic ring;

each $R^{10}$ is independently selected from the group consisting of hydro, $C_{1-6}$alkyl, cycloalkyl, aryl, heteroaryl, $C_{1-6}$alkylenearyl, and $SO_2C_{1-6}$alkyl, or two $R^{10}$ groups are taken together to form an optionally substituted 3- to 8-membered ring;

each $R^{11}$ is independently selected from the group consisting of $C_{1-6}$alkyl, $C_{2-6}$alkynyl, aryl, heteroaryl, heterocycloalkyl, N(R$^9$)$_2$, N(R$^7$)C(O)R$^9$, N(R$^7$)CO$_2$R$^9$, OR$^9$, halo, N$_3$, CN, $C_{1-6}$alkylenearyl, $C_{1-6}$alkyleneN(R$^9$)$_2$, C(O)R$^9$, C(O)OR$^9$, C(O)N(R$^9$)$_2$, and

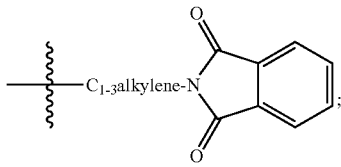

$R^{12}$ is selected from the group consisting of hydro, $C_{1-6}$alkyl, $C_{2-6}$alkenyl, cycloalkyl, heterocycloalkyl, aryl, heteroaryl, $SO_2R^{10}$, $C_{1-6}$alkyl substituted with one or more of halo, hydroxy, aryl, heteroaryl, heterocycloalkyl, N(R$^{10}$)$_2$, and $SO_2R^{10}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{10}$)$_2$, OCF$_3$, $C_{1-6}$alkyleneN(R$^{10}$)$_3^+$, $C_{3-8}$heterocycloalkyl, and CH(C$_{1-6}$alkyleneN(R$^{10}$)$_2$)$_2$;

$R^{13}$ and $R^{14}$, independently, are selected from the group consisting of hydro, OR$^9$, $C_{1-6}$alkyl, halo, N(R$^9$)$_2$, C(O)N(R$^9$)$_2$, $C_{1-3}$alkylenearyl, CN, NO$_2$, C(O)OR$^{17}$, C(O)R$^{17}$, and SR$^{17}$;

$R^{15}$ is —C≡C—R$^{16}$ or —CF$_3$, or an $R^{14}$ and an $R^{15}$ group are taken together with the carbons to which they are attached to form a 5- or 6-membered carbocyclic aliphatic or aromatic ring system optionally containing one to three heteroatoms selected from the group consisting of O, NR$^{10}$, and S;

$R^{16}$ is selected from the group consisting of hydro, $C_{1-6}$alkyl, aryl, $C_{1-6}$alkylenearyl, heteroaryl, and $C_{1-6}$alkyleneheteroaryl;

each $R^{17}$ is independently selected from the group consisting of hydro, $C_{1-6}$alkyl, $C_{2-6}$alkenyl, aryl, $C_{1-3}$alkylenearyl, $C_{3-8}$cycloalkyl, and $C_{1-3}$alkyleneC$_{3-8}$cycloalkyl;

or a pharmaceutically acceptable salt, or prodrug, or solvate thereof.

ii) A Compound Having a Formula (V)

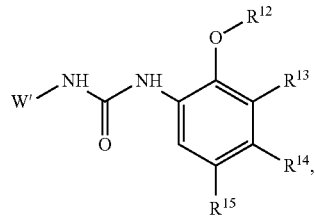

(V)

wherein W' is selected from the group consisting of heteroaryl, aryl, heterocycloalkyl, cycloalkyl, and $C_{1-6}$alkyl substituted with a heteroaryl or aryl group, wherein said aryl group W' is optionally substituted with one to four substituents represented by $R^8$, said heteroaryl group W' is optionally substituted with one to four substituents represented by $R^{11}$, and said heterocycloalkyl and cycloalkyl groups W' are optionally substituted with one or two $C_{1-6}$alkyl substituents;

each $R^7$ is independently selected from the group consisting of hydro, $C_{1-6}$alkyl, $C_{2-6}$alkenyl, $C_{2-6}$alkynyl, and aryl;

each $R^8$ is independently selected from the group consisting of heteroaryl, halo, optionally substituted $C_{1-6}$alkyl, $C_{2-6}$alkenyl, OCF$_3$, NO$_2$, CN, NC, N(R$^9$)$_2$, OR$^9$, CO$_2$R$^9$, C(O)N(R$^9$)$_2$, C(O)R$^9$, N(R$^7$)COR$^9$, N(R$^7$)C(O)OR$^9$, N(R$^7$)C(O)C$_{1-6}$alkyleneC(O)R$^9$, N(R$^7$)C(O)C$_{1-6}$alkyleneC(O)OR$^9$, N(R$^7$)C(O)C$_{1-6}$alkyleneOR$^9$, N(R$^7$)C(O)C$_{1-6}$alkyleneNHC(O)OR$^9$, N(R$^7$)C(O)C$_{1-6}$alkyleneSO$_2$NR$^9$, $C_{1-6}$alkyleneOR$^9$, and SR$^9$;

each $R^9$ is independently selected from the group consisting of hydro, $C_{1-6}$alkyl, $C_{2-6}$alkenyl, cycloalkyl, aryl, heteroaryl, $SO_2R^{10}$, halo, $C_{1-6}$alkyl substituted with one or more of halo, hydroxy, aryl, heteroaryl, heterocycloalkyl, N(R$^{10}$)$_2$, and $SO_2R^{10}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{10}$)$_2$, OCF$_3$, $C_{1-6}$alkyleneN(R$^{10}$)$_3^+$, $C_{3-8}$heterocycloalkyl, and CH(C$_{1-6}$alkyleneN(R$^{10}$)$_2$)$_2$, or two $R^9$ groups are taken together to form an optionally substituted 3- to 8-membered aliphatic ring;

each $R^{10}$ is independently selected from the group consisting of hydro, $C_{1-6}$alkyl, cycloalkyl, aryl, heteroaryl, $C_{1-6}$alkylenearyl, and $SO_2C_{1-6}$alkyl, or two $R^{10}$ groups are taken together to form an optionally substituted 3- to 8-membered ring;

each $R^{11}$ is independently selected from the group consisting of $C_{1-6}$alkyl, $C_{2-6}$alkynyl, aryl, heteroaryl, heterocycloalkyl, N(R$^9$)$_2$, N(R$^7$)C(O)R$^9$, N(R$^7$)CO$_2$R$^9$, OR$^9$, halo, N$_3$, CN, $C_{1-6}$alkylenearyl, $C_{1-6}$alkyleneN(R$^9$)$_2$, C(O)R$^9$, C(O)OR$^9$, C(O)N(R$^9$)$_2$, and

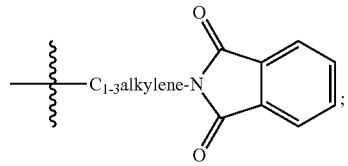

$R^{12}$ is selected from the group consisting of hydro, $C_{1-6}$alkyl, $C_{2-6}$alkenyl, cycloalkyl, heterocycloalkyl, aryl, heteroaryl, $SO_2R^{10}$, $C_{1-6}$alkyl substituted with one or more of halo, hydroxy, aryl, heteroaryl, heterocycloalkyl, N(R$^{10}$)$_2$, and $SO_2R^{10}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{10}$)$_2$, OCF$_3$, $C_{1-6}$alkyleneN(R$^{10}$)$_3^+$, $C_{3-8}$heterocycloalkyl, and CH(C$_{1-6}$alkyleneN(R$^{10}$)$_2$)$_2$;

$R^{13}$ and $R^{14}$, independently, are selected from the group consisting of hydro, OR$^9$, $C_{1-6}$alkyl, halo, N(R$^9$)$_2$, C(O)N(R$^9$)$_2$, $C_{1-3}$alkylenearyl, CN, NO$_2$, C(O)OR$^{17}$, C(O)R$^{17}$, and SR$^{17}$; $R^{15}$ is —C≡C—R$^{16}$ or —CF$_3$, or an $R^{14}$ and an $R^{15}$ group are taken together with the carbons to which they are attached to form a 5- or 6-membered carbocyclic aliphatic or aromatic ring system optionally containing one to three heteroatoms selected from the group consisting of O, NR$^{10}$, and S;

$R^{16}$ is selected from the group consisting of hydro, $C_{1-6}$alkyl, aryl, $C_{1-6}$alkylenearyl, heteroaryl, and $C_{1-6}$alkyleneheteroaryl;

each $R^{17}$ is independently selected from the group consisting of hydro, $C_{1-6}$alkyl, $C_{2-6}$alkenyl, aryl, $C_{1-3}$alkylenearyl, $C_{3-8}$cycloalkyl, and $C_{1-3}$alkylene$C_{3-8}$cycloalkyl;

or a pharmaceutically acceptable salt, or prodrug, or solvate thereof.

Specific compounds of structural formula (IV) or (V) are those wherein W' is selected from the group consisting of pyridazinyl, pyrimidinyl, pyrazinyl, and triazinyl, optionally substituted with one to four substituents selected from the group consisting of $C_{1-6}$alkyl, aryl, heteroaryl, $N(R^9)_2$, $C(O)N(R^9)_2$, $CO_2R^9$, $OR^9$, and halo.

Additional specific compounds of structural formula (IV) or (V) are those wherein $R^{12}$ is selected from the group consisting of optionally substituted $C_{1-6}$alkyl, $C_{1-6}$alkyleneN$(R^{10})_2$, $C_{1-6}$alkyleneheteroaryl, $C_{1-6}$alkyleneheterocycloalkyl, and $C_{3-8}$heterocycloalkyl. In other specific embodiments, $R^{12}$ is selected from the group consisting of $C_{1-6}$alkyl, $(CH_2)_{1-6}N(CH_3)_2$, $(CH_2)_{1-6}NH(CH_3)$,

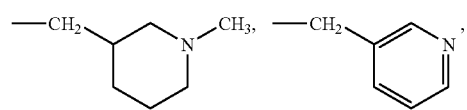
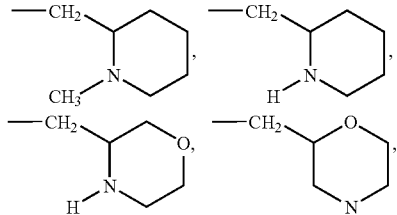
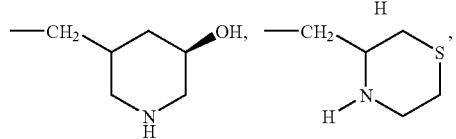
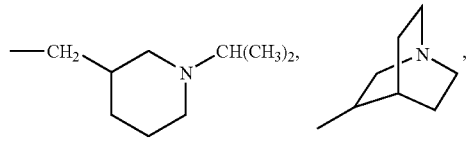
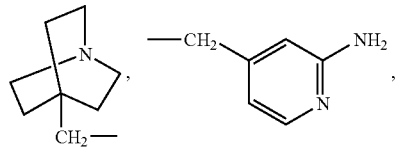
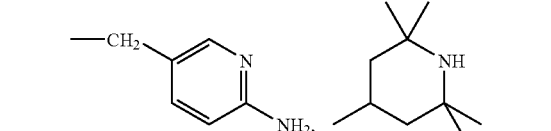
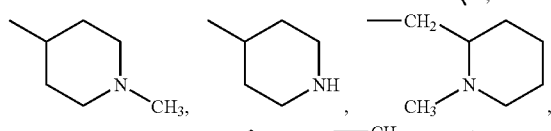
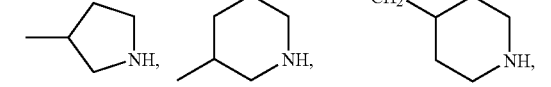

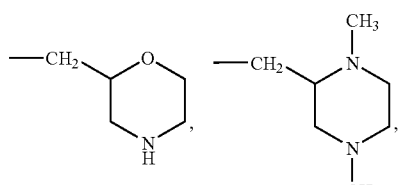
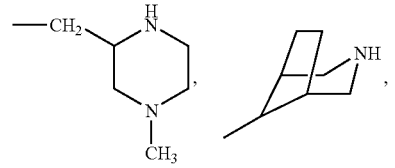
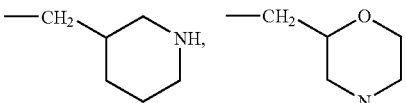
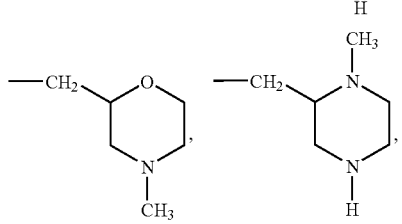
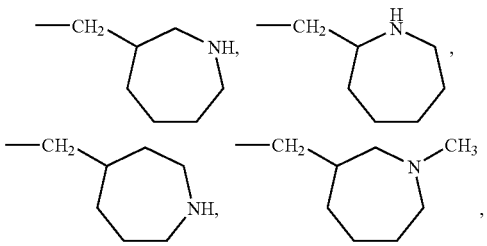
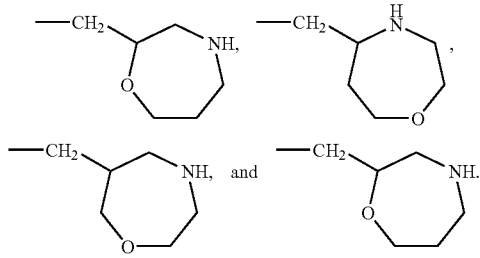

In other specific embodiments, W' is selected from the group consisting of

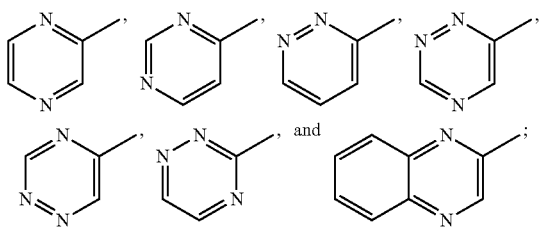

optionally substituted with one to four substituents selected from the group consisting of $C_{1-6}$alkyl, $C_{2-6}$-alkynyl, aryl, beteroaryl, CN, $CO_2R^9$, $N(R^9)_2$, $OR^9$, and halo.

In more specific embodiments, W' is

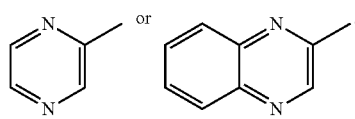

In a specific embodiment, W' is pyrazinyl and $X^3$ and $X^4$ each are N(H).

In other specific embodiments, W' is pyrazino-2-yl substituted with an $R^{11}$ group at the 5-position, i.e.,

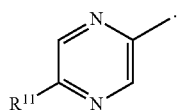

In specific embodiments, $R^{11}$ is $CH_3$ or null. Other specific embodiments include those wherein $R^{13}$ is H; $R^{14}$ is H; $R^{15}$ is selected from the group consisting of —C≡CH and $CF_3$; or $R^{14}$ and $R^{15}$ are taken together with the carbons to which they are attached to form

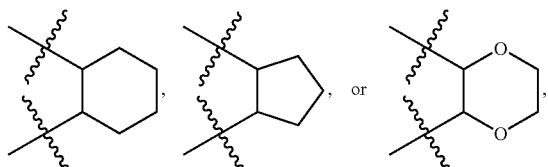 [SMILES: *C1CCCCC1* ; *C1CCCC1* ; *C1OCCOC1*]

In yet another specific embodiment, $R^{12}$ is selected from the group consisting of —$(CH_2)_2N(CH_3)_2$,

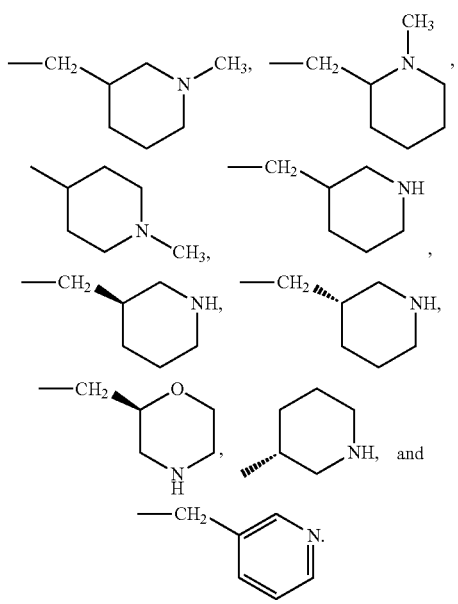

III. Diarylurea Compounds Described in WO 06/014359
i) A Compound Having a Formula (VI)

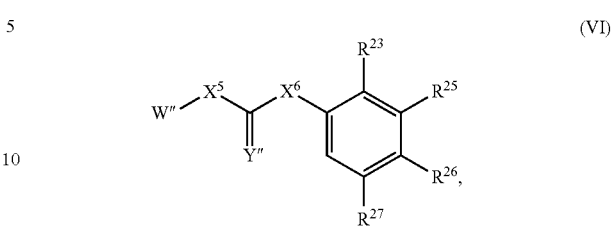

wherein $X^5$ is null, —O—, —S—, —$CH_2$—, or —$N(R^{18})$—;
$X^6$ is —O—, —S—, or —$N(R^{18})$—;
Y" is O or S; or =Y" represents two hydrogen atoms attached to a common carbon atom; W" is selected from the group consisting of heteroaryl, aryl, heterocycloalkyl, cycloalkyl, and $C_{1-6}$alkyl substituted with a heteroaryl or aryl group, wherein said aryl group W" is optionally substituted with one to four substituents represented by $R^{19}$, said heteroaryl group W" is optionally substituted with one to four substituents represented by $R^{22}$, and said heterocycloalkyl and cycloallryl groups W" are optionally substituted with one or two $C_{1-6}$alkyl substituents;
each $R^{18}$ is independently selected from the group consisting of hydro, $C_{1-6}$alkyl, $C_{2-6}$alkenyl, $C_{2-6}$alkynyl, and aryl;
each $R^{19}$ is independently selected from the group consisting of halo, optionally substituted $C_{1-6}$alkyl, $C_{2-6}$alkenyl, $OCF_3$, $NO_2$, CN, NC, $N(R^{20})_2$, $OR^{20}$, $CO_2R^{20}$, $C(O)N(R^{20})_2$, $C(O)R^{20}$, $N(R^{18})COR^{20}$, $N(R^{18})C(O)OR^{20}$, $N(R^{18})C(O)C_{1-6}$alkyleneC(O)$R^{20}$, $N(R^{18})C(O)C_{1-6}$alkyleneC(O)$OR^{20}$, $N(R^{18})C(O)C_{1-6}$alkyleneOR$^{20}$, $N(R^{18})C(O)C_{1-6}$alkyleneNHC(O)$OR^{20}$, $N(R^{18})C(O)C_{1-6}$alkyleneSO$_2$NR$^{20}$, $C_{1-6}$alkyleneOR$^{20}$, and $SR^{20}$;
each $R^{20}$ is independently selected from the group consisting of hydro, halo, $C_{1-6}$alkyl, $C_{2-6}$alkenyl, cycloalkyl, aryl, heteroaryl, $SO_2R^{21}$, $C_{1-6}$alkyl substituted with one or more of halo, hydroxy, aryl, heteroaryl, heterocycloalkyl, $N(R^{21})_2$, and $SO_2R^{21}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{21}$)$_2$, $OCF_3$, $C_{1-6}$alkyleneN(R$^{21}$)$_3^+$, $C_{3-8}$heterocycloalkyl, and $CH(C_{1-6}$alkyleneN(R$^{21}$)$_2$)$_2$, or two $R^{20}$ groups are taken together to form an optionally substituted 3- to 8-membered aliphatic ring;
each $R^{21}$ is independently selected from the group consisting of hydro, $C_{1-6}$alkyl, cycloalkyl, aryl, heteroaryl, $C_{1-6}$alkylenearyl, and $SO_2C_{1-6}$alkyl, or two $R^{21}$ groups are taken together to form an optionally substituted 3- to 8-membered ring;
each $R^{22}$ is independently selected from the group consisting of $C_{1-6}$alkyl, $C_{2-6}$alkynyl, aryl, heterocycloalkyl, $N(R^{20})_2$, $OR^{20}$, halo, $N_3$, CN, $C_{1-6}$alkylenearyl, $C_{1-6}$alkyleneN$(R^{20})_2$, $C(O)R^{20}$, $C(O)OR^{20}$, $C(O)N(R^2)_2$, $N(R^{18})C(O)R^{20}$, $N(R^{18})C(O)OR^{20}$, and

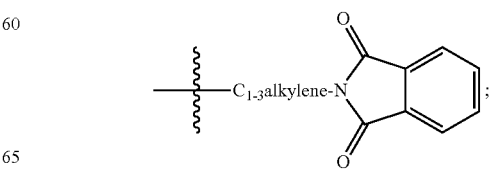

$R^{23}$ is —C≡C—$R^{24}$ or heteroaryl;

each $R^{24}$ is independently selected from the group consisting of hydro, $C_{1-6}$alkyl, aryl, $C_{1-6}$alkylenearyl, heteroaryl, $C_{1-6}$alkyleneheteroaryl, and alkoxy;

$R^{25}$, $R^{26}$, and $R^{27}$, independently, are selected from the group consisting of halo, optionally substituted $C_{1-6}$alkyl, $C_{2-6}$alkenyl, $C_{2-6}$alkynyl, $OCF_3$, $CF_3$, $NO_2$, CN, NC, $N(R^{20})_2$, $OR^{20}$, $CO_2R^{20}$, $C(O)N(R_2)_2$, $C(O)R^{20}$, $N(R^{18})COR^{20}$, $N(R^{18})C(O)OR^{20}$, $N(R^{20})C(O)OR^{20}$, $N(R^{18})C(O)C_{1-3}$alkyleneC(O)$R^{20}$, $N(R^{18})C(O)C_{1-3}$alkyleneC(O)$OR^{20}$, $N(R^{18})C(O)C_{1-3}$alkyleneOR$^{20}$, $N(R^{18})C(O)C_{1-3}$alkyleneNHC(O)$OR^{20}$, $N(R^{18})C(O)C_{1-3}$alkyleneSO$_2$NR$^{20}$, $C_{1-3}$alkyleneOR$^{20}$, and $SR^{20}$;

or a pharmaceutically acceptable salt, or prodrug, or solvate thereof.

ii) A Compound Having a Formula (VII)

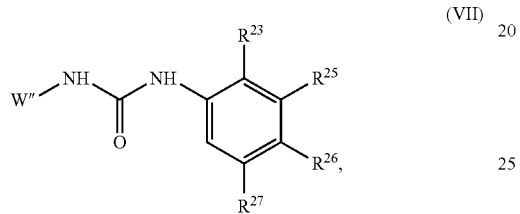

(VII)

wherein W" is selected from the group consisting of heteroaryl, aryl, heterocycloalkyl, cycloalkyl, and $C_{1-6}$alkyl substituted with a heteroaryl or aryl group, wherein said aryl group W" is optionally substituted with one to four substituents represented by $R^{19}$, said heteroaryl group W" is optionally substituted with one to four substituents represented by $R^{22}$, and said heterocycloalkyl and cycloalkyl groups W" are optionally substituted with one or two $C_{1-6}$alkyl substituents;

each $R^{18}$ is independently selected from the group consisting of hydro, $C_{1-6}$alkyl, $C_{2-6}$alkenyl, $C_{2-6}$alkynyl, and aryl;

each $R^{19}$ is independently selected from the group consisting of halo, optionally substituted $C_{1-6}$alkyl, $C_{2-6}$alkenyl, $OCF_3$, $NO_2$, CN, NC, $N(R^{20})_2$, $OR^{20}$, $CO_2R^{20}$, $C(O)N(R^{20})_2$, $C(O)R^{20}$, $N(R^{18})COR^{20}$, $N(R^{18})C(O)OR^{20}$, $N(R^{18})C(O)C_{1-6}$alkyleneC(O)$R^{20}$, $N(R^{18})C(O)C_{1-6}$alkyleneC(O)$OR^{20}$, $N(R^{18})C(O)C_{1-6}$alkyleneOR$^{20}$, $N(R^{18})C(O)C_{1-6}$alkyleneNHC(O)$OR^{20}$, $N(R^{18})C(O)C_{1-6}$alkyleneSO$_2$NR$^{20}$, $C_{1-6}$alkyleneOR$^{20}$, and $SR^{20}$;

each $R^{20}$ is independently selected from the group consisting of hydro, halo, $C_{1-6}$alkyl, $C_{2-6}$alkenyl, cycloalkyl, aryl, heteroaryl, $SO_2R^{21}$, $C_{1-6}$alkyl substituted with one or more of halo, hydroxy, aryl, heteroaryl, heterocycloalkyl, $N(R^{21})_2$, and $SO_2R^{21}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^{21}$)$_2$, $OCF_3$, $C_{1-6}$alkyleneN(R$^{21}$)$_3^+$, $C_{3-8}$heterocycloalkyl, and CH($C_{1-6}$alkyleneN(R$^{21}$)$_2$)$_2$, or two $R^{20}$ groups are taken together to form an optionally substituted 3- to 8-membered aliphatic ring;

each $R^{21}$ is independently selected from the group consisting of hydro, $C_{1-6}$alkyl, cycloalkyl, aryl, heteroaryl, $C_{1-6}$alkylenearyl, and $SO_2C_{1-6}$alkyl, or two $R^{21}$ groups are taken together to form an optionally substituted 3- to 8-membered ring;

$R^{22}$ is selected from the group consisting of $C_{1-6}$alkyl, $C_{2-6}$alkynyl, aryl, heterocycloalkyl, $N(R^{20})_2$, $OR^{20}$, halo, $N_3$, CN, $C_{1-6}$alkylenearyl, $C_{1-6}$alkyleneN(R$^{20}$)$_2$, $C(O)R^{20}$, $C(O)OR^{20}$, $C(O)N(R^{20})_2$, $N(R^{18})C(O)R^{20}$, $N(R^{18})C(O)OR^{20}$, and

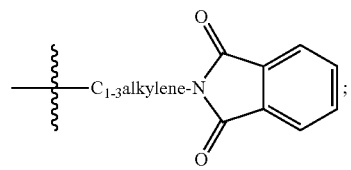

$R^{23}$ is —C≡C—$R^{24}$ or heteroaryl;

each $R^{24}$ is independently selected from the group consisting of hydro, $C_{1-6}$alkyl, aryl, $C_{1-6}$alkylenearyl, heteroaryl, $C_{1-6}$alkyleneheteroaryl, and alkoxy;

$R^{25}$, $R^{26}$, and $R^{27}$, independently, are selected from the group consisting of halo, optionally substituted $C_{1-6}$alkyl, $C_{2-6}$alkenyl, $C_{2-6}$alkynyl, $OCF_3$, $CF_3$, $NO_2$, CN, NC, $N(R^{20})_2$, $OR^{20}$, $CO_2R^{20}$, $C(O)N(R^{20})_2$, $C(O)R^{20}$, $N(R^{18})COR^{20}$, $N(R^{18})C(O)OR^{20}$, $N(R^{20})C(O)OR^{20}$, $N(R^{18})C(O)C_{1-3}$alkyleneC(O)$R^{20}$, $N(R^{18})C(O)C_{1-3}$alkyleneC(O)$OR^{20}$, $N(R^{18})C(O)C_{1-3}$alkyleneOR$^{20}$, $N(R^{18})C(O)C_{1-3}$alkyleneNHC(O)$OR^{20}$, $N(R^{18})C(O)C_{1-3}$alkyleneSO$_2$NR$^{20}$, $C_{1-3}$alkyleneOR$^{20}$, and $SR^{20}$;

or a pharmaceutically acceptable salt, or prodrug, or solvate thereof.

Specific compounds of the present invention are those wherein $X^5$ and $X^6$ are —N(H)—; Y" is O or S; and W" is optionally substituted heteroaryl. In one embodiment, W" is heteroaryl containing at least two heteroatoms selected from the group consisting of N, O, and S, said heteroaryl ring optionally substituted with one to four substituents selected from the group consisting of optionally substituted $C_{1-6}$alkyl, aryl, $N(R^{20})_2$, $OR^{20}$, $C(O)N(R^{20})_2$, $CO_2R^{20}$, CN, and halo, wherein $R^{20}$ is as previously defined.

Other specific compounds of structural formula (VI) are those wherein W" is selected from the group consisting of pyridazinyl, pyrimidinyl, pyrazinyl, and triazinyl, optionally substituted with one to four substituents selected from the group consisting of $C_{1-6}$alkyl, aryl, $N(R^{20})_2$, $C(O)N(R^{20})_2$, $CO_2R^{20}$, $OR^{20}$, and halo.

In some specific embodiments, W" is selected from the group consisting of

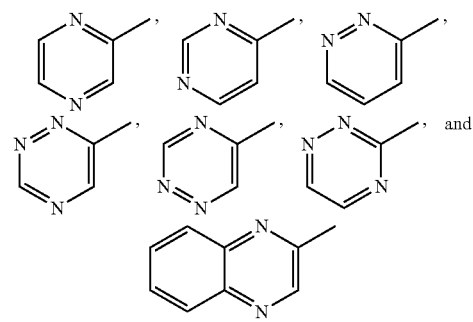

optionally substituted with one to four substituents selected from the group consisting of $C_{1-6}$alkyl, $C_{2-6}$alkynyl, aryl, heteroaryl, CN, $CO_2R^{20}$, $N(R^{20})_2$, $OR^{20}$, and halo.

In more specific embodiments, W″ is

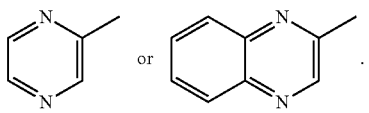

In a most specific embodiment, W″ is pyrazinyl and $X^5$ and $X^6$ each are N(H).

In yet another specific embodiment, $R^{23}$ is heteroaryl selected from the group consisting of

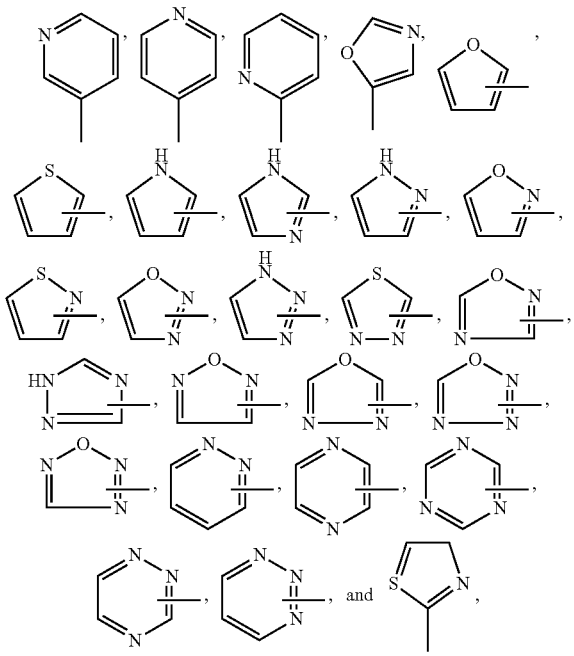

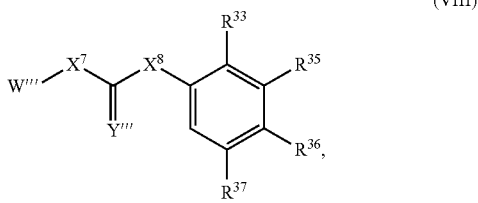

and optionally substituted with $C_{1-3}$alkyleneN$(R^{21})_2$.

IV. Diarylurea Compounds Described in WO 06/021002 i) A Compound Having a Formula (VIII)

(VIII)

wherein $X^7$ is null, —O—, —S—, —CH$_2$—, or —N($R^{28}$)—;
$X^8$ is —O—, —S—, or —N($R^{28}$)—;
Y‴ is O or S; or =Y‴ represents two hydrogen atoms attached to a common carbon atom;
W‴ is selected from the group consisting of heteroaryl, aryl, heterocycloalkyl, cycloalkyl, and $C_{1-6}$alkyl substituted with a heteroaryl or aryl group, wherein (a) said aryl or heteroaryl group of group W‴ is substituted with at least one of CF$_3$ and heteroaryl, (b) said aryl group of group W‴ is optionally substituted with one to three substituents represented by $R^{29}$, and (c) said heteroaryl group of group W‴ is optionally substituted with one to three substituents represented by $R^{32}$;

each $R^{28}$ is independently selected from the group consisting of hydro, $C_{1-6}$alkyl, $C_{2-6}$alkenyl, $C_{2-6}$alkynyl, and aryl;
each $R^{29}$ is independently selected from the group consisting of heteroaryl, halo, optionally substituted $C_{1-6}$alkyl, $C_{2-6}$alkenyl, OCF$_3$, NO$_2$, CN, NC, N$(R^{30})_2$, OR$^{30}$, CO$_2$R$^{30}$, C(O)N$(R^{30})_2$, C(O)R$^{30}$, N$(R^{28})$COR$^{30}$, N$(R^{28})$C(O)OR$^{30}$, N$(R^{28})$C(O)$C_{1-6}$alkyleneC(O)R$^{30}$, N$(R^{28})$C(O)$C_{1-6}$alkyleneC(O)OR$^{30}$, N$(R^{28})$C(O)$C_{1-6}$alkyleneOR$^{30}$, N$(R^{28})$C(O)$C_{1-6}$alkyleneNHC(O)OR$^{30}$, N$(R^{28})$C(O)$C_{1-6}$alkyleneSO$_2$NR$^{30}$, $C_{1-6}$alkyleneOR$^{30}$, and SR$^{30}$;
each $R^{30}$ is independently selected from the group consisting of hydro, halo, $C_{1-6}$alkyl, $C_{2-6}$alkenyl, cycloalkyl, aryl, heteroaryl, CO$_2$R$^{31}$, SO$_2$R$^{31}$, $C_{1-6}$alkyl substituted with one or more of halo, hydroxy, aryl, heteroaryl, heterocycloalkyl, N$(R^{31})_2$, and SO$_2$R$^{31}$;
$C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN$(R^{31})_2$, OCF$_3$, $C_{1-6}$alkyleneN$(R^{31})_3^+$, $C_{3-8}$heterocycloalkyl, and CH$(C_{1-6}$alkyleneN$(R^{31})_2)_2$, or two $R^{30}$ groups are taken together to form an optionally substituted 3- to 6-membered aliphatic ring;
each $R^{31}$ is independently selected from the group consisting of hydro, $C_{1-6}$alkyl, cycloalkyl, aryl, heteroaryl, $C_{1-6}$alkylenearyl, and SO$_2C_{1-6}$alkyl, or two $R^{31}$ groups are taken together to form an optionally substituted 3- to 6-membered ring;
each $R^{32}$ is independently selected from the group consisting of $C_{1-6}$alkyl, aryl, heteroaryl, heterocycloalkyl, N$(R^{30})_2$, OR$^{30}$, halo, N$_3$, CN, $C_{1-6}$alkylenearyl, $C_{1-6}$alkyleneN$(R^{30})_2$, C(O)R$^{30}$, C(O)OR$^{30}$, C(O)N$(R^{30})_2$, N$(R^{28})$C(O)R$^{30}$, N$(R^{28})$C(O)OR$^{30}$, CF$_3$, and

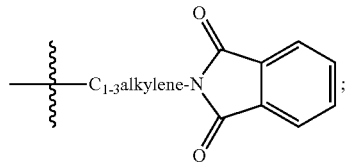

$R^{33}$ is selected from the group consisting of OR$^{38}$, —C≡C—R$^{34}$, and heteroaryl;
each $R^{34}$ is independently selected from the group consisting of hydro, $C_{1-6}$alkyl, aryl, $C_{1-6}$alkylenearyl, heteroaryl, $C_{1-6}$alkyleneheteroaryl, and alkoxy;
$R^{35}$, $R^{36}$, and $R^{37}$, independently, are selected from the group consisting of hydro, halo, optionally substituted $C_{1-6}$alkyl, $C_{2-6}$alkenyl, $C_{2-6}$alkynyl, OCF$_3$, CF$_3$, NO$_2$, CN, NC, N$(R^{30})_2$, OR$^{30}$, CO$_2$R$^{30}$, C(O)N$(R^{30})_2$, C(O)R$^{30}$, N$(R^{28})$COR$_{30}$, N$(R^{28})$C(O)OR$^{30}$, N$(R^{28})$C(O)OR$^{30}$, N$(R^{28})$C(O)$C_{1-6}$alkyleneC(O)R$^{30}$, N$(R^{28})$C(O)$C_{1-6}$alkyleneC(O)OR$^{30}$, N$(R^{28})$C(O)$C_{1-3}$alkryleneOR$^{30}$, N$(R^{28})$C(O)$C_{1-6}$alkyleneNHC(O)OR$^{30}$, N$(R^{28})$C(O)$C_{1-6}$lkyleneSO$_2$NR$^{30}$, $C_{1-6}$alkyleneOR$^{30}$, and SR$^{30}$;
$R^{38}$ is selected from the group consisting of hydro, $C_{1-6}$alkyl, $C_{2-6}$alkenyl, cycloalkyl, heterocycloalkyl, aryl, heteroaryl, SO$_2$R$^{31}$, $C_{1-6}$alkyl substituted with one or more of halo, hydroxy, aryl, heteroaryl, N$(R^{31})_2$, and SO$_2$R$^{31}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN$(R^{31})_2$, OCF$_3$, $C_{1-6}$alkyleneN$(R^{31})_3^+$, $C_{3-8}$heterocycloalkyl, and CH$(C_{1-6}$alkyleneN$(R^{31})_2)_2$;
and a pharmaceutically acceptable salt, prodrug, or solvate thereof ii) A Compound Having a Formula (IX)

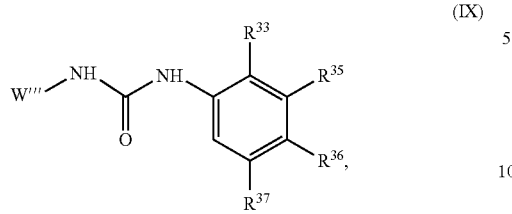

wherein W''' is selected from the group consisting of heteroaryl, aryl, heterocycloalkyl, cycloalkyl, and $C_{1-6}$alkyl substituted with a heteroaryl or aryl group, wherein (a) said aryl or heteroaryl group of group W''' is substituted with at least one of $CF_3$ and heteroaryl, (b) said aryl group of group W''' is optionally substituted with one to three substituents represented by $R^{29}$, and (c) said heteroaryl group of group W''' is optionally substituted with one to three substituents represented by $R^{32}$;

each $R^{28}$ is independently selected from the group consisting of hydro, $C_{1-6}$alkyl, $C_{2-6}$alkenyl, $C_{2-6}$alkynyl, and aryl;

each $R^{29}$ is independently selected from the group consisting of heteroaryl, halo, optionally substituted $C_{1-6}$alkyl, $C_{2-6}$alkenyl, $OCF_3$, $NO_2$, CN, NC, $N(R^{30})_2$, $OR^{30}$, $CO_2R^{30}$, $C(O)N(R^{30})_2$, $C(O)R^{30}$, $N(R^{28})COR^{30}$, $N(R^{28})C(O)OR^{30}$, $N(R^{28})C(O)C_{1-6}$alkyleneC(O)R^{30}$, $N(R^{28})C(O)C_{1-6}$alkyleneC(O)OR^{30}$, $N(R^{28})C(O)C_{1-6}$alkyleneOR^{30}$, $N(R^{28})C(O)C_{1-6}$alkyleneNHC(O)OR^{30}$, $N(R^{28})C(O)C_{1-6}$alkyleneSO_2NR^{30}$, $C_{1-6}$alkyleneOR^{30}$, and $SR^{30}$;

each $R^{30}$ is independently selected from the group consisting of hydro, halo, $C_{1-6}$alkyl, $C_{2-6}$alkenyl, cycloalkyl, aryl, heteroaryl, $CO_2R^{31}$, $SO_2R^{31}$, $C_{1-6}$alkyl substituted with one or more of halo, hydroxy, aryl, heteroaryl, heterocycloalkyl, $N(R^{31})$, and $SO_2R^{31}$;

$C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R^{31})_2$, $OCF_3$, $C_{1-6}$alkyleneN(R^{31})_3^+$, $C_{3-8}$heterocycloalkyl, and $CH(C_{1-6}$alkyleneN(R^{31})_2)_2$, or two $R^{30}$ groups are taken together to form an optionally substituted 3- to 6-membered aliphatic ring;

each $R^{31}$ is independently selected from the group consisting of hydro, $C_{1-6}$alkyl, cycloalkyl, aryl, heteroaryl, $C_{1-6}$alkylenearyl, and $SO_2C_{1-6}$alkyl, or two $R^{31}$ groups are taken together to form an optionally substituted 3- to 6-membered ring;

each $R^{32}$ is independently selected from the group consisting of $C_{1-6}$alkyl, aryl, heteroaryl, heterocycloalkyl, $N(R^{30})_2$, $OR^{30}$, halo, $N_3$, CN, $C_{1-6}$alkylenearyl, $C_{1-6}$alkyleneN(R^{30})_2$, $C(O)R^{30}$, $C(O)OR^{30}$, $C(O)N(R^{30})_2$, $N(R^{28})C(O)R^{30}$, $N(R^{28})C(O)OR^{30}$, $CF_3$, and

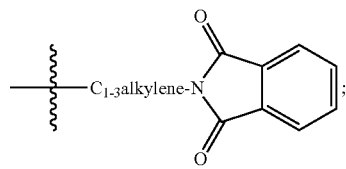

$R^{33}$ is selected from the group consisting of $OR^{38}$, —C≡C—$R^{34}$, and heteroaryl;

each $R^{34}$ is independently selected from the group consisting of hydro, $C_{1-6}$alkyl, aryl, $C_{1-6}$alkylenearyl, heteroaryl, $C_{1-6}$alkyleneheteroaryl, and alkoxy;

$R^{35}$, $R^{36}$, and $R^{37}$, independently, are selected from the group consisting of hydro, halo, optionally substituted $C_{1-6}$alkyl, $C_{2-6}$alkenyl, $C_{2-6}$alkynyl, $OCF_3$, $CF_3$, $NO_2$, CN, NC, $N(R^{30})_2$, $OR^{30}$, $CO_2R^{30}$, $C(O)N(R^{30})_2$, $C(O)R^{30}$, $N(R^{28})COR^{30}$, $N(R^{28})C(O)OR^{30}$, $N(R^{28})C(O)OR^{30}$, $N(R^{28})C(O)C_{1-3}$alkyleneC(O)R^{30}$, $N(R^{28})C(O)C_{1-6}$alkyleneC(O)OR^{30}$, $N(R^{28})C(O)C_{1-3}$alkyleneOR^{30}$, $N(R^{28})C(O)C_{1-6}$alkyleneNHC(O)OR^{30}$, $N(R^{28})C(O)C_{1-6}$alkyleneSO_2NR^{30}$, $C_{1-6}$alkyleneOR^{30}$, and $SR^{30}$;

$R^{38}$ is selected from the group consisting of hydro, $C_{1-6}$alkyl, $C_{2-6}$alkenyl, cycloalkyl, heterocycloalkyl, aryl, heteroaryl, $SO_2R^{31}$, $C_{1-6}$alkyl substituted with one or more of halo, hydroxy, aryl, heteroaryl, $N(R^{31})_2$, and $SO_2R^{31}$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R^{31})_2$, $OCF_3$, $C_{1-6}$alkyleneN(R^{31})_3^+$, $C_{3-8}$heterocycloalkyl, and $CH(C_{1-6}$alkyleneN(R^{31})_2)_2$;

or a pharmaceutically acceptable salt, prodrug, or solvate thereof.

Specific compounds of the present invention are those wherein $X^7$ and $X^8$ are —N(H)—; Y''' is O or S; and W''' is heteroaryl. In one embodiment, W''' is heteroaryl containing at least two heteroatoms selected from the group consisting of N, O, and S, said heteroaryl ring optionally substituted with one or two substituents selected from the group consisting of optionally substituted $C_{1-6}$alkyl, aryl, heteroaryl, $N(R^{30})_2$, $OR^{30}$, $C(O)N(R^{30})_2$, $CO_2R^{30}$, CN, and halo, wherein $R^{30}$ is as previously defined.

Other specific compounds of structural formula (VIII) or (IX) are those wherein W''' is selected from the group consisting of pyridazinyl, pyrimidinyl, pyrazinyl, and triazinyl, optionally substituted with one or two substituents selected from the group consisting of $C_{1-6}$alkyl, aryl, heteroaryl, $N(R^{30})_2$, $C(O)N(R^{30})_2$, $CO_2R^{30}$, $OR^{30}$, and halo.

In some specific embodiments, W''' is selected from the group consisting of

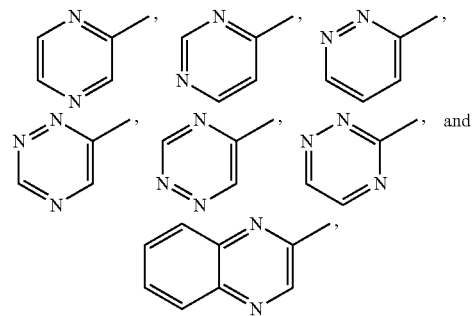

optionally substituted with one to four substituents selected from the group consisting of $C_{1-6}$alkyl, $C_{2-6}$-alkynyl, aryl, heteroaryl, CN, $CO_2R^{30}$, $N(R^{30})_2$, $OR^{30}$, and halo.

In more specific embodiments, W''' is

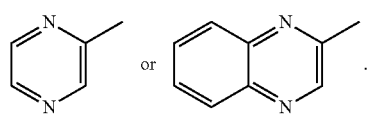

In a most specific embodiment, W is pyrazinyl and $X^7$ and $X^8$ each are N(H).

In yet another specific embodiment, the heteroaryl group substituent on W''' and the heteroaryl group of $R^{33}$, independently, are selected from the group consisting of

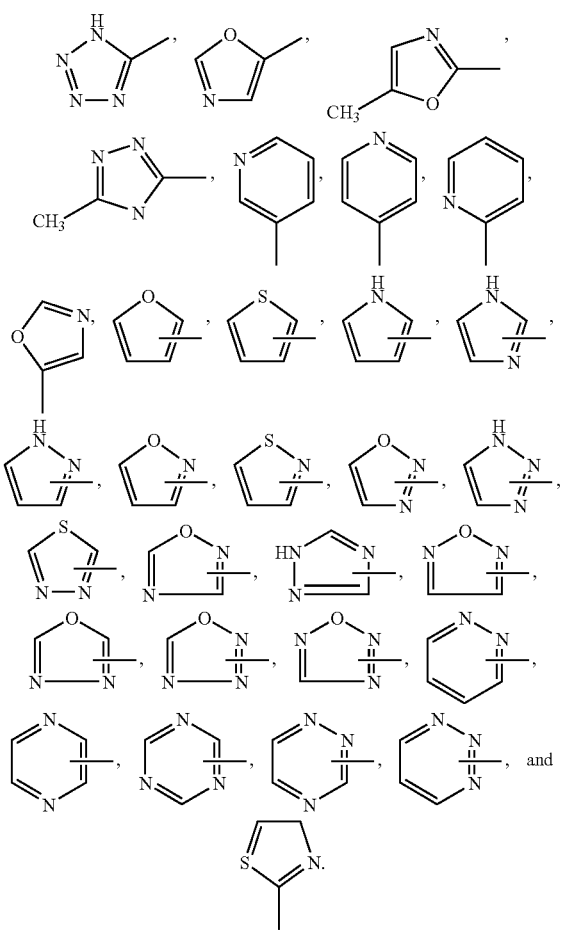

V. Diarylurea Compounds Described in PCT/US06/011584

A Compound of Having a Formula (X)

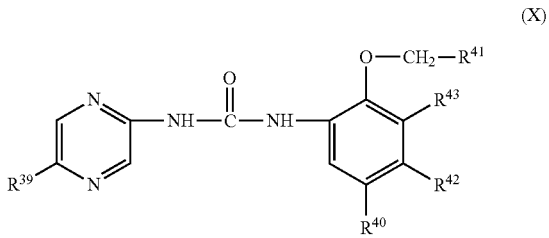

wherein $R^{39}$ is halo, $C_{1-3}$alkyl, CN, and $CF_3$;

$R^{40}$ is hydrogen, $C_{1-3}$alkyl, CN, $OC_{1-3}$alkyl, halo, or $N(R^{45})_2$, wherein each $R^{45}$, independently, is hydrogen or $C_{1-3}$alkyl;

$R^{41}$ is a 6- or 7-membered saturated heterocyclic ring containing one ring N—$R^{44}$ group and either a second ring N—$R^{44}$ group, a ring oxygen, or a ring sulfur, wherein each $R^{44}$, independently, is hydrogen, $C_{1-3}$alkyl, $CH_2CN$, or $CH_2CH_2CN$, and wherein $R^{41}$ is optionally substituted with oxo(=O);

$R^{42}$ is hydrogen, $C_{1-3}$alkyl, $OC_{1-3}$alkyl, $SC_{1-3}$alkyl, $N(R^{45})_2$, $NR^{45}C(=O)C_{1-3}$alkyl, or a 5- or 6-membered saturated heterocyclic ring containing one N—$R^{44}$ group and optionally ring substituted with one to three $C_{1-3}$alkyl groups;

or $R^{40}$ and $R^{42}$ are taken together with the carbons to which they are attached to form a 5- to 7-membered saturated carbocyclic ring;

and $R^{43}$ is hydrogen or halo, provided that at least one of $R^{40}$ and $R^{42}$ is different from hydrogen, and that when $R^{43}$ is halo, $R^{40}$ or $R^{42}$ is hydrogen, or a pharmaceutically acceptable salt, prodrug, or solvate thereof.

In one specific embodiment, the compounds have a structural formula (XI):

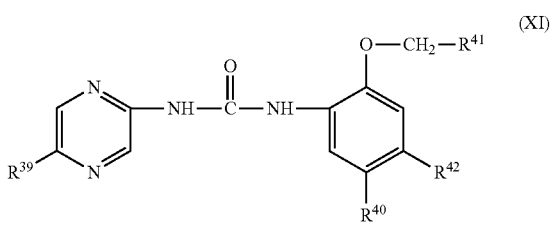

wherein $R^{39}$ is halo, $C_{1-3}$alkyl, CN, or $CF_3$;

$R^{40}$ is hydrogen, $C_{1-3}$alkyl, CN, $OC_{1-3}$alkyl, halo, or $N(R^{45})_2$ wherein $R^{45}$, independently, is hydrogen or $C_{1-3}$alkyl;

$R^{41}$ is a 6- or 7-membered saturated heterocyclic ring containing one ring N—$R^{44}$ group and either a second ring N—$R^{44}$ group, a ring oxygen, or a ring sulfur, wherein each $R^{44}$, independently, is hydrogen, $C_{1-3}$alkyl, or $CH_2CN$, and wherein $R^{41}$ is optionally substituted with oxo (=O);

$R^{42}$ is hydrogen, $C_{1-3}$alkyl, $OC_{1-3}$alkyl, or halo;

or $R^{40}$ and $R^{42}$ are taken together with the carbons to which they are attached to form a 5- to 7-membered saturated carbocyclic ring, provided that at least one of $R^{40}$ and $R^{42}$ is different from hydrogen, or pharmaceutically acceptable salts, prodrugs, or solvates thereof.

In one specific embodiment of compounds of formulas (X) and (XI), $R^{39}$ is chloro, methyl, CN, or $CF_3$. In another specific embodiment, $R^{40}$ is hydrogen, methyl, ethyl, chloro, bromo, dimethylamino, cyano, or methoxy. In more specific embodiments, $R^2$ is different from hydrogen.

In other specific embodiments of formulas (X) and (XI), $R^{42}$ is methyl, chloro, fluoro, methoxy, isopropoxy, dimethylamino, —$SCH_3$, —$NHC(=O)CH(CH_3)_2$, —$NHC(=O)CH_3$, pyrrolidinyl, or 3,3-dimethyl-pyrrolidinyl. In more specific embodiments, $R^{42}$ is methyl, chloro, or methoxy. In still another specific embodiment, $R^{40}$ and $R^{42}$ are taken together with the carbons to which they are attached to form a five-membered or a six-membered, saturated carbocyclic ring.

In still another specific embodiment of formulas (X) and (XI), when $R^{43}$ is halo, $R^{42}$ is hydrogen. In a specific embodiment, $R^{43}$ is fluoro. In more specific embodiments, $R^{43}$ is hydrogen.

In one embodiment of formulas (X) and (XI), when $R^{39}$ is cyano, $R^{40}$ is hydrogen and $R^{42}$ preferably is chloro or methyl. In another embodiment, $R^{43}$ is fluoro, $R^{42}$ is hydrogen, and $R^{40}$ is methyl, chloro, or bromo.

Examples of specific $R^{41}$ groups in formulas (X) and (XI) include, but are not limited to,

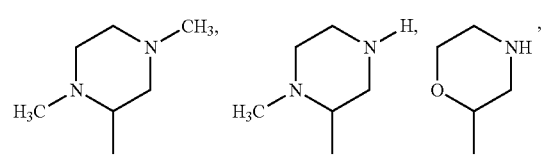
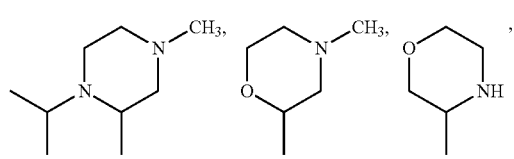
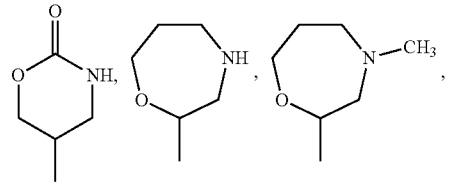
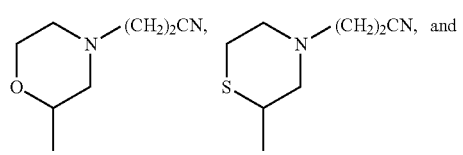
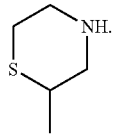
Specific Compounds of Formula (X) Include
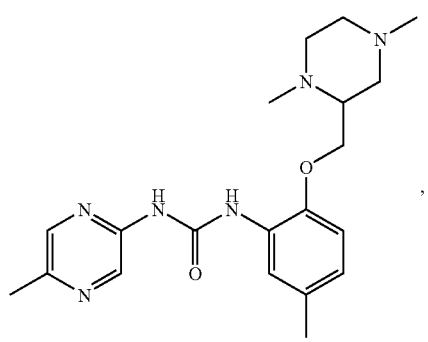
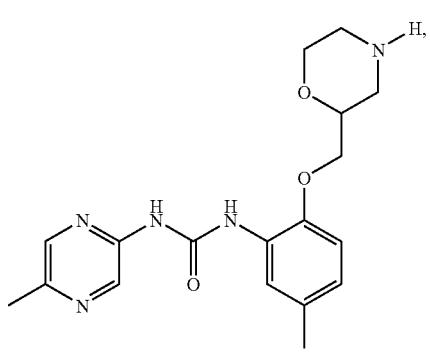
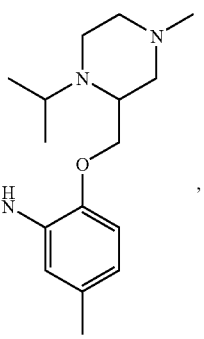
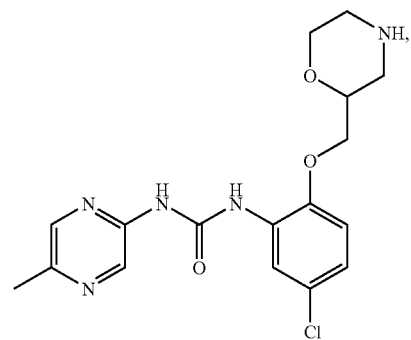
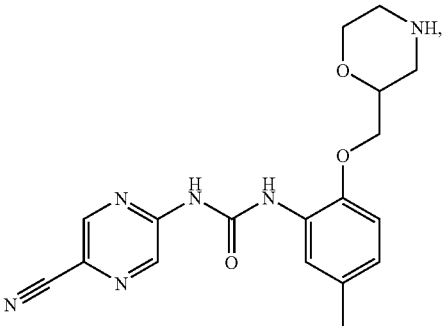
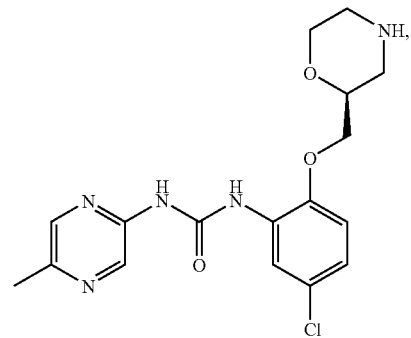
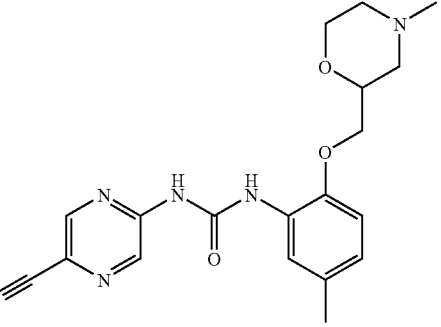

-continued
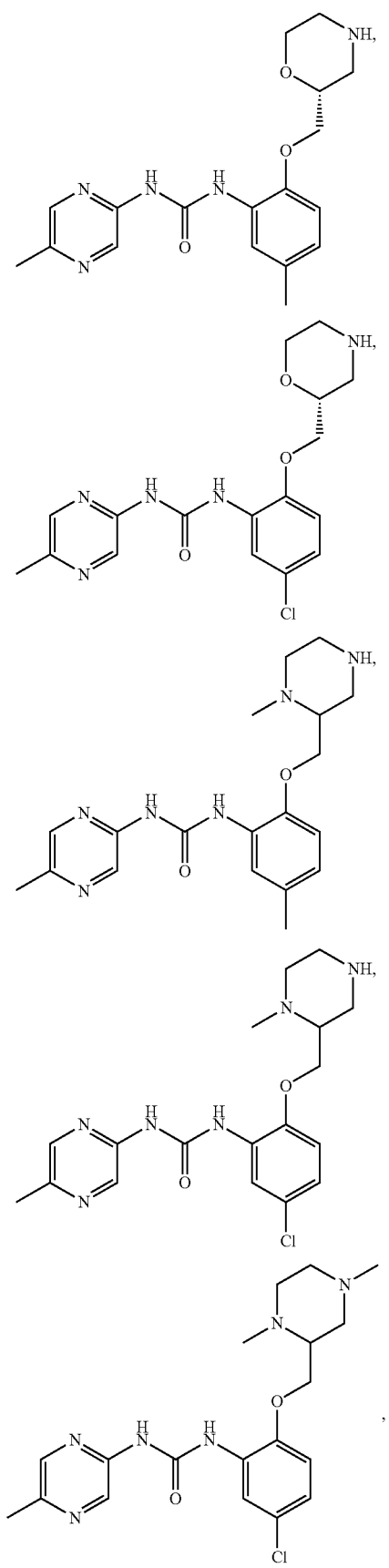
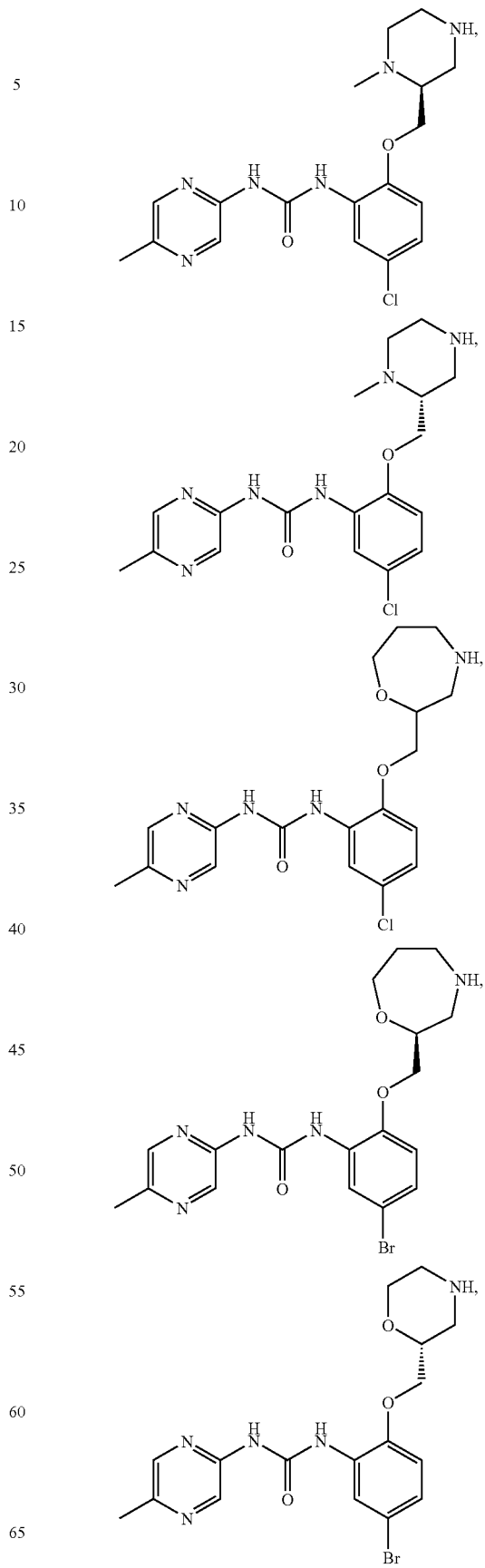

-continued
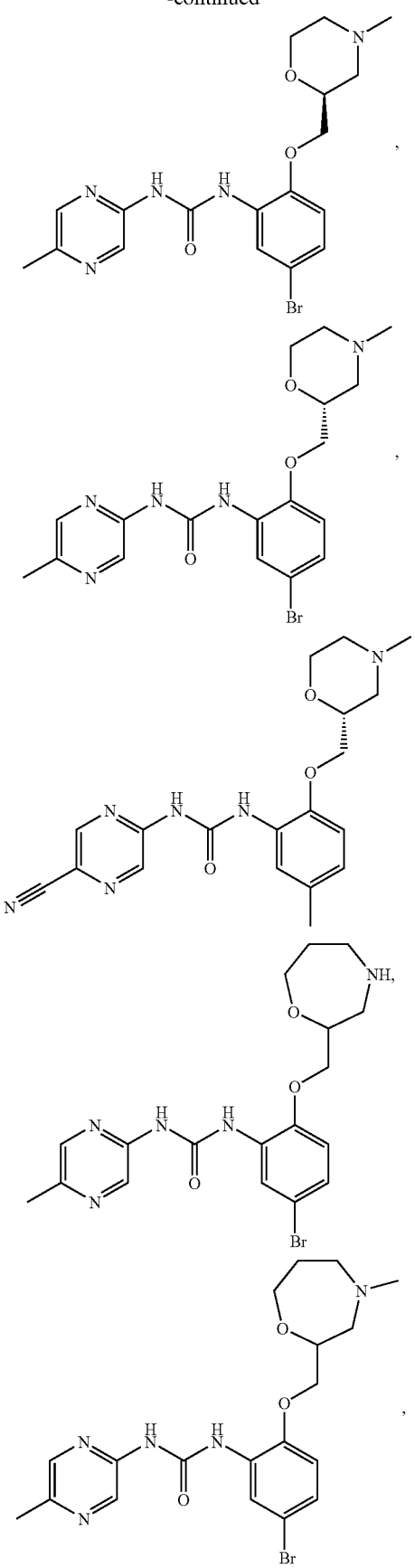
-continued
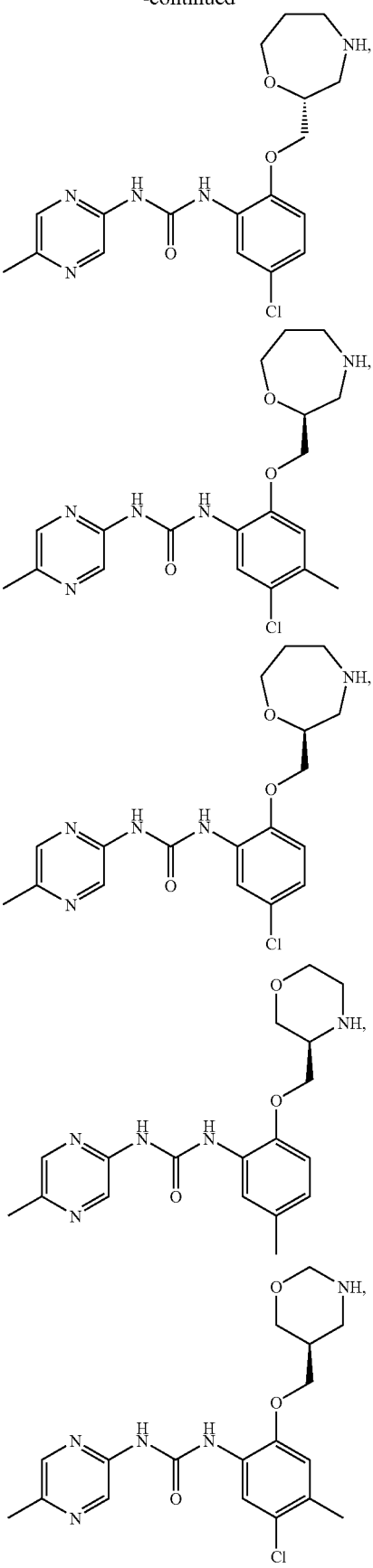

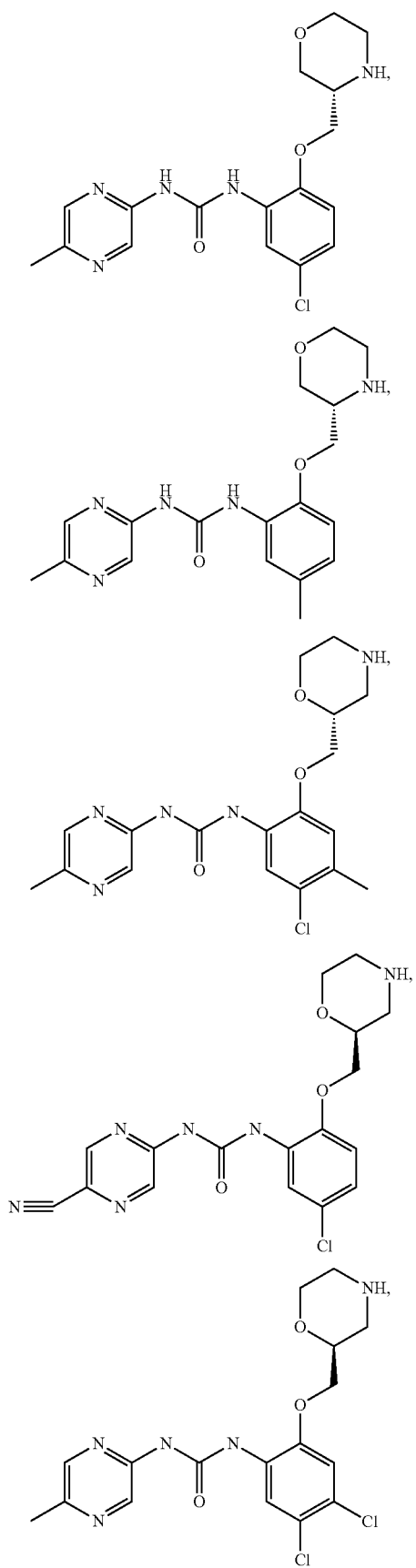
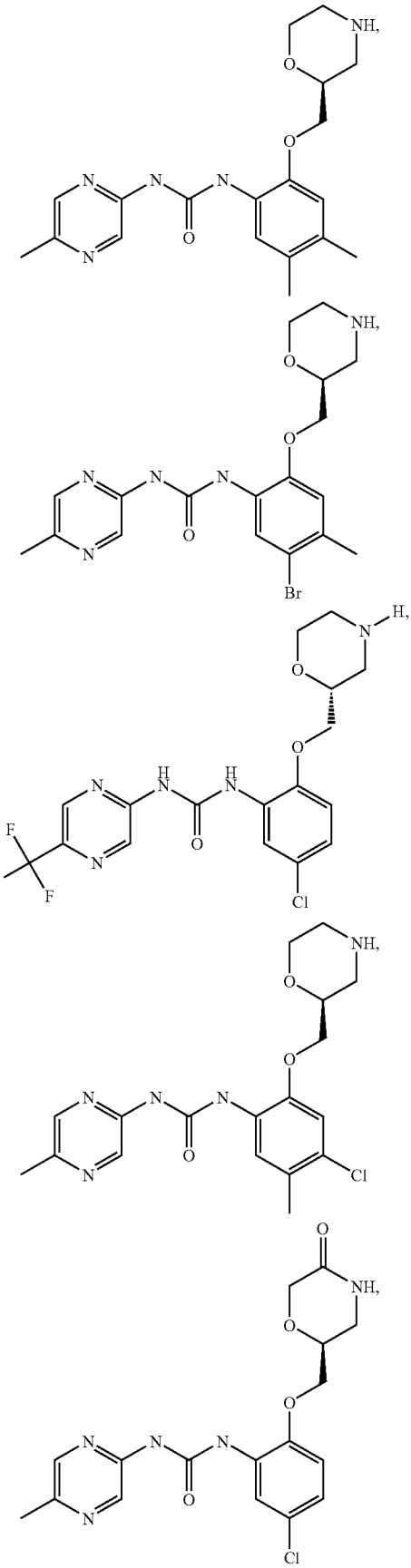

33
-continued
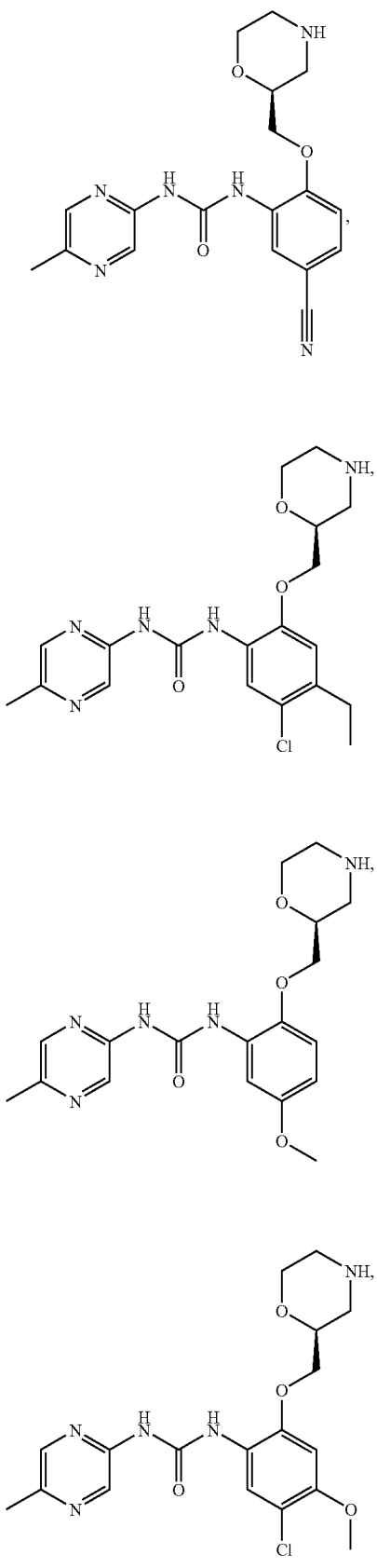
34
-continued
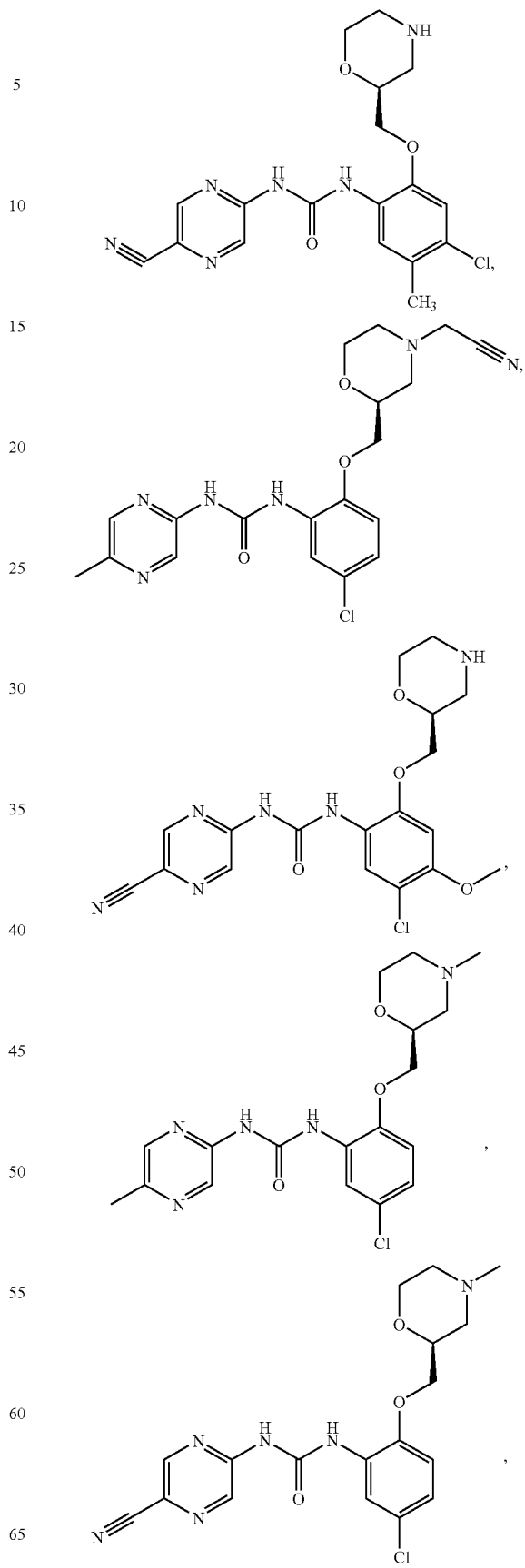

35
-continued
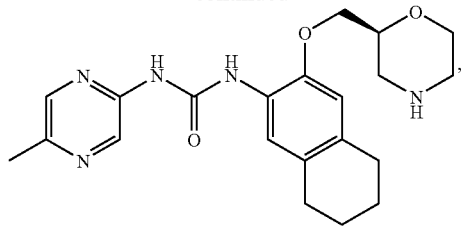
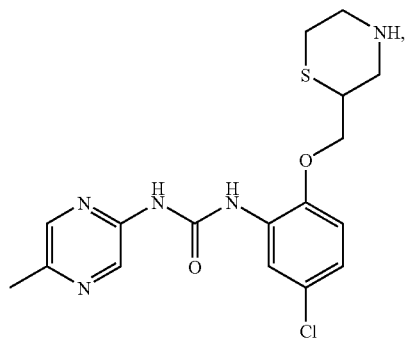
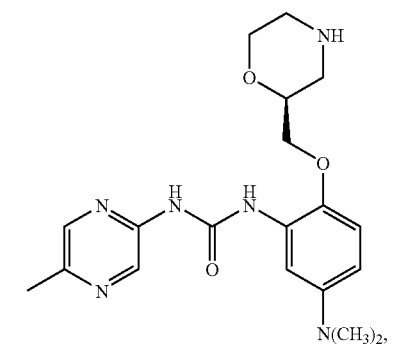
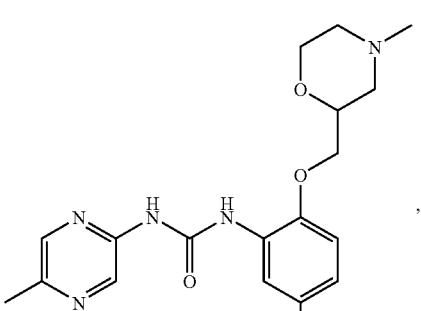
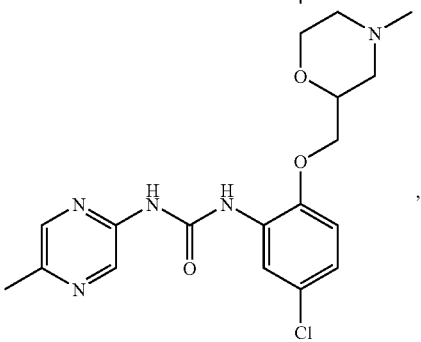
36
-continued
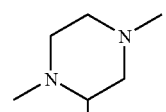
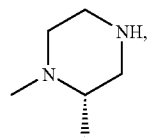
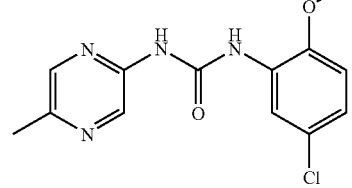
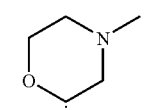
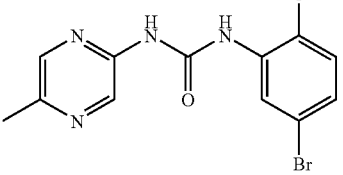
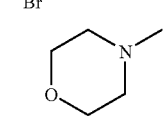
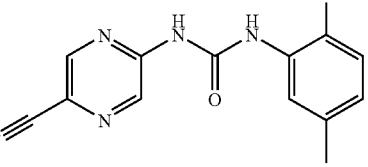
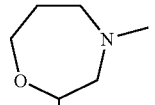

37
-continued
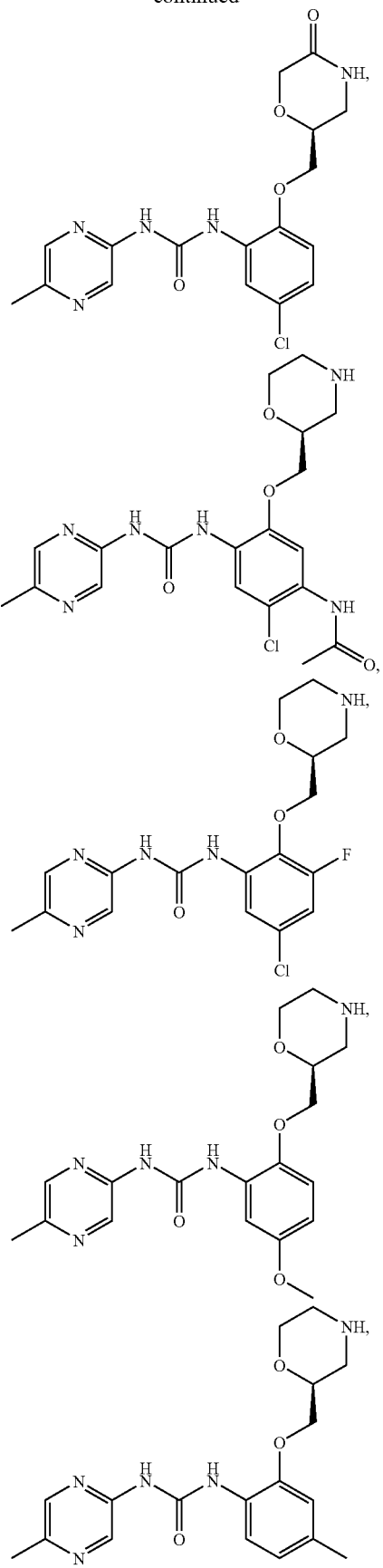
38
-continued
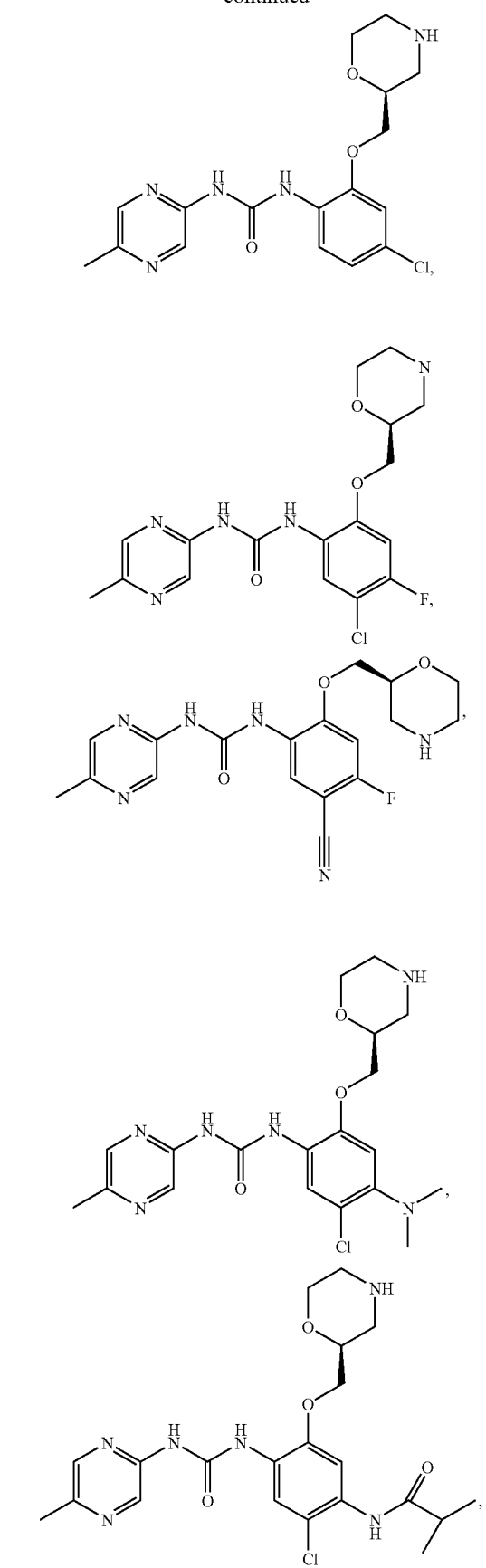

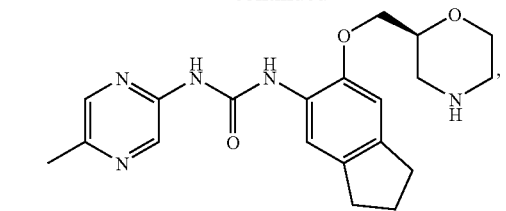
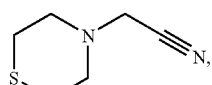
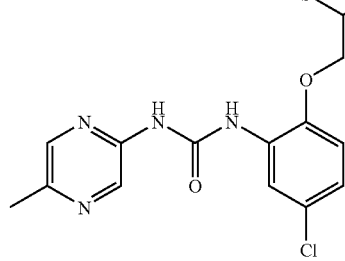
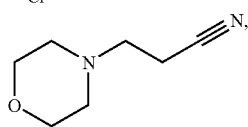
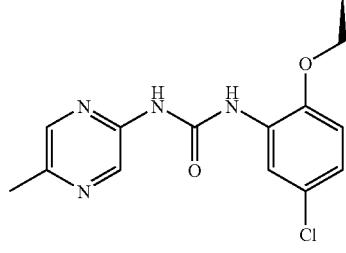
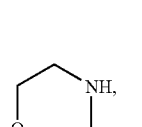
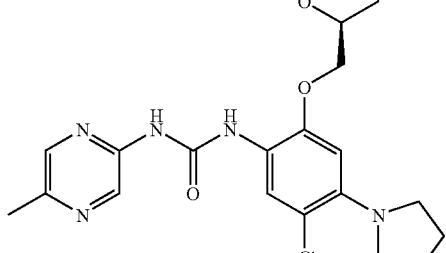
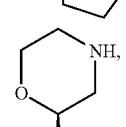
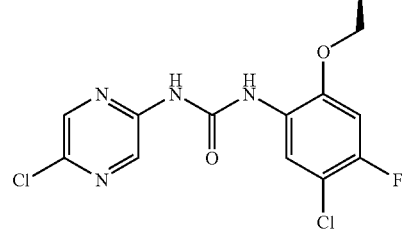
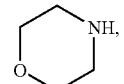
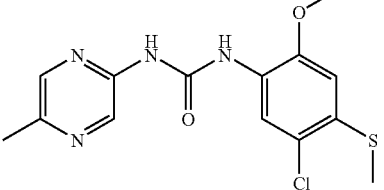
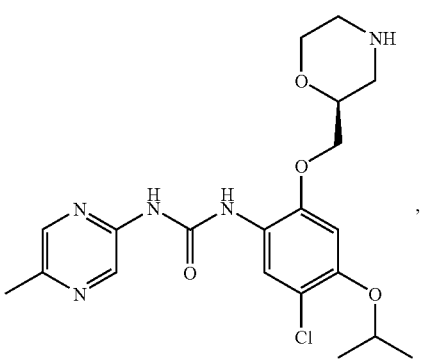
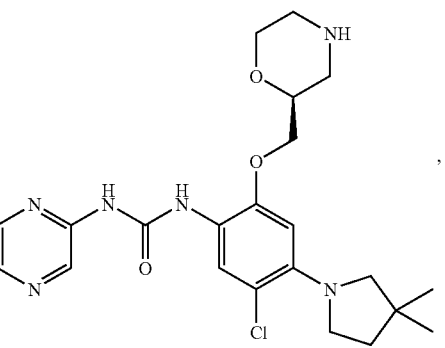
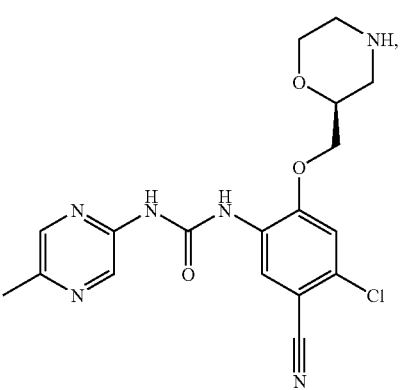

-continued

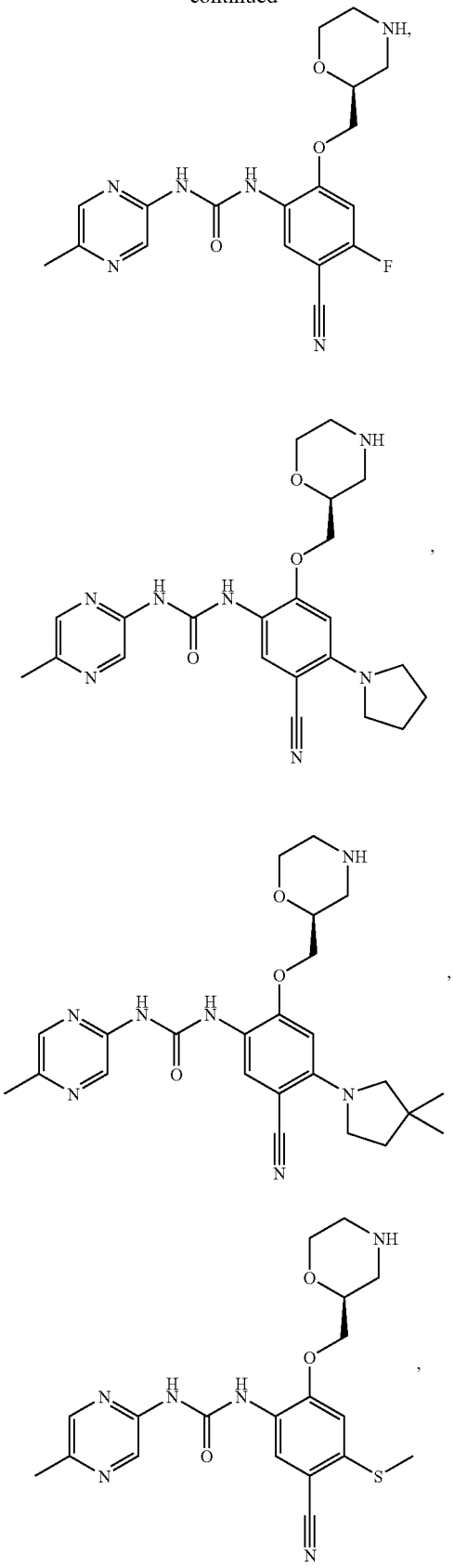

or mixtures thereof.

VI. Diarylurea Compounds Described in U.S. Provisional Patent Application No. 60/818,008, Filed Jun. 30, 2006

A Compound of Having a Formula (XII)

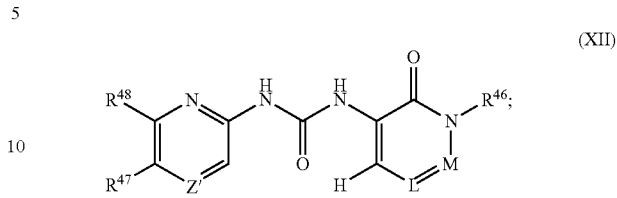

wherein L and M, independently, are N or C—$R^{49}$, with the proviso that at least one of L and M is C—$R^{49}$;

Z' is N or CH;

$R^{46}$ is selected from the group consisting of hydrogen, $C_{1-6}$alkyl optionally substituted with one or more of halo, hydroxy, CN, aryl, heteroaryl, heterocycloalkyl, $N(R^{50})_2$, $SR^{51}$, $SOR^{51}$, and $SO_2R^{51}$, $C_{2-6}$alkenyl, $C_{3-8}$cycloalkyl, aryl, beteroaryl, $C_{1-3}$alkyleneN$(R^{50})_2$, $C_{3-8}$heterocycloalkyl, and CH$(C_{1-3}$alkyleneN$(R^{50})_2)_2$;

$R^{47}$ and $R^{48}$, independently, are selected from the group consisting of hydrogen, halo, $OR^{50}$, $C_{1-6}$alkyl, $C_{2-6}$alkenyl, $C_{2-6}$alkynyl, $N(R^{50})_2$, $C(O)(R^{50})$, aryl$C_{1-3}$alkyl, $CF_3$, CN, $NO_2$, $CO_2R^{51}$, $COR^{51}$, $OC_{1-3}$alkylene$C_{3-8}$heterocycloalkyl, $OC_{1-3}$alkyleneN$(R^{50})_2$, $SR^{51}$, $SOR^{51}$, and $SO_2R^{51}$;

each $R^{49}$ is independently selected from the group consisting of hydrogen, halo, $C_{1-6}$alkyl, $C_{2-6}$alkenyl, $C_{2-6}$alkynyl, $OCF_3$, $CF_3$, $NO_2$, CN, NC, $N(R^{50})_2$, $OR^{50}$, $C(O)N(R^{50})_2$, $C(O)R^{50}$, $N(R^{50})COR^{50}$, $N(R^{50})C(O)OR^{50}$, $SO_2C_{1-6}$alkyl, $N(R^{50})C(O)C_{1-3}$alkylene(O)$R^{50}$, $N(R^{50})C(O)C_{1-3}$alkyleneC(O)$R^{50}$, $N(R^{50})C(O)C_{1-3}$alkyleneNHC(O)OR$^{50}$, $N(R)C(O)C_{1-3}$alkyleneSO$_2$NR$^{50}$, $C_{1-3}$alkyleneN$(R^{50})_2$, $OC_{1-3}$alkyleneN$(R^{50})_2$, $C_{1-3}$alkyleneOR$^{50}$, and $SR^{51}$;

each $R^{50}$ is independently selected from hydrogen, $C_{1-6}$alkyl, $C_{2-6}$alkenyl, $C_{2-6}$alkynyl, $C_{3-8}$cycloalkyl, aryl, heteroaryl, $SR^{51}$, $SOR^{51}$, and $SO_2R^{51}$, and $C_{1-3}$alkylenearyl, or two $R^{50}$ groups are taken together to form an optionally substituted 3- to 6-membered ring; and each $R^{51}$ is independently selected from hydrogen, $C_{1-6}$alkyl, $C_{2-6}$alkenyl, aryl, aryl$C_{1-3}$alkyl, $C_{3-8}$cycloalkyl, and $C_{1-3}$alkyleneC$_{3-8}$cycloalkyl, or a pharmaceutically acceptable salt, prodrug, or solvate thereof In one specific embodiment, one of $R^{47}$ and $R^{48}$ is hydrogen and the other is different from hydrogen.

Specific compounds of the present invention are those wherein Z' is N; L and M are C—$R^{49}$; $R^{49}$ is a hydrogen, halo, or $C_{1-6}$alkyl; $R^{47}$ is hydrogen, $C_{1-6}$alkyl, or $C_{1-3}$alkyleneN$(R^b)_2$; and, in more specific embodiments, one of $R^{47}$ and $R^{48}$ is hydrogen and the other is $C_{1-6}$alkyl, OC$_{1-3}$alkyleneN$(R^{50})_2$, or CN.

Specific compounds envisioned in this category include:

1-(5-methyl-2-oxo-1,2-dihydro-pyridin-3-yl)-3-(5-methyl-pyrazin-2-yl)-urea;

1-(5-cyano-pyrazin-2-yl)-3-(5-methyl-2-oxo-1,2-dihydro-pyridin-3-yl)-urea;

1-[6-(2-dimethylamino-ethoxy)-pyrazin-2-yl]-3-(5-methyl-2-oxo-1,2-dihydro-pyridin-3-yl)-urea;

1-(1,5-dimethyl-2-oxo-1,2-dibydro-pyridin-3-yl)-3-(5-methyl-pyrazin-2-yl)-urea;

1-(5-cyano-pyrazin-2-yl)-3-(1,5-dimethyl-2-oxo-1,2-dihydro-pyridin-3-yl)-urea;

1,[6-(2-dimethylamino-ethoxy)-pyrazin-2-yl]-3-(1,5-dimethyl-2-oxo-1,2-dihydro-pyridin-3-yl)-urea;

1-(5-chloro-2-oxo-1,2-dihydro-pyridin-3-yl)-3-(5-methyl-pyrazin-2-yl)-urea;

1-(5-chloro-2-oxo-1,2-dihydro-pyridin-3-yl)-3-(5-cyano-pyrazin-2-yl)-urea;

1-(5-chloro-2-oxo-1,2-dihydro-pyridin-3-yl)-3-[6-(2-dimethylamino-ethoxy)-pyrazin-2-yl]-urea;

1-(5-chloro-1-methyl-2-oxo-1,2-dihydro-pyridin-3-yl)-3-(5-methyl-pyrazin-2-yl)-urea;

1-(5-chloro-1-methyl-2-oxo-1,2-dihydro-pyridin-3-yl)-3-(5-cyano-pyrazin-2-yl)-urea;

1-(5-chloro-1-methyl-2-oxo-1,2-dihydro-pyridin-3-yl)-3-[6-(2-dimethylamino-ethoxy)-pyrazin-2-yl]-urea;

1-[1-(2-amino-ethyl)-5-methyl-2-oxo-1,2-dihydro-pyridin-3-yl]-3-(5-methyl-pyrazin-2-yl)-urea;

1-[1-(2-amino-ethyl)-5-methyl-2-oxo-1,2-dibydro-pyridin-3-yl]-3-(5-cyano-pyrazin-2-yl)-urea;

1-[1-(3-amino-propyl)-5-methyl-2-oxo-1,2-dihydro-pyridin-3-yl]-3-(5-methyl-pyrazin-2-yl)-urea;

1-[1-(3-amino-propyl)-5-methyl-2-oxo-1,2-dihydro-pyridin-3-yl]-3-(5-cyano-pyrazin-2-yl)-urea; and mixtures thereof, or pharmaceutically acceptable salts, prodrugs, hydrates, or solvates thereof.

The following compounds as shown in VII.-XI. (formulae XIII-XVIII) are described in terms of X, Y, Z, R, and the like, using similar terminology as those compounds as described above. However, the following X, Y, Z, R, and like terms are specific to each class of compounds separated by a Roman numeral designation, and are not to be inferred to correspond to a similarly termed X, Y, Z, R, and the like above.

VII. Urea Compounds Described in U.S. Patent Publication No. 2004/0014765

A Compound of Formula (XIII)

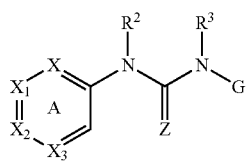

(XIII)

$X$ is $CR^1$; $X_1$-$X_3$ are CH; Z is O;

Ring A is optionally substituted at any substitutable carbon by $R^4$; $R^1$ is V-T-$R^6$;

T is a $C_{2-4}$ alkylidene chain;

V is —O—; $R^2$ and $R^3$ are each hydrogen; each $R^4$ is independently selected from halo, —OR, —SR, —CN, —$NO_2$, —N($R^5$)$_2$, —N($R^5$)C(O)R, —N($R^5$)$CO_2$R, —N($R^5$)C(O)N($R^5$)$_2$, —C(O)N($R^5$)$_2$, —OC(O)N($R^5$)$_2$, —$CO_2$R, —$SO_2$R, —S(O)R, —$SO_2$N($R^5$)$_2$, —N($R^5$)$SO_2$R, or an optionally substituted group selected from $C_{1-8}$ aliphatic, aryl, aralkyl, heterocyclyl, heterocycloalkyl, heteroaryl, or heteroaralkyl, or two ortho $R^4$s, taken together with the ortho carbon atoms to which they are bonded, form an optionally substituted five or six membered phenyl, pyridyl or heterocyclyl fused to Ring A;

each $R^8$ is independently a $C_{1-3}$ alkyl or, taken together with the nitrogen atom to which they are bonded, a 5-7 membered nitrogen containing heterocycle;

G is

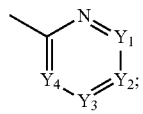

$Y_{1-4}$ are each independently selected from CH or nitrogen, provided that Ring B has no more than three nitrogen atoms and $Y_1$ and $Y_2$ are not both N, said Ring B being optionally substituted by $C_{1-4}$ aliphatic or haloaliphatic, $OR^7$, —$SR^7$, —C(O)$R^7$, —$CO_2R^7$, —$SO_2R^7$, —CN, —C(O)N($R^7$)$_2$, —N($R^7$)C(O)($C_{1-2}$ alkyl), or —N($R^7$)$_2$; each $R^7$ is independently selected from hydrogen or an optionally substituted $C_{1-3}$ aliphatic or —N($R^7$)$_2$ is a nitrogen-containing heterocyclyl; and each R is hydrogen.

VIII. Urea Compounds Described in WO 03/101444

(i) A Compound of Formula (XIV)

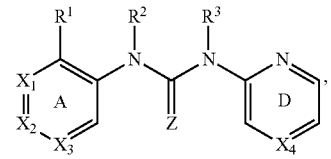

(XIV)

or a pharmaceutically acceptable salt thereof, wherein:

$X_1$-$X_3$ are independently CH or N, that provided that $X_1$-$X_3$ are not all N;

$X_4$ is CH or N; Z is O, S, or N—CN; Ring A is optionally substituted at any substitutable carbon by $R^4$;

$R^1$ is -T-$NH_2$, —V-T-$NH_2$, -T-$NHR^x$, —V-T-$NHR^x$; T is a $C_{1-6}$ straight or branched alkylidene chain that is optionally interrupted by —O—, —S—, —N($R^5$)—, —S(O)—, —$SO_2$—, —C(O)—, —OC(O)—, —N($R^5$)C(O)—, —C(O)N($R^5$)—, —$SO_2$N($R^5$)—, or —N($R^5$)$SO_2$—, wherein the alkylidene chain or a portion thereof is optionally part of a 3-6 membered ring system; V is —O—, —S—, —N($R^5$)—, —S(O)—, —$SO_2$—, —C(O)—, —OC(O)—, —N($R^5$)C(O)—, —C(O)N($R^5$)—, —$SO_2$N($R^5$)—, or —N($R^5$)$SO_2$—;

$R^2$ and $R^3$ are each independently selected from hydrogen, $C_{1-6}$ alkyl optionally substituted with —N($R^8$)$_2$, —C(=O)R, —$CO_2$R, or $SO_2$R, or $R_2$ and $R_3$ taken together with their intervening atoms form an optionally substituted an optionally substituted 5-6 membered ring; each $R^4$ is independently selected from halo, —OR, —SR, —CN, —$NO_2$, —N($R^5$)$_2$, —N($R^5$)C(O)R, —N($R^5$)$CO_2$R, —N($R^5$) C(O)N($R^5$)$_2$, —C(O)N($R^5$)$_2$, —C(O)$R^5$, —OC(O)N($R^5$)$_2$, —$CO_2$R, —$SO_2$R, —S(O)R, —$SO_2$N($R^5$)$_2$, —N($R^5$) $SO_2$R, or an optionally substituted group selected from $C_{1-8}$ aliphatic, aryl, aralkyl, heterocyclyl, heterocycloalkyl, heteroaryl, or heteroaralkyl, or two ortho $R^4$s, taken together with the ortho carbon atoms to which they are bonded, form an optionally substituted five or six membered phenyl, pyridyl or heterocyclyl fused to Ring A; each $R^5$ is independently selected from hydrogen, $C_{1-6}$ aliphatic, —$CO_2$R, —$SO_2$R, or —C(O)R, or two $R^5$ on the same nitrogen taken together with the nitrogen form a 5-8 membered heteroaryl or heterocycle ring having 1-4 heteroatoms selected from N, O, or S;

each $R^8$ is independently a $C_{1-3}$ alkyl or, taken together with the nitrogen atom to which they are bonded, a 5-7 membered nitrogen containing heterocycle;

Ring D is optionally substituted by $C_{1-4}$ aliphatic or haloaliphatic, $-OR^7$, $-SR^7$, $-C(O)R^7$, $-CO_2R^7$, $-SO_2R^7$, $-CN$, $-C(O)N(R^7)_2$, $-N(R^7)C(O)(C_{1-2}$ alkyl), or $-N(R^7)_2$ and is optionally fused to an optionally substituted phenyl or optionally substituted cyclohexyl ring;

each $R^7$ is independently selected from hydrogen or an optionally substituted $C_{1-3}$ aliphatic or $-N(R^7)_2$ is a nitrogen-containing heterocyclyl;

each R is independently selected from hydrogen or an optionally substituted group selected from $C_{1-6}$ aliphatic, aryl, aralkyl, heteroaryl, or heteroaralkyl-butyl; and $R^x$ is $C_1$-$C_8$ alkyl.

ii) A Compound of Formula (XV):

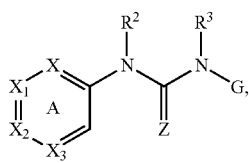

(XV)

or a pharmaceutically acceptable salt thereof, wherein: X is $CR^1$; $X_1$-$X_3$ are CH; Z is O; Ring A is optionally substituted at any substitutable carbon by $R^4$;

$R^1$ is V-T-$R^6$; T is a $C_{2-4}$ alkylidene chain; V is $-O-$;

$R^2$ and $R^3$ are each hydrogen;

each $R^4$ is independently selected from halo, $-OR$, $-SR$, $-CN$, $-NO_2$, $-N(R^5)_2$, $-N(R^5)C(O)R$, $-N(R^5)CO_2R$, $-N(R^5)C(O)N(R^5)_2$, $-C(O)N(R^5)_2$, $-OC(O)N(R^5)_2$, $-CO_2R$, $-SO_2R$, $-S(O)R$, $-SO_2N(R^5)_2$, $-N(R^5)SO_2R$, or an optionally substituted group selected from $C_{1-8}$ aliphatic, aryl, aralkyl, heterocyclyl, heterocycloalkyl, heteroaryl, or heteroaralkyl, or two ortho $R^4$s, taken together with the ortho carbon atoms to which they are bonded, form an optionally substituted five- or six-membered phenyl, pyridyl or heterocyclyl fused to Ring A;

each $R^5$ is independently selected from hydrogen, $C_{1-6}$ aliphatic, $CO_2R$, $-SO_2R$, or $-C(O)R$, or two $R^5$s on the same nitrogen taken together with the nitrogen form a 5-8 membered heteroaryl or heterocycle ring having 1-4 heteroatoms selected from N, O, or S;

$R^6-NH_2$;

each $R^8$ is independently a $C_{1-3}$ alkyl or, taken together with the nitrogen atom to which they are bounded, a 5-7 membered nitrogen containing heterocycle;

G is

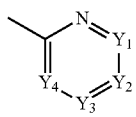

$Y_{1-4}$ are each independently selected from CH or nitrogen, provided that Ring B has no more than three nitrogen atoms and $Y_1$ and $Y_2$ are not both N, said Ring B being optionally substituted by $C_{1-4}$ aliphatic or haloaliphatic, $-OR^7$, $-SR^7$, $-C(O)R^7$, $-CO_2R^7$, $-SO_2R^7$, $-CN$, $-C(O)N(R^7)_2$, $-N(R^7)C(O)(C_{1-2}$ alkyl), or $-N(R^7)_2$;

each $R^7$ is independently selected from hydrogen or an optionally substituted $C_{1-3}$ aliphatic or $-N(R^7)_2$ is a nitrogen-containing heterocyclyl; and each R is hydrogen.

IX. Urea Compounds Described in U.S. Pat. No. 7,056,925
A Compound for Formula (XVI)

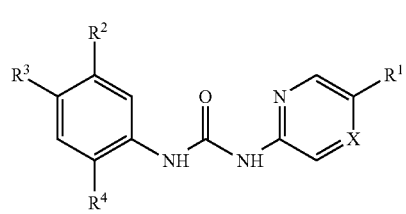

(XVI)

or a therapeutically acceptable salt thereof, wherein
X is $-N-$ or $-CH-$;

$R^1$ is selected from the group consisting of hydrogen, alkoxy, alkyl, amino, carboxy, cyano, halo, hydroxy, and hydroxyalkyl;

$R^2$ is selected from the group consisting of alkoxy, alkyl, alkylcarbonyl, amino, cyano, halo, and nitro;

$R^3$ is selected from the group consisting of hydrogen, alkoxy, alkyl, amino, aminoalkyl, aminocarbonyl, arylalkyl, cyano, nitro, $-CO_2R^5$, $-COR^5$, and $-SR^5$;

$R^4$ is selected from the group consisting of $-(CHR^6)_mOR^7$, and $-(CH_2)_nNR^8R^9$;

$R^5$ is selected from the group consisting of hydrogen, alkenyl, alkyl, aryl, arylalkyl, cycloalkyl, and (cycloalkyl)alkyl;

$R^6$ is selected from the group consisting of hydrogen, alkyl, aryl, and heteroaryl;

$R^7$ is selected from the group consisting of hydrogen, alkenyl, alkoxyalkoxyalkyl, alkoxyalkyl, alkoxycarbonylalkyl, alkylsulfanylalkyl, alkynyl, aminoalkyl, arylalkyl, arylcarbonylalkyl, aryloxyalkyl, arylsulfanylalkyl, cycloalkenyl, (cycloalkenyl)alkyl, cycloalkyl, (cycloalkyl)alkyl, heteroarylalkoxyalkyl, heteroarylalkyl, (heterocyclyl)alkoxyalkyl, (heterocyclyl)alkyl, and hydroxyalkyl;

$R^8$ and $R^9$ are independently selected from the group consisting of hydrogen, alkenyl, alkoxyalkyl, alkyl, alkylsulfanylalkyl, alkynyl, aminoalkyl, arylalkyl, cycloalkenyl, (cycloalkenyl)alkyl, cycloalkyl, (cycloalkyl)alkyl, heteroarylalkyl, (heterocyclyl)alkyl, and hydroxyalkyl;

m is 0-6; provided that when $R^7$ is hydrogen m is other than 0; and n is 0-6; provided that when $R^8$ and $R^9$ are both hydrogen, n is other than 0.

X. Urea Compounds Described in International Patent Publication No. WO 06/072589
A Compound of Formula (XVII)

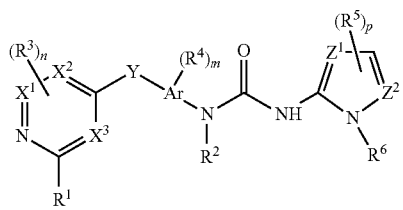

(XVII)

wherein
$R^1$ is hydrogen, or unsubstituted or substituted alkyl, halogen, hydroxy, esterified or etherified hydroxy, amino, substituted amino, carboxy, esterified carboxy, carbamoyl, N-mono- or N,N-disubstituted carbamoyl;

$R^2$ is unsubstituted or substituted alkyl, unsubstituted or substituted aryl, unsubstituted or substituted heterocyclyl or unsubstituted or substituted cycloalkyl, n is 0, 1, 2 or 3; m is 0, 1, 2 or 3; p is 0, 1, 2 or 3;

each of $R^3$ and $R^4$, if present and independently of the others, is unsubstituted or substituted alkyl, halogen, hydroxy, esterified or etherified hydroxy, mercapto, substituted mercapto, nitro, amino, substituted amino, carboxy, esterified carboxy, carbamoyl, N-mono- or N,N-disubstituted carbamoyl, sulfo, esterified sulfo, sulfamoyl, N-mono- or N,N-disubstituted sulfamoyl or cyano;

$R^5$, independently of $R^3$ and $R^4$, is unsubstituted or substituted alkyl, unsubstituted or substituted aryl, unsubstituted or substituted heterocyclyl or unsubstituted or substituted cycloalkyl, halogen, hydroxy, esterified or etherified hydroxy, mercapto, substituted mercapto, nitro, amino, substituted amino, carboxy, esterified carboxy, carbamoyl, N-mono- or N,N-disubstituted carbamoyl, sulfo, esterified sulfo, sulfamoyl, N-mono- or N,N-disubstituted sulfamoyl or cyano; R6 is unsubstituted or substituted alkyl, unsubstituted or substituted aryl, unsubstituted or substituted heterocyclyl or unsubstituted or substituted cycloalkyl;

each of $X^1$, $X^2$ and $X^3$, independently of the others, is N or CH;

Y is oxy (—O—), imino (—NH—), thio (—S—) or methylene (—CH$_2$—) and

Ar is arylene or heterocyclylene; and each of $Z^1$ and $Z^2$, independently of the other, is nitrogen (N) or CH, with the proviso that at least one of $Z^1$ and $Z^2$ is N; or (preferably pharmaceutically acceptable) salts thereof.

XI. Macrocyclic Urea Compounds Described in International Patent Publication No. WO 05/215556

A Compound of Formula (XVIII)

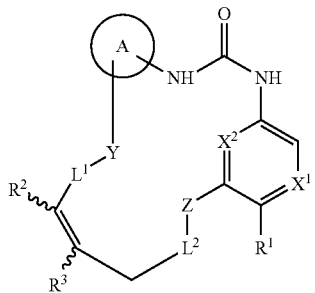

(XVIII)

wherein the dashed line indicates an optional bond;

A is selected from the group consisting of aryl and heteroaryl, wherein the aryl and the heteroaryl are optionally substituted with one, two, or three substituents independently selected from the group consisting of alkoxy, alkoxyalkoxy, alkoxyalkoxyalkoxy, alkyl, cyano, halo, haloalkylsulfonyloxy, haloalkoxy, heteroarylalkoxy, heterocycle, heterocycloalkoxy, heterocyclooxyalkoxy, heterocyclooxyalkyl, heterocyclooxyalkynyl, heteroarylcarbonylalkoxy, haloalkyl, hydroxyalkenyl, hydroxyalkoxy, hydroxyalkyl, hydroxyalkynyl, hydroxy, nitro, $NR^aR^b$, $(NR^aR^b)$alkoxy, $(NR^aR^b)$alkyl, and $(NR^aR^b)$alkynyl;

$R^1$ is selected from the group consisting of hydrogen, alkoxycarbonyl, alkyl, carboxy, cyano, halo, and nitro;

$R^2$ and $R^3$ are independently selected from the group consisting of hydrogen, alkoxy, alkoxycarbonyl, alkyl, alkylsulfonyl, arylsulfonyl, halo, hydroxy, and $NR^aR^b$; or $R^2$ and $R^3$, together with the atoms to which they are attached, form an epoxide;

$X^1$ and $X^2$ are independently selected from the group consisting of CH and N;

Y and Z are independently selected from the group consisting of CH$_2$, O, and NR$^z$, wherein R$^z$ is selected from the group consisting of hydrogen and alkyl;

$L^1$ and $L^2$ are independently selected from the group consisting of a bond and alkylene;

$R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl, and $(NR^cR^d)$alkylcarbonyl; and $R^c$ and $R^d$ are independently selected from the group consisting of hydrogen, alkyl, and cycloalkyl.

As used herein, the term "alkyl" means straight chained and branched hydrocarbon groups containing the indicated number of carbon atoms, typically methyl, ethyl, and straight chain and branched propyl and butyl groups. Unless otherwise indicated, the hydrocarbon group can contain up to 20 carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, aryl, heteroaryl, cycloalkyl, heterocycloalkyl, amino, and sulfonyl.

The term "cycloalkyl" means a cyclic $C_{3-8}$hydrocarbon group, e.g., cyclopropyl, cyclobutyl, cyclohexyl, or cyclopentyl. "Heterocycloalkyl" is defined similarly as cycloalkyl, except the ring contains one to three heteroatoms independently selected from the group consisting of oxygen, nitrogen, and sulfur. Cycloalkyl and heterocycloalkyl groups can be saturated or partially unsaturated ring systems optionally substituted with, for example, one to three groups, independently selected from the group consisting of $C_{1-4}$alkyl, $C_{1-3}$alkyleneOH, C(O)NH$_2$, NH$_2$, oxo (=O), aryl, trifluoroethanoyl, and OH. Heterocycloalkyl groups optionally can be further N-substituted with $C_{1-6}$alkyl, hydroxy$C_{1-6}$alkyl, $C_{1-3}$alkylenearyl, or $C_{1-3}$alkyleneheteroaryl.

The term "alkenyl" is defined identically as "alkyl," except the group contains a carbon-carbon double bond.

The term "alkynyl" is defined identically as "alkyl," except the group contains a carbon-carbon triple bond.

The term "alkylene" means an alkyl group having a substituent. For example, the term "$C_{1-6}$alkyleneC(O)OR" refers to an alkyl group containing one to six carbon atoms substituted with a —C(O)OR group. The alkylene group is optionally substituted with one or more substituent previously listed as an optional alkyl substituent.

The term "halo" or "halogen" means fluorine, bromine, chlorine, and iodine.

The term "aryl," alone or in combination, means a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, $C_{1-6}$alkyl, $C_{2-6}$alkenyl, OCF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O)OR$^3$, N(R$^1$)C(O)OR$^3$, N(R$^1$)C(O)C$_{1-3}$alkyleneC(O)R$^3$, N(R$^1$)C(O)C$_{1-3}$alkyleneC(O)OR$^3$, N(R$^1$)C(O)C$_{1-3}$alkyleneOR$^3$, N(R$^1$)C(O)C$_{1-3}$alkyleneNHC(O)OR$^3$, N(R$^1$)C(O)C$_{1-3}$alkyleneSO$_2$NR$^3$, $C_{1-3}$alkyleneOR$^1$, and SR$^3$, wherein R$^1$ and $R^3$ are as previously defined. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. The terms "aryl$C_{1-3}$alkyl" and "heteroaryl$C_{1-3}$alkyl" means an aryl or heteroaryl group having a $C_{1-3}$alkyl substituent.

The term "heteroaryl" means a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, $C_{1-6}$alkyl, aryl, heteroaryl, $CF_3$, CN, $C(O)N(R^3)_2$, $CO_2R^2$, $N(R^3)_2$, $OR^3$, and halo, wherein $R^3$ is as previously defined. Examples of heteroaryl groups include, but are not limited to, thienyl, furyl, pyridyl, oxazolyl, quinolyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "hydro" is —H.
The term "hydroxy" is —OH.
The term "nitro" is —$NO_2$.
The term "cyano" is —CN.
The term "trifluoromethoxy" —$OCF_3$.
The term "azido" is defined as —$N_3$.
The term "3- to 8-membered ring" means carbocyclic and heterocyclic aliphatic or aromatic groups, including, but not limited to, morpholinyl, piperidinyl, phenyl, thiophenyl, furyl, pyrrolyl, imidazolyl, pyrimidinyl, and pyridinyl, optionally substituted with one or more, and in particular one to three, groups exemplified above for aryl groups.

The carbon atom content of hydrocarbon-containing moieties is indicated by a subscript designating the minimum and maximum number of carbon atoms in the moiety, e.g., "$C_{1-6}$alkyl" refers to an alkyl group having one to six carbon atoms, inclusive.

Prodrugs of compounds disclosed herein also can be used as the compound in compositions of the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, 1985; R. B. Silverman, "The Organic Chemistry of Drug Design and Drug Action," Academic Press, San Diego, chapter 8, 1992; K. M. Hillgren et al., *Med. Res. Rev.*, 15:83 (1995).)

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds used in the compositions disclosed herein can exist as their free base or as pharmaceutically acceptable salts. As used herein, the term "pharmaceutically acceptable salts" refers to salts or zwitterionic forms of the compounds a described above. Salts of such compounds can be prepared during the final isolation and purification of the compounds or separately by reacting the compound with an acid having a suitable cation. Suitable pharmaceutically acceptable cations include alkali metal (e.g., sodium or potassium) and alkaline earth metal (e.g., calcium or magnesium) cations. In addition, the pharmaceutically acceptable salts of the disclosed Chk1 inhibitor compounds that contain a basic center are acid addition salts formed with pharmaceutically acceptable acids.

Examples of acids which can be employed to form pharmaceutically acceptable salts include inorganic acids such as hydrochloric, hydrobromic, sulfuric, and phosphoric, and organic acids such as oxalic, maleic, succinic, malonic, and citric. Nonlimiting examples of salts of compounds of the invention include, but are not limited to, hydrochloride, hydrobromide, hydroiodide, sulfate, bisulfate, 2-hydroxyethansulfonate, phosphate, hydrogen phosphate, acetate, adipate, alginate, aspartate, benzoate, butyrate, camphorate, camphorsulfonate, citrate, digluconate, glycerolphosphate, hemisulfate, heptanoate, hexanoate, formate, succinate, malonate, fumarate, maleate, methanesulfonate, mesitylenesulfonate, naphthylenesulfonate, nicotinate, oxalate, pamoate, pectinate, persulfate, 3-phenylpropionate, picrate, pivalate, propionate, trichloroacetate, trifluoroacetate, glutamate, bicarbonate, undecanoate, lactate, citrate, tartrate, gluconate, benzene sulphonate, and p-toluenesulphonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to Chk1 inhibitors appearing herein is intended to include compounds disclosed herein as well as pharmaceutically acceptable salts, solvates (e.g., hydrates), or prodrugs thereof.

Chk1 inhibitors can be conjugated or linked to auxiliary moieties to promote a property of the Chk1 inhibitor that may be beneficial in methods of therapeutic use. Such conjugates can enhance delivery of the Chk1 inhibitors to a particular anatomical site or region of interest (e.g., a tumor), enable sustained therapeutic concentrations of the inhibitor in target cells, alter pharmacokinetic and pharmacodynamic properties of the inhibitors, and/or improve the therapeutic index or safety profile of the inhibitors. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties to promote biodistribution or uptake of the compound by target cells (see, e.g., Bradley et al., *Clin. Cancer Res.* 7:3229 (2001)).

Cyclodextrins

The compositions disclosed herein also contain at least one cyclodextrin. Cyclodextrin is a cyclic structure of sugar units, typically having 6 (α-cyclodextrin), 7 (β-cyclodextrin), 8 (γ-cyclodextrin), or 9 (δ-cyclodextrin) sugar units in one cyclodextrin molecule. Also contemplated are cyclodextrins having 5, 10, 11, 12, 13, or more sugar units.

Cyclodextrins may be amorphous or crystalline. Cyclodextrins are commercially available, or may be synthesized via means well known in the art. Examples of useful cyclodextrins include, but are not limited to, modified or unmodified α-, β-, γ-, and δ-cyclodextrins. Derivatives of cyclodextrins include derivatives wherein some of the OH groups are converted to OR groups. Cyclodextrin derivatives include those with short chain alkyl groups such as methylated, ethylated, propylated, and butylated cyclodextrins, wherein R is a methyl, ethyl, propyl, or butyl group; those with hydroxyalkyl substituted groups, such as, e.g., hydroxypropyl cyclodextrins and/or hydroxyethyl cyclodextrins, wherein R is a —$CH_2CH(OH)CH_3$ or a —$CH_2CH_2OH$ group; branched cyclodextrins such as maltose-bonded cyclodextrins; cationic cyclodextrins such as those containing 2-hydroxy-3-(dimethylamino)propyl ether, wherein R is $CH_2CH(OH)CH_2N(CH_3)_2$; quaternary ammonium, e.g., 2-hydroxy-3-(trimethylammonio)propyl ether chloride groups, wherein R is $CH_2CH(OH)CH_2N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., mono-3-6-anhydrocyclodextrins, as disclosed in "Optimal Performances with Minimal Chemical Modification of Cyclodextrins", F. Diedaini-Pilard et al., *The 7th International Cyclodextrin Symposium Abstracts*, April 1994, p 49; and mixtures thereof. Other specific modifications contemplated include one or more hydroxyalkyl ether (e.g., R is $C_{1-6}$alkylenehydroxy) moieties; one or more sulfoalkyl ether (e.g., R is $C_{2-6}$alkyleneSO$_3^-$) moieties; carboxyalkyl (e.g., R is $C(O)C_{1-6}$alkyl) moieties; 6-perdeoxy-6-per(4-carboxyphenyl)thio moieties (Cooper et al., *Org. Biomol. Chem.*, 3:1863 (2005)); substituted phenoxy moieties, such as 6-O-phenyl, 6-O-(4-formylphenyl), 6-O-(4-nitrophenyl), 6-O-(4-bromophenyl), 6-O-(4-chlorophenyl), and 6-O-(4-hydroxybenzyl) (Liu et al., *J. Org. Chem.*, 69:173 (2004)); 6-amino-6-deoxy cyclodextrins (Rekharsky et al., *J. Am. Chem. Soc.*, 124:12361 (2002)); tryptophan moieties (Wang et al., *J. Org. Chem.* 70:8703 (2005)); or mixtures thereof.

Cyclodextrin derivatives suitable for use herein include hydroxypropyl α-cyclodextrin, methylated α-cyclodextrin, methylated β-cyclodextrin, hydroxyethyl β-cyclodextrin, and hydroxypropyl β-cyclodextrin. Hydroxyalkyl cyclodextrin derivatives preferably have a degree of substitution/modification of from about 1 to about 14, more preferably from about 1.5 to about 7, wherein the total number of OR groups per cyclodextrin is defined as the degree of substitution/modification. Methylated cyclodextrin derivatives typically have a degree of substitution/modification of from about 1 to about 18, preferably from about 3 to about 16. A known methylated β-cyclodextrin is heptakis-2,6-di-O-methyl-b-cyclodextrin, commonly known as DIMEB, in which each glucose unit has about 2 methyl groups with a degree of substitution of about 14. Another commercially available cyclodextrin which can be used in the disclosed compositions is methylated β-cyclodextrin, a randomly methylated β-cyclodextrin, commonly known as RAMEB, having different degrees of substitution, normally of about 12.6.

Other modified cyclodextrins are described, for example, in U.S. Pat. Nos. 3,426,011; 3,453,257; 3,453,258; 3,453,259; 3,453,260; 3,459,731; 3,453,257; 3,420,788; 3,426,011; 3,553,191; 3,565,887; 4,535,152; 4,616,008; 4,638,058; 4,678,598; 4,727,064; 4,746,734; 5,376,645; 5,134,127; 5,376,645; 5,602,112; 5,804,568; 5,824,668; 5,874,418; 6,046,177; 6,048,845; 6,133,248; 6,136,846; 6,218,374; 6,284,747; 6,509,370; 6,583,125; and 6,982,253, each incorporated by reference in its entirety herein.

Modified cyclodextrins particularly suitable include hydroxyalkylether cyclodextrins, such as hydroxypropylether, and sulfobutylether (SBE) cyclodextrins, such as SBE-1-β-cyclodextrin, SBE-4-β-cyclodextrin, and SBE-7-β-cyclodextrin, where the 1, 4, and 7 designations indicate the average degree of substitution/modification of the cyclodextrin (available from CyDex, Inc. of Overland Park, Kans. USA). A specific cyclodextrin is SBE-7 β-cyclodextrin, sold under the trademark CAPTISOL® (hereinafter "Captisol") by CyDex, Inc., Lenexa Kans., U.S.A.

As used herein, the term "degree of substitution/modification," as it relates to cyclodextrin derivatives, refers to the total number of OR groups per cyclodextrin molecule. It is understood that commercially available cyclodextrin derivatives actually contain individual cyclodextrin molecules having varying degrees of substitution/modification. For example, hydroxypropyl β-cyclodextrin having an average degree of substitution of 3 still contains an amount of non-derivatized β-cyclodextrin of about 5%, while hydroxypropyl β-cyclodextrin having an average degree of substitution of about 5 has an amount of non-derivatized beta-cyclodextrin of less than about 1%. The term "average degree of substitution/modification" thus relates to the average statistical distribution of individual substituted/modified cyclodextrin molecules of a given cyclodextrin derivative.

Cyclodextrins can complex with guest molecules, due in part to its cyclic molecular structure. The molecular structure can be analogized to that of a doughnut, e.g., a configuration, such as a truncated cone or cylinder, with a cavity or hole in its center. Without wishing to be bound by theory, the guest molecules to be complexed are trapped within the hole or cavity of the cyclodextrin molecules and/or are associated with the side chains of the cyclodextrin, off the "doughnut" core, and held there through some binding mechanism or mechanisms, such as electrostatic interactions or Van der Waals interactions. The size of the hole or cavity, both its diameter and depth, is influenced by the number of sugar units in the cyclodextrin molecule. For instance, γ-cyclodextrin has two more sugar units than α-cyclodextrin, which corresponds both to a larger diameter and to a greater number of possible sites for complexation. Additionally, for modified cyclodextrins, the number of modifications, as well as the chemical and/or physical properties of those modifications, can influence the possible number of complexation sites. To illustrate, the maximum number of guest molecules that can complex to unmodified γ-cyclodextrin is about 9, while the maximum number for unmodified β-cyclodextrin is about 8. With modified cyclodextrins, which can have complexation sites on the side chains of the cyclodextrin, the maximum number of guest molecules can change. Therefore, the maximum number of guest molecules that can complex to a particular cyclodextrin depends upon the number of sugar units of the cyclodextrin, the number and identity of any modification to the cyclodextrin, and the structure and/or size of the guest molecule.

As used herein, "complexation" refers to a non-covalent interaction between the Chk1 inhibitor (the "guest molecule") and the cyclodextrin. This interaction can occur within the cavity of the cyclodextrin, on a side chain of the cyclodextrin, or at both sites. The interaction between the Chk1 inhibitor and the cyclodextrin preferably is reversible to allow for de-complexation, or release, of the Chk1 inhibitor and delivery of the Chk1 inhibitor to the desired target, e.g., a serum protein, cancer cells, tumor, or the like.

The amount of cyclodextrin in a composition disclosed herein may be widely adjusted to achieve desired physical characteristics. Such characteristics include, but are not limited to: increased solubility of the Chk1 inhibitor; decreased toxicity of the Chk1 inhibitor to undesired targets; and/or increased stability of the Chk1 inhibitor in the composition. Therefore, the amount of cyclodextrin can be determined by an effect on one or more of the above-mentioned proprieties in the composition. Methods for measuring one or more such characteristics are within the level of skill possessed by the ordinary artisan and/or by methods described herein or incorporated by reference.

Typically, a Chk1 inhibitor is present in the composition in an amount from about 0.01% to about 50% by weight. In specific embodiments, the Chk1 is present in an amount from about 0.1% to about 20%, from about 0.1% to about 15%, or from about 0.1% to about 10% by weight. Specific weight percentages of Chk1 inhibitor present in a composition of the present invention include about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, and about 49% by weight.

The cyclodextrin is present in an amount of about 1% to about 90%, about 20% to about 80%, about 30% to about 80%, or about 40% to about 80% by weight. Specific weight percentages of cyclodextrin present in a composition of the present invention include about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, and about 90% by weight.

In some embodiments, the amount of Chk1 inhibitor to cyclodextrin in the composition is sufficient to provide a composition wherein at least about 50% by weight of the Chk1 inhibitor is complexed with the cyclodextrin. In various embodiments, greater than 60% by weight, greater than 75% by weight, greater than 90% by weight, and greater than 95% by weight of the Chk1 inhibitor is complexed with a cyclodextrin in the composition. Specific weight percentages of complexed Chk1 inhibitor to a cyclodextrin in the composition include greater than about 55%, greater than about 60%, greater than about 65%, greater than about 70%, greater than about 75%, greater than about 80%, greater than about 85%, greater than about 90%, greater than about 91%, greater than about 92%, greater than about 93%, greater than about 94%, greater than about 95%, greater than about 96%, greater than about 97%, greater than about 98%, and greater than about 99%, based on the total weight of Chk1 inhibitor in the composition. The amount of uncomplexed Chk1 inhibitor can be assessed by determination of the association constant ($K_a$), which can be measured via a variety of techniques known to those of skill in the art, including calorimetry experiments and solubility measurements.

The number of moles of at least one Chk1 inhibitor that complex to one mole of cyclodextrin in the compositions disclosed herein can be as great as the maximum number of complexation sites on the cyclodextrin. In some embodiments, the mole ratio of the at least one Chk1 inhibitor ranges from at least about 1:1 to at least about n:1, where n represents the total number of complexation sites of the cyclodextrin. Where more than one cyclodextrin is present in the composition, n may be taken to represent the average total number of complexation sites of the cyclodextrins present. As mentioned above, in some embodiments, the at least one Chk1 inhibitor comprises at least one disubstituted urea compound. In some embodiments, specific mole ratios of Chk1 inhibitor to cyclodextrin include up to about 9:1, up to about 8:1, up to about 7:1, up to about 6:1, up to about 5:1, up to about 4:1, up to about 3:1, up to about 2:1, and up to about 1:1. Other mole ratio ranges include from about 1:1 to about 5:1; from about 1:1 to about 4:1; from about 1:1 to about 3:1; and from about 1:1 to about 2:1. Further contemplated mole ratios of Chk1 inhibitor to cyclodextrin include about 1:2, about 1:3, and about 1:4.

Anticancer Agents

The compositions disclosed herein typically are administered in conjunction with an anticancer agent. In some embodiments, the anticancer agent is administered sequentially, either before or after the compositions disclosed herein, while in other embodiments, the anticancer agent is administered simultaneously, either separately or within the same composition as a Chk1 inhibitor.

"Anticancer agent" means any therapeutic agent that is capable of exhibiting efficacy at combating, ameliorating, or retarding a cancer, e.g., a chemotherapeutic agent, radiation, or both. In some embodiments, the anticancer agent is a Chk1 activator.

"Chk1 activator" means any agent, whether now known or after-discovered, whether naturally occurring or man-made, having an ability to sufficiently activate Chk1 kinase to induce a cell cycle arrest. An agent may be identified as a Chk1 activator for purposes of this invention by methods known in the art. In one non-limiting method, the phosphorylation state of Chk1 is measured as an indication of Chk1 activation. For example, the phosphorylation of Chk1 serines 317 and 345 has been shown to correlate with Chk1 activation after treatment with agents known to activate Chk1. Chk1 activators include those capable of arresting the cell cycle at a specific phase of the cell cycle, which phase may be referred to herein as the "target phase" for that activator. Target phases include any of the cell cycle phases except mitosis. Thus, in some embodiments, the Chk1 activator will induce cell cycle arrest at the G1 phase. In other embodiments, the Chk1 activator will induce cell cycle arrest at the S phase. In still other embodiments, the Chk1 activator will induce cell cycle arrest at the G2 phase.

The proportion of cells in different phases of the cell cycle can be measured by those skilled in the art using any one of a variety of techniques. For example, a fluorescent DNA-binding dye, propidium iodide, can be used to distinguish cells in different cell cycle phases. Since cells in G2 have twice as much DNA as cells in G1, and S phase cells show an intermediate amount of DNA, the technique allows one to identify cells in different phases based on the DNA content of a cell. This method can be carried out on cell lines and tumor specimens (Cerra et al., *Methods in Cell Biology*, 33:1 (1990)) Furthermore, cells in S phase can be labeled with the nucleotide analog, bromo-deoxyuridine (BrdU), then fixed and stained with a fluorescent-tagged antibody to BrdU. Both of these methods employ fluorescence cytometry or fluorescence activity cell sorting (FACS) to quantify the proportion of cells staining with these fluorescent markers.

An additional method for identification of cells in different phases of the cell cycle includes staining the cells with antibodies to markers that are either specific or selective for cell cycle phases. An antibody to the phosphorylated serine 10 residue of histone H3 is highly selective for mitotic cells. An antibody to phosphorylated serine 795 of the retinoblastoma protein, Rb, is selective for S phase cells (Connell-Crowley et al., *Mol. Biol. Cell*, 8:287 (1997)). Staining of cells with these antibodies can be used to quantify the proportion of cells in these cell cycle phases by immunohistochemistry or western blot analysis.

Another method for identification of cells in different phases of the cell cycle includes radioisotope labeling. For example, the ability of gemcitabine to arrest tumor cells in S phase may be assessed in multiple tumor types. Gandhi et al, *J. Clin. Oncol.*, 20:665 (2002) discloses a method for assessing S phase arrest in acute myelogenous leukemia patients after treatment with gemcitabine. Patients received gemcitabine at a constant dose of 10/mg/m$^2$/min for various durations of time and tumor cells isolated from blood of patients 24 hours after the start of therapy to determine the number of cells in S phase arrest. Cells may be plated in triplicate (2×10$^6$) in RPMI-1640/10% Fetal bovine serum and 1 µCi of [$^3$H]thymidine. Cells may then be allowed to incubate for 30 minutes, after which time thymidine incorporation may be measured. A decrease in radioisotope uptake after treatment with Chk1 activator indicates whether the cells are arrested in S phase, and the duration of the S phase arrest.

Any chemotherapeutic agent, known or after-discovered, can be used in the methods of the present invention. Any radiotherapeutic agent, known or after-discovered, also can be used in the methods of the present invention. The selection of a suitable anticancer agent is within the level of skill of the ordinarily skilled artisan. Factors used in the selection will depend, for example, upon the condition being treated, the cell type of aberrantly proliferating cells targeted, whether such cells are to be exposed to the anticancer agent in vivo or ex vivo, the recipient's health, and other factors which are known to those of ordinary skill in the art. Available anticancer agents can be adapted for use in the control of any aberrantly proliferating cell type or the conditions listed herein. For example, when the method is used to treat non-cancerous aberrantly proliferating cells, lower levels typically will be used than when treating cancerous aberrantly proliferating cells. For example, levels of radiation, e.g., ultraviolet (UV) radiation, and/or low levels of suitable chemotherapeutic agents (e.g., methotrexate) may be used in the control of aberrantly proliferating cells according to the invention.

"Inhibiting aberrant cell proliferation" means retarding the rate at which aberrantly proliferating cells proliferate or eliminating such proliferation altogether. This inhibition can result either from a decreased rate of replication, an increased rate of cell death, or both. Cell death can occur by any mechanism, including apoptosis and mitotic.

"Preventing aberrant cell proliferation" means inhibiting aberrant cell proliferation prior to occurrence, or inhibiting the recurrence thereof.

"In vivo" means within a living subject, as within an animal or human. In this context, agents can be used therapeutically in vivo to retard or eliminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples, such as fluid or tissue samples from humans or animals. Such samples can be obtained by methods well known in the art. Exemplary biological fluid samples include blood, cerebrospinal fluid, urine, and saliva. Exemplary tissue samples include tumors and biopsies thereof. In this context, the present formulations can be in numerous applications, both therapeutic and experimental.

"Radiosensitizer" means a compound administered to a human or other animal in a therapeutically effective amount to increase the sensitivity of cells to electromagnetic radiation and/or to promote the treatment of diseases treatable with electromagnetic radiation.

"Radiation" includes, but is not limited to, radiation having the wavelength of 10$^{-20}$ to 100 meters.

Examples of chemotherapeutic agents useful in the present invention include, but are not limited to:

alkylating agents, such as nitrogen mustards (e.g., mechlorethamine, cyclophosphamide, ifosfamide, melphalan, and chlorambucil); nitrosoureas (e.g., carmustine (BiCNU®), lomustine (CCNU), and semustine (methyl-CCNU)); ethylenimines and methyl-melamines (e.g., triethylenemelamine (TEM), triethylene thiophosphoramide (thiotepa), and hexamethylmelamine (Hexalen®)); alkyl sulfonates (e.g., bisulfan); and triazines (e.g., dacarbazine (DTIC®));

antimetabolites, such as folic acid analogs (e.g., methotrexate, trimetrexate, and pemetrexed (Alimta®)); pyrimidine analogs (such as 5-fluorouracil (5-FU), fluorodeoxyuridine, gemcitabine, cytosine arabinoside (AraC, cytarabine), 5-azacytidine, and 2,2'-difluorodeoxycytidine); and purine analogs (e.g., 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA));

type I topoisomerase inhibitors, such as camptothecin (CPT), topotecan, and irinotecan;

Biological response modifiers, such as G-CSF and GM-CSF;

Differentiation agents, such as retinoic acid derivatives;

Hormones and antagonists, such as Adrenocorticosteroids/antagonists (e.g., prednisone and equivalents, dexamethasone, aminoglutethimide); Progesfins (e.g., hydroxyprogesterone caproate, medroxyprogesterone acetate, megestrol acetate); Estrogens (e.g., diethylstilbestrol, ethynyl estradiol/equivalents); Antiestrogens (e.g., tamoxifen); Androgens (e.g., testosterone propionate, fluoxymesterone/equivalents); Antiandrogens (e.g., flutamide, gonadotropin-releasing hormone analogs, leuprolide); and Nonsteroidal antiandrogens (e.g., Flutamide);

Natural products such as Antimitotic drugs (e.g., Taxanes, paclitaxel, Vinca alkaloids, vinblastine (VLB), vincristine, vinorelbine, Taxotere® (docetaxel), estramustine, estramustine phosphate); Epipodophylotoxins (e.g., etoposide, teniposide); Antibiotics (e.g., actinomycin D, daunomycin (rubidomycin), doxorubicin (adriamycin), mitoxantrone, idarubicin, bleomycin, splicamycin (mithramycin), mitomycinC, dactinomycin and aphidicolin); Enzymes (e.g., L-asparaginase and L-arginase); Radiosensitizers (e.g., metronidazole, misonidazole, desmetbylmisonidazole, pimonidazole, etanidazole, nimorazole, RSU 1069, EO9, RB 6145, SR4233, nicotinamide, 5-bromodeozyuridine, 5-iododeoxyuridine, bromodeoxycytidine);

platinum coordination complexes, such as cisplatin, carboplatin, oxaliplatin, anthracenedione and mitoxantrone;

substituted ureas, such as hydroxyurea; and methylhydrazine derivatives, such as N-methylhydrazine (MIH) and procarbazine;

Adrenocortical suppressant, such as mitotane (o,p'-DDD) and ainoglutethimide;

Cytokines, such as interferon ($\alpha$, $\beta$, $\gamma$) and interleukin-2; and Photosensitizers, such as hematoporphyrin derivatives, Photofrin®, benzoporphyrin derivatives, Npe6, tin etioporphyrin (SnET2), pheoboride-a, bacteriochlorophyll-a, naphthalocyanines, phthalocyanines, and zinc phthalocyanines.

Radiotherapeutics such as ionizing radiation, (e.g., x-radiation, $\gamma$-radiation, visible radiation, ultraviolet light, radiation, infrared radiation, microwave radiation). Examples of radioactive isotopes used in radiation therapy include Ra-226, Co-60, Cs-137, Ir-192 and I-125. External beam therapy is commonly delivered via a medical linear accelerator or Cobalt-60 unit. An exemplary external beam radiation therapy regimen is 1.8-2 Gy per day, administered 5 days each week for 5-7 weeks, depending on the particular clinical situation, wherein the abbreviation Gy represents a Gray which represents 1 J/kg of tissue.

Mixtures of any of the foregoing chemotherapeutic agents are also useful in the present invention.

Formulations

The compositions disclosed herein comprise a Chk1 inhibitor and a cyclodextrin. In various embodiments, the compositions can further include an anticancer agent, such as a Chk1 activator. Other additives also can be included in the compositions, for example, pharmaceutically acceptable excipients, pH-adjusting agents, such as buffers, as well as other additives. Such optional additional additives may include any single additive or combination of additives, as may be determined by a pharmacist, an attending physician, researcher, or others of ordinary skill in the relevant art for which the composition is used. Non-limiting examples of such additives include, alone or in combination or subcombination, such as one or more of an antiemetic, a cytoprotective agent, an antinecrotic, and/or an imaging agent.

As used herein, "formulation" is interchangeable with the term "composition."

In some embodiments, Chk1 inhibitor formulations can be prepared in the following manner. A stock solution of the free base form of the Chk1 inhibitor is prepared at the desired concentration in a solvent, such as water. To that solution, a second stock solution of the cyclodextrin in a solvent, such as water, is added. The resulting mixture can be sonicated to ensure complete mixing of the components. The pH of the mixture can be adjusted using known techniques, such as the addition of a buffer or other pH adjusting agent. This mixture then can be further manipulated, according to various embodiments disclosed herein, for example, adding an antiemetic agent, a cytoprotective agent, and/or the like. The mixture can additionally or alternatively be manipulated depending upon its desired route of administration and/or storage requirements. For example, the mixture can be dried (e.g., via lypohilization or spray drying), modified for injection, and the like.

The pH of a formulation of various embodiments of the invention can vary widely to suit the intended purpose, as will be appreciated by those skilled in the art. In some embodiments, an aqueous solution of the disclosed formulations has a pH of from about 2 to about 8, in other embodiments from about 3 to about 7, in other embodiments from about 4 to about 5, in other embodiments from about 3.2 to about 6.5. For formulations which are in a solid form, the pH of the formulation refers to the pH of the solid formulation when dissolved in an aqueous solution. Specific contemplated pHs of the formulations, when in an aqueous solution, include about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, and about 7.9.

In various embodiments, additional pharmaceutically acceptable ingredients, such as those described below, can be present, singly or in combination or any sub-combination. Pharmaceutically acceptable excipients include, but are not limited to, mannitol, glycine, lactose, sucrose, trehalose, dextran, hydroxyethyl starch, ficoll, gelatin, dextrose, sodium chloride, sodium sulfate, sorbitol, acetate salts, citrate salts, tartrate salts, phosphate salts, polyols (e.g., polyethylene and propylene glycols), amino acids, and surfactants such as polysorbates and bile salts.

Formulations as disclosed herein can also include a preservative. Exemplary, but nonlimiting, preservatives include benzyl alcohol, benzalkonium chloride, phenol, m-cresol, methyl p-hydroxybenzoate, benzoic acid, phenoxyethanol, methyl paraben, and propyl paraben.

Any pharmaceutically acceptable liquid, semisolid, or solid excipient known in the art that serve as pharmaceutical vehicles or media may be used. Exemplary excipients include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, $\alpha$-lactose, anhydrous lactose, cellulose, sucrose, dextrose, sorbitol, modified dextrans, gum acacia, and starch. Some commercially available excipients are Fast-Flo®, Emdex®, STA-Rx 1500®, Emcompress® and Avicell®. See, e.g., Remington's Pharmaceutical Sciences, 18th Ed. (1990, Mack Publishing Co., Easton, Pa. 18042) pages 1435-1712, incorporated by reference herein.

Pharmaceutically acceptable fillers can include, for example, lactose, microcrystalline cellulose, dicalcium phosphate, tricalcium phosphate, calcium sulfate, dextrose, mannitol, and/or sucrose.

Inorganic salts including calcium triphosphate, magnesium carbonate, and sodium chloride also may be used as fillers in the pharmaceutical compositions. Amino acids may be used, such as use in a buffer formulation of the pharmaceutical compositions.

Disintegrants may be included in solid dosage formulations of the inhibitors. Materials used as disintegrants include but are not limited to starch including the commercial disintegrant based on starch, Explotab®. Sodium starch glycolate, Amberlite®, sodium carboxymethylcellulose, ultramylopectin, sodium alginate, gelatin, orange peel, acid carboxymethyl cellulose, natural sponge, corn starch, potato starch, and bentonite may all be used as disintegrants in the pharmaceutical compositions. Other disintegrants include insoluble cationic exchange resins. Powdered gums including powdered gums such as agar, karaya or tragacanth may be used as disintegrants and as binders. Alginic acid and its sodium salt are also useful as disintegrants.

Binders may be used to hold the composition ingredients together to form a hard tablet and include materials from natural products, such as acacia, tragacanth, starch and gelatin. Others include crystalline cellulose; cellulose derivatives, such as methyl cellulose (MC), ethyl cellulose (EC) and carboxymethyl cellulose (CMC); acacia; corn starch, and/or gelatins. Polyvinyl pyrrolidone (PVP) and hydroxypropylmethyl cellulose (HPMC) can be used in alcoholic solutions to granulate the composition ingredients.

An antifriction agent may be included in the formulation to prevent sticking during the formulation process. Lubricants may be used as a layer between the therapeutic and the die wall, and these can include, but are not limited to, stearic acid including its magnesium and calcium salts, polytetrafluoroethylene (PTFE), liquid paraffin, vegetable oils, talc, and waxes. Soluble lubricants also may be used, such as sodium lauryl sulfate, magnesium lauryl sulfate, and polyethylene glycol of various molecular weights, e.g., Carbowax 4000 and 6000.

Glidants to improve the flow properties of the drug during formulation and to aid rearrangement during compression can be added. Suitable glidants include, but are not limited to, starch, talc, pyrogenic silica and hydrated silicoaluminate.

To aid dissolution of the formulation into an aqueous environment, a surfactant might be added as a wetting agent. Natural or synthetic surfactants may be used. Surfactants may include anionic detergents such as sodium lauryl sulfate, dioctyl sodium sulfosuccinate, and dioctyl sodium sulfonate. Cationic detergents, such as benzalkonium chloride and benzethonium chloride can also be used. Nonionic detergents that can be used in the pharmaceutical formulations include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose, and carboxymethyl cellulose. These surfactants could be present in the pharmaceutical compositions of the invention either alone or as a mixture in different ratios.

Controlled release formulations may be desirable. The Chk1 inhibitors and cyclodextrins can be incorporated into an inert matrix which permits release by either diffusion or leaching mechanisms, e.g., gums. Slowly degenerating matrices also may be incorporated into the pharmaceutical formulations, e.g., alginates, polysaccbarides. Another form of controlled release is a method based on the Oros therapeutic system (Alza Corp.), i.e., the drug is enclosed in a semipermeable membrane which allows water to enter and push the inhibitor compound out through a single small opening due to osmotic effects. Some enteric coatings also have a delayed release effect.

Colorants and flavoring agents also may be included in the pharmaceutical compositions. For example, the Chk1 inhibitors and cyclodextrins may be formulated (such as by liposome or microsphere encapsulation), then further contained within an edible product, such as a refrigerated beverage containing colorants and flavoring agents.

A present composition also can be administered as a film coated tablet. Nonenteric materials for use in coating the pharmaceutical compositions include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, povidone and polyethylene glycols. Enteric materials for use in coating the pharmaceutical compositions include esters of phthalic acid. A mix of materials can be used to provide the optimum film coating. Film coating manufacturing may be carried out in a pan coater, in a fluidized bed, or by compression coating.

The compositions can be in solid, semi-solid, or liquid forms, or can be a dried powder, such as a lyophilized form. The pharmaceutical compositions can be packaged in forms convenient for delivery, including, for example, capsules, sachets, cachets, gelatins, papers, tablets, capsules, ointments, granules, solutions, inhalants, aerosols, suppositories, pellets, pills, troches, lozenges or other forms known in the art. The type of packaging generally will depend on the desired route of administration. Implantable sustained release formulations also are contemplated, as are transdermal formulations.

In various embodiments, the compositions disclosed herein can further include one or more antiemetic agents. Contemplated antiemetic agents include, but are not limited to, dopamine antagonists, phenothiazine, $5HT_3$ antagonists, and antihistamines. Specific antiemetic agents include, but are not limited to, metoclopramide, domperidone, prochlorperazine, trifluoroperazine, promethazine, dimenhydrinate, cinnarizine, cyclizine, ondansetron, granisetron, trimethobenzamide, dolasetron, aprepitant, scopolamine, Dramamine, and tropisetron.

In various embodiments, the compositions disclosed herein can further include one or more cytoprotective agents. Non-limiting examples of cytoprotective agents include chemotherapy and radiotherapy protective agents and/or antinecrotic agents. Such agents include, but are not limited to, Zinecard® (dexrazoxane for injection, Pharmacia, Inc., Dublin, Ohio, USA.), Mesna® (sodium 2-sulfanylethanesulfonate, Baxter, Inc., Deerfield, Ill., USA), and Amifostine® (Ethyol, Medimune Oncology, Inc., Gaithersburg, Md.). Non-limiting examples of cytoprotective agents also include one or more cyclodextrins such as those described in U.S. Pat. Nos. 5,602,112, 5,804,568, 6,048,845, 6,218,374, 6,284,747, the relevant portions of which are incorporated herein by reference.

In various embodiments, the compositions disclosed herein can further include one or more imaging agents. Contemplated imaging agents include, but are not limited to, paramagnetic, radioactive and fluorogenic ions. In alternative embodiments, the imaging agent comprises a radioactive imaging agent. Exemplary radioactive imaging agents include, but are not limited to, gamma-emitters, positron-emitters, and x-ray-emitters. Particular radioactive imaging agents include, but are not limited to, $^{43}K$, $^{52}Fe$, $^{57}Co$, $^{67}Cu$, $^{67}Ga$, $^{68}Ga$, $^{77}Br$, $^{81}Rb$, $^{81}Kr$, $^{87}Sr$, $^{99}Tc$, $^{111}In$, $^{113}In$, $^{123}I$, $^{125}I$, $^{127}Cs$, $^{129}Cs$, $^{131}I$, $^{132}I$, $^{197}Hg$, $^{203}Pb$, and $^{206}Bi$, and those based thereon. Other radioactive imaging agents known by one skilled in the art can be used as well, including barium and gadolinium.

In some embodiments, the formulations disclosed herein are substantially free of water. "Substantially free of water" means that the amount of water present in the formulation is less than an amount necessary to hydrolyze and/or adversely effect the chemical and/or physical properties of the Chk1 inhibitor, cyclodextrin, and/or other additives present in the formulation. In specific embodiments, the amount of water present in the formulation is typically less than about 5%, based upon the weight of the formulation. Also contemplated are formulations where the amount of water is less than about 4%, less than about 3%, less than about 2%, and less than about 1%. Other amounts of water in the formulations contemplated include less than about 4.9%, less than about 4.8%, less than about 4.7%, less than about 4.6%, less than about 4.5%, less than about 4.4%, less than about 4.3%, less than about 4.2%, less than about 4.1%, less than about 3.9%, less than about 3.8%, less than about 3.7%, less than about 3.6%, less than about 3.5%, less than about 3.4%, less than about 3.3%, less than about 3.2%, less than about 3.1%, less than about 2.9%, less than about 2.8%, less than about 2.7%, less than about 2.6%, less than about 2.5%, less than about 2.4%, less than about 2.3%, less than about 2.2%, less than about 2.1%, less than about 1.9%, less than about 1.8%, less than about 1.7%, less than about 1.6%, less than about 1.5%, less than about 1.4%, less than about 1.3%, less than about 1.2%, less than about 1.1%, less than about 0.9%, less than about 0.8%, less than about 0.7%, less than about 0.6%, less than about 0.5%. Specific formulations include those wherein the amount of water is less than about 1.2%.

In such embodiments where the formulations are substantially free of water, the formulations are lyophilized, spray-dried, or subjected to other such comparable methods for drying a composition as known to those of skill in the relevant art. Compositions which are substantially free of water can be reconstituted with water or other aqueous solution(s) prior to administration.

Dosage of Active Agents

Active agents (e.g., anticancer agent and Chk1 inhibitor) are employed in amounts effective to achieve their intended purpose. As used herein, a "therapeutically effective amount" means an amount effective to inhibit development of, or to alleviate the existing symptoms of, the condition of the subject being treated. "Dose-effective to inhibit" means an amount effective to inhibit or prevent the proliferation of a population of aberrantly proliferating cells, in vivo or ex vivo. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred.

Inhibition of the checkpoint kinase can measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve expressing a degree of inhibition as a function of concentration. The curve also theoretically passes through a point at which the concentration is sufficient to reduce activity of the checkpoint enzyme to a level that is 50% that of the difference between minimal and maximal enzyme activity in the assay. This concentration is defined as the Inhibitory Concentration (50%) or $IC_{50}$ value. Determination of $IC_{50}$ values preferably is made using conventional biochemical (acellular) assay techniques or cell-based assay techniques.

Comparisons of the efficacy of inhibitors often are provided with reference to comparative $IC_{50}$ values, wherein a higher $IC_{50}$ indicates that the test compound is less potent, and a lower $IC_{50}$ indicates that the compound is more potent, than a reference compound. Chk1 inhibitor compounds demonstrating $IC_{50}$ values of less than about 1000 nM, or less than about 250 nM, or less than about 100 nM, or less than about 50 nM, or less than about 20 nM, or less than about 1 nM, when measured using the dose-response assay, may be employed according to the invention.

The data obtained in such dose-response assays can be used as a factor in formulating a dosage range for use in humans. The dosage of such compounds preferably lies within a range of circulating concentrations that include the $ED_{50}$ with little or no toxicity. The dosage can vary within this range depending upon the dosage form, and the route of administration utilized.

The exact formulation, route of administration, and dosage is chosen by the individual physician in view of the patient's condition. Dosage amount and interval can be adjusted individually to provide plasma levels of the active compound that are sufficient to maintain desired therapeutic effects. In general, however, doses employed for adult human treatment typically are in the range of 0.001 mg/kg to about 1000 mg/kg per day, in a range of about 0.1 mg/kg to about 500 mg/kg per dose of Chk1 inhibitor. In some embodiments, Chk1 doses range from about 0.1 to about 50 mg/kg, about 0.5 to about 40 mg/kg, about 0.7 to about 30 mg/kg, or about 1 to about 20 mg/kg. Specific doses contemplated include sub-ranges of any of the foregoing ranges in 0.1 mg/kg increments.

In various aspects of the invention, the disclosed formulations are administered in conjunction with an anticancer agent. In specific embodiments, the therapeutically effective amount of the anticancer agent can be influenced by the simultaneous and/or sequential administration of the Chk1 inhibitor present in the composition. Therefore, in various embodiments, the therapeutically effective amount of the anticancer agent for administration in conjunction with a Chk1 inhibitor is less than the therapeutically effective amount of the same anticancer agent in the absence of a Chk1 inhibitor. Such a determination of the appropriate therapeutically effective dosage of anticancer agent and/or Chk1 inhibitor is within the scope of knowledge of the treating physician, based upon an individual patient's specific disease, medical history, and other such factors.

Scheduling of Administration

In some embodiments, as indicated above, the at least one antiproliferative (e.g., anticancer) agent is administered before, after, or at the same time as a composition according to an embodiment of the invention. The frequency of dosing, duration of dosing, and dose of the antiproliferative agent and Chk1 inhibitor present in various embodiments of the present invention may each be independently varied to accomplish their intended purposes, as will be appreciated by those of ordinary skill in the art.

In some embodiments, the antiproliferative agent comprises a Chk1 activator. In some embodiments, Chk1 activator is contacted with a population of aberrantly proliferating cells in an amount and for a time and/or frequency sufficient to substantially synchronize cell cycle arrest at the target phase for the type of Chk1 activator used, prior to contacting the population with Chk1 inhibitor. Such methods are generally disclosed in WO 05/27907, which is incorporated herein in its entirety by reference. In such embodiments, the cell population may be contacted with Chk1 inhibitor by administration of a formulation according to various embodiments of the present invention.

In some embodiments, the population of aberrantly proliferating cells will undergo optimal synchronization prior to contacting the population with Chk1 inhibitor. For optimal synchronization, a maximum percentage of cells in the population to are allowed to "pile up" or arrest in the target phase for the activator used, with a minimum percentage having progressed into mitosis. However, those skilled in the art will appreciate that lesser degrees of cell cycle synchronization prior to contact with the Chk1 inhibitor will provide some benefit. Thus, "substantial synchronization" includes any degree of synchronization of cell cycle arrest, including optimal, that results in a cytotoxic effect greater than that seen without use of Chk1 inhibitor, or greater than that seen with co-administration of Chk1 activator and inhibitor, or greater than that seen when the cells are contacted with Chk1 inhibitor prior to Chk1 activator. The degree of cell cycle arrest corresponding to or exceeding these references qualifies as "substantial synchronization."

Treatment with a disclosed composition may follow at least about a 10% increase in the number of aberrantly proliferating cells in the target phase of the Chk1 activator used; optionally at least about 20%, at least about 50%, at least about 100%; at least about 150%; at least about 200%; at least about 250%; at least about 300%; at least about 350%; at least about 400% increase, at least about 450%/o, or at least about 500%, as compared to the number of aberrantly proliferating cells present in such phase in the absence of a Chk1 activator. These ranges are merely exemplary, however, and are dependent upon cell type, the particular Chk1 activator used, and other factors readily discernable to those skilled in the art. For example, the skilled artisan will appreciate that the maximum percent increase for any particular cell sample population of aberrantly proliferating cells will be limited by various factors, including percentage of cells present in the target phase of the population prior to Chk1 activator contact.

As indicated above, upon achieving substantial synchronization of cell cycle arrest in the cell population, the cell population can be contacted with a Chk1 inhibitor using a formulation of the present invention in an amount and for a time sufficient to substantially abrogate the cell cycle arrest. The term "substantially abrogate" is used to indicate that complete abrogation of all arrested cells may not be necessary for efficacy. Those skilled in the art will appreciate that a sufficient degree of cell cycle checkpoint abrogation may be achieved to disrupt cell cycle checkpoint mechanisms and allow cells to pass to a subsequent phase in the cell cycle with unrepaired DNA damage sufficient to cause cell death or otherwise slow or stop aberrant cell proliferation.

Those skilled in the art will appreciate how to convert information concerning cell cycle synchronization and abrogation to practical use in the clinic or laboratory. For example, for any given cell line, Chk1 activator, and Chk1 inhibitor, the dose, frequency of dose, and period over which to administer each dose to achieve substantial cell cycle synchronization and substantial abrogation, respectively, may be measured ex vivo. Ex vivo measurements then may be applied to the clinic as a practical surrogate for direct measurement of the percentage of cells in various phases of the cell cycle.

In determining such measurements, those skilled in the art will appreciate that the frequency and duration of Chk1 activator contact with the cell population may, as indicated above, be influenced by the cell type exhibiting unwanted cell proliferation. Like most cells, aberrantly proliferating cells do not cycle at a universal rate. Some types proliferate faster than others, i.e., have a faster doubling time. Thus, for example, treatment of a tumor cell type with a fast doubling time (e.g., pancreatic cancer or melanoma) may require shorter treatment with Chk1 activator to substantially synchronize cell cycle arrest, while treatment of a tumor with a slower doubling time (e.g., some colon, breast or prostate tumors) would require longer contact with Chk1 activator, all other things being equal, to induce substantially synchronous cell cycle arrest.

Times effective to allow substantial cell cycle synchronization by the Chk1 activator may vary from a few minutes up to 96 hours or more. In some embodiments, it may be preferable or desirable to administer a Chk1 activator for up to several weeks or more, as determined by the attending physician or technician. Thus, a Chk1 activator can contact the cell population for up to about 30 minutes, up to about 1 hour, up to about 2 hours, up to about 3 hours, up to about 4 hours, up to about 6 hours, up to about 12 hours, up to about 18 hours, up to about 24 hours, up to about 48 hours, up to about 72 hours or up to about 96 hours or more. Those skilled in the art will appreciate that the ranges of time expressed herein are merely exemplary; ranges and sub-ranges within those expressed may be used.

Contact of the cell population with the Chk1 activator may occur in single doses or over a plurality of doses, according to methods well known in the art for the particular Chk1 activator or activators used. For example, the Chk1 activator may be given at a frequency of: 4 doses delivered as one dose per day at 4-day intervals (q4dx4); 4 doses delivered as one dose per day at 3-day intervals (q3dx4); 1 dose delivered per day at 5-day intervals (qdx5); one dose per week for 3 weeks (qwk3); 5 daily doses, with two days rest, and another 5 daily doses (5/2/5); or, any dose regimen determined to be appropriate for circumstance. Some time may optionally be allowed to lapse between the last dose of Chk1 activator to achieve substantial synchronization of cell cycle arrest prior to contact with the first dose of Chk1 inhibitor as necessary. Similar regimens may be used when Chk1 activator is chemotherapeutic or radiotherapeutic. Additional radiotherapeutic doses are well known to those of ordinary skill in the art.

Contact of the cell population with a composition of the present invention may likewise occur at any dose and time sufficient to achieve substantial abrogation of the cell cycle checkpoint. Typically, though not necessarily, such times include up to about 72 to about 96 hours, depending upon various factors such as those discussed above. In some embodiments, it may be desirable or necessary to administer a present composition over a period of up to about several weeks or more, as determined by the attending physician or technician. Thus, the composition typically can be administered for up to about 1 hour, up to about 2 hours, up to about 3 hours, up to about 4 hours, up to about 6 hours, up to about 12 hours, up to about 18 hours, up to about 24 hours, up to about 48 hours, or up to about 72 hours. Those skilled in the art will appreciate that the ranges of time expressed herein are merely exemplary; ranges and sub-ranges within those expressed may be used A present composition can be administered over a plurality of doses. For example, a present composition can be given at a frequency of: 4 doses delivered as one dose per day at 4-day intervals (q4dx4); 4 doses delivered as one dose per day at 3-day intervals (q3dx4); 1 dose delivered per day at 5-day intervals (qdx5); one dose per week for 3 weeks (qwk3); 5 daily doses, with two days rest, and another 5 daily doses (5/2/5); or, any dose regimen pre-determined to be appropriate for the circumstance.

Routes of Administration

In various aspects, the compositions disclosed herein can be administered dermally, subcutaneously, intramuscularly, intra-articularly, pulmonally, buccally, sublingually, nasally, via inhalation, percutaneously, vaginally, orally, parenterally, rectally, intravenously, topically, intradermally, ophthalmically, and/or intraperitonealy. The route of administration can be chosen by the treating physician, based upon the patient's condition and disease to be treated.

Parenteral administration includes, but is not limited to intravenous, intra-arterial, intraperitoneal, subcutaneous, intramuscular, intrathecal, and intra-articular. Parenteral administration also can be accomplished using a high-pressure technique, like POWDERJECT™.

For oral or buccal administration, the composition can be in the form of tablets or lozenges formulated in conventional manner. For example, tablets and capsules for oral administration can contain conventional excipients, such as binding agents (for example, syrup, acacia, gelatin, sorbitol, tragacanth, mucilage of starch, or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol or silica), disintegrants (for example, potato starch or sodium starch glycolate), or wetting agents (for example, sodium lauryl sulfate). The tablets can be coated according to methods well known in the art.

Alternatively, a composition of the present invention can be incorporated into oral liquid preparations such as aqueous or oily suspensions, solutions, emulsions, syrups, or elixirs, for example. Moreover, the compositions can be a dry product for constitution with water or other suitable vehicle before use. Such liquid preparations can contain conventional additives, for example suspending agents, such as sorbitol syrup, methyl cellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

The compositions also can be formulated into suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the compositions can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compositions of the invention can be formulated with suitable polymeric or hydrophobic materials (e.g., an emulsion in an acceptable oil), ion exchange resins, or as sparingly soluble derivatives (e.g., a sparingly soluble salt).

Cancers and Other Diseases

Use of the disclosed compositions is indicated in a treatment of any condition involving aberrant cell proliferation, including cancerous and non-cancerous cell proliferation. In one aspect, treatment may be of any condition responsive to agents that activate cell cycle arrest or are responsive to inhibitors of cell cycle checkpoint proteins.

Cancers include tumors or neoplasms derived from growths of tissue cells wherein multiplication of cells is uncontrolled and progressive. Some such neoplasms are benign, but others are termed "malignant," and can lead to death of the organism. Malignant neoplasms are distinguished from benign growths in that, in addition to exhibiting aggressive cellular proliferation, the malignant neoplasms can invade surrounding tissues and metastasize. Moreover, malignant neoplasms are characterized by showing a greater loss of differentiation (greater "dedifferentiation") and organization relative to one another and surrounding tissues. This property is called "anaplasia."

Cancers treatable by the present invention include solid tumors such as carcinomas and sarcomas. Carcinomas derive from epithelial cells which infiltrate (i.e., invade) surrounding tissues and give rise to metastases. Adenocarcinomas are carcinomas derived from glandular tissue, or from tissues that form recognizable glandular structures. Sarcomas are tumors whose cells are embedded in a fibrillar or homogeneous substance, like embryonic connective tissue. The invention also enables treatment of cancers of the myeloid or lymphoid systems, including leukemias, lymphomas, and other cancers that typically are not present as a tumor mass, but are distributed in the vascular or lymphoreticular systems.

Further cancers include, but are not limited to, myxoid and round cell carcinomas, human soft tissue sarcomas including Ewing's sarcoma, cancer metastases including lymphatic metastases, squamous cell carcinomas particularly of the head and neck, esophageal squamous cell carcinomas, oral carcinomas, blood cell malignancies, including multiple myelomas, leukemias, including acute lymphocytic leukemias, acute nonlymphocytic leukemias, chronic lymphocytic leukemias, chronic myelocytic leukemias, and hairy cell leukemias, effusion lymphomas (body cavity based lymphomas), thymic lymphoma lung cancers (including small cell carcinomas of the lungs, cutaneous T cell lymphomas, Hodgkin's lymphomas, non-Hodgkin's lymphomas, cancers of the adrenal cortex, ACTH-producing tumors, non-small cell lung cancers, breast cancers, including small cell carcinomas and ductal carcinomas), gastro-intestinal cancers (including stomach cancers, colon cancers, colorectal cancers, and polyps associated with colorectal neoplasias), pancreatic cancers, liver cancers, urological cancers (including bladder cancers, such as primary superficial bladder tumors, invasive transitional cell carcinomas of the bladder, and muscle-invasive bladder cancers), prostate cancers, malignancies of the female genital tract (including ovarian carcinomas, primary peritoneal epithelial neoplasms, cervical carcinomas, uterine endometrial cancers, vaginal cancers, cancers of the vulva, uterine cancers and solid tumors in the ovarian follicle), malignancies of the male genital tract (including testicular cancers and penile cancers), kidney cancers (including renal cell carcinomas), brain cancers (including intrinsic brain tumors, neuroblastomas, astrocytomas, gliomas, and metastatic tumor cell invasions in the central nervous system), bone cancers (including osteomas and osteosarcomas), skin cancers (including malignant melanomas, tumor progressions of human skin keratinocytes, basal cell carcinomas, and squamous cell cancers), thyroid cancers, retinoblastomas, peritoneal effusions, malignant pleural effusions, mesotheliomas, Wilms's tumors, gall bladder cancers, trophoblastic neoplasms, hemangiopericytomas, and Kaposi's sarcomas.

As non-limiting examples, the methods disclosed herein can utilize the following exemplary anticancer agents (alone or in combination with other active agents):

Gemcitabine for the treatment of proliferative disorders including pancreatic cancer (e.g., locally advanced (nonresectable state II or stage III) or metastatic (stage IV) adenocarcinoma of the pancreas); gemcitabine for the first-line treatment and for patients previously treated with a 5-FU regimen; gemcitabine in combination with platinum coordination complexes (e.g., cisplatin) for the treatment non-small cell lung cancer (e.g., inoperable, locally advanced (stage IIIA or IIIIB) or metastatic (stage IV) non-small cell lung cancer);

Pemetrexed for the treatment of proliferative disorders including non-small lung cell carcinomas, solid tumors, malignant mesothelioma, urothelioma, cervical cancer, recurrent endometrial cancer, peritoneal cancer, pleural mesothelioma, gall bladder cancer, breast cancer, and colorectal cancer;

Topotecan for the treatment of proliferative disorders including meningeal cancers, cervical cancer, ovarian cancer, epithelial cancer, esophageal cancer, fallopian tube cancer, primary peritoneal cancer, small cell lung cell cancer, prostate cancer, neuroblastomas, gliomas, solid tumors, acute myeloid leukemia, chromic myelogenous leukemia, advanced myelodysplastic syndromes, and rhabdomyosarcoma;

Irinotecan for the treatment of proliferative disorders including colorectal cancer, glioblastoma multiforme, solid tumors, breast cancer, penile cancer, liver cancer, metastatic gastric carcinoma, gastroesophageal junction adenocarcinoma, small bowel adenocarcinoma, rhabdomyosarcoma, urothelium cancer, stomach cancer, bladder cancer, kidney cancer, small cell lung cancer, pancreatic cancer, head and neck cancer, glioma, sarcoma, metastatic carcinoma of the colon or rectum;

Chlorambucil for the treatment of proliferative disorders including chronic lymphocytic leukemia, Hodgkin's lymphoma; non-Hodgkin's lymphoma, follicular lymphoma, chronic lymphocytic cancer;

Platinum coordination complexes, e.g., cisplatin, for the treatment of proliferative disorders including testicular cancer, ovarian cancer, bladder cancer, head and neck cancer, esophageal cancer, small cell and non-small cell lung cancer, non-Hodgkin's lymphoma, trophoblastic neoplasms; adrenal cortical cancer, anal cancer, bile duct cancer, bladder cancer, bone cancer, cervical cancer, endometrial cancer, gall bladder cancer, gastrointestinal carcinoid tumors, laryngeal cancer, hypopharyngeal cancer, liver cancer, lung cancer, small cell lung cancer, malignant mesothelioma, nasal cavity cancer, paranasal cancer, nasopharyngeal cancer, neuroblastoma, oral cavity cancer, oropharyngeal cancer, osteosarcoma, ovarian cancer, germ cell tumors of the ovary, pancreatic cancer, penile cancer, retinoblastoma, salivary gland cancer sarcoma, melanoma, stomach cancer, testicular cancer, thymus cancer, uterine sarcoma, vulvar cancer;

Carboplatin for the treatment of proliferative disorders including ovarian cancer, germ cell tumors, head and neck cancer, small cell and non-small cell lung cancer, bladder cancer, relapsed and refractory acute leukemia, endometrial cancer;

Camptothecin for the treatment of proliferative disorders including stomach cancer, gastroesophageal junction cancer, soft tissue sarcoma, malignant glioma;

Etoposide for the treatment of proliferative disorders including small cell and other lung cancers, gastric cancer, germ cell tumors, adrenal cortical cancer, bone cancer, gastrointestinal carcinoid tumors, gestational trophoblastic disease, Hodgkin's disease, acute lymphocytic cancer, childhood leukemia, small cell lung cancer, lung carcinoid tumor, neuroblastoma, osteosarcoma, ovarian cancer, germ cell tumors of the ovary, prostate cancer, retinoblastoma, stomach cancer, testicular cancer, Wilms's Tumor;

Ara-C for the treatment of proliferative disorders including acute myeloid leukemia, high-risk myelodysplastic syndrome, CML, lymphoma, solid tumor, chronic lymphocytic leukemia, acute lymphocytic leukemia, acute non-lymphocytic leukemia, chronic myelocytic leukemia, precursor T-lymphoblastic lymphoma/leukemia, Burkitt's lymphoma;

Aphidocolin for ex vivo studies of proliferative disorders including breast cancer and acute myeloid leukemia;

Fludarabine for the treatment of proliferative disorders including chronic lymphocytic leukemia, follicular lymphoma, metastatic melanoma, renal cell carcinoma, acute myeloid leukemia, acute lymphoblastic leukemia, non-Hodgkin's lymphoma, breast cancer, hairy cell leukemia, multiple myeloma, cervical cancer, vaginal cancer, leukemia, childhood leukemia, chronic granulomatous disease, mastocytosis, kidney cancer, urinary tract cancer, skin tumors, bladder cancer, basal cell carcinoma, adrenal carcinoma, esophageal and gastric cancer, hepatocellular cancer, ovarian cancer, B-cell leukemia, chronic lymphocytic leukemia, follicular lymphoma; and Methotrexate for the treatment of proliferative disorders including gestational choriocarcinoma, chorioadenoma, destruens and hydatidiform moles, acute lymphocytic leukemia, meningeal leukemia, breast cancer, epidermoid cancers of the head and neck, advanced mycosis fungoides (cutaneous T-cell lymphoma), lung cancer (especially squamous cell and small cell types), non-Hodgkin's lymphomas; bladder cancer, bone cancer, breast cancer, esophageal cancer, gestational trophoblastic disease, laryngeal and hypopharyngeal cancer, acute lymphocytic leukemia, acute myeloid leukemia, small cell lung cancer, Burkitt's lymphoma, precursor T-lymphoblastic mesothelioma, nasal cavity and paranasal cancer, nasopharyngeal cancer, oral cavity and oropharyngeal cancer, osteosarcoma, penile cancer, salivary gland cancer, and stomach cancer.

The compositions disclosed herein also can be used to treat conditions involving non-cancerous aberrantly proliferating cells. Such conditions include, but are not limited to, atherosclerosis, restenosis, vasculitis, nephritis, retinopathy, renal disease, proliferative skin disorders, psoriasis, keloid scarring, actinic keratosis, Stevens-Johnson Syndrome, rheumatoid arthritis (RA), systemic-onset juvenile chronic arthritis (JCA), osteoporosis, systemic lupus (SLE) erythematosus, hyperproliferative diseases of the eye including epithelial down growth; proliferative vitreoretinopathy (PVR); diabetic retinopathy, hemangio-proliferative diseases, ichthyosis, or papillomas.

Non-cancerous conditions treatable by the present compositions can also include a variety of inflammation and inflammatory diseases, conditions, or disorders. Examples of such indications include, but are not limited to, rheumatoid arthritis, psoriasis, vitiligo, Wegener's granulomatosis, and SLE. Treatment of arthritis, Wegener's granulomatosis, and SLE often involves the use of immunosuppressive therapies, such as ionizing radiation, methotrexate, and cyclophosphamide. Psoriasis and vitiligo commonly are treated with ultraviolet radiation (UW) in combination with a psoralen. Such treatments typically induce, either directly or indirectly, DNA damage. Inhibition of Chk1 activity within the offending immune cells renders the cells more sensitive to control by these standard treatments. In general, Chk1 inhibitors useful in the invention may optionally be used to potentiate control of inflammatory disease cells when administered alone or in combination with immunosuppressive drugs.

Animal models of some of the foregoing cancerous and non-cancerous conditions treatable by the disclosed compositions include for example: athymic nude mice prepared with viable cancer cells from the HL60 cell line (human non-small cell lung cancer), athymic nude mice injected with Panc-01 human tumor cells (human pancreatic cancer), athymic nude mice injected with A375 human tumor cells (human melanoma), athymic nude mice injected with SKMES lung cancer cells (human lung cancer), athymic nude mice injected with SKOV-3.ip. ovarian carcinoma cells (human ovarian cancer), athymic nude mice injected with MDA-MB-361 breast cancer cells (human breast cancer), rats injected with 137-62 cells (breast cancer), and c56BL/Ka mice (cpdm/cpdm) (human psoriasis) (Gijbels et al., *Exp. Dermatol.*, 9:351 (2000)).

Kits

Kits comprising the present compositions also are contemplated. A kit can comprise a dosage form of a disclosed composition in a first container and a package insert containing instructions for use of the composition in treatment of a medical condition. Conditions indicated on the label can include treatment of disorders involving aberrantly proliferating cells, such as cancers and non-cancerous disorders like psoriasis, renal disease, and systemic lupus erythematosus. In some embodiments, the kits further comprise a therapeutic agent useful in the treatment of aberrantly proliferating cells. In some embodiments, the therapeutic agent comprises an anticancer agent. In specific embodiments, the anticancer agent is present in the first container as a component of the inventive composition, while in other specific embodiments, the anticancer agent is packaged in a second container. The package insert contains instructions on the use of the packaged composition or compositions in the treatment of a medical condition, like a cancer.

EXAMPLES

The following examples are provided to illustrate the invention, but are not intended to limit the scope thereof. In vitro hemolysis studies describe the decreased toxicity of compositions comprising at least one Chk1 inhibitor and at least one cyclodextrin compared to Chk1 inhibitor compositions in the absence of a cyclodextrin. Solubility studies demonstrate the increased amounts of Chk1 inhibitor solubilized in compositions comprising a cyclodextrin compared to compositions free of a cyclodextrin. For the studies described below, two different disubstituted urea Chk1 inhibitor compounds of formula (X) were used, which will be referred to as "Chk1 inhibitor A" and "Chk1 inhibitor B," respectively.

In Vitro Hemolysis Studies

The hemolytic potential of Chk1 inhibitor A of formula (X) was determined in various formulation excipients when spiked into rat and human blood. These in vitro experiments were based upon a modified method reported by Krzyzaniak et al., *J. Pharm. Sciences*, 86:1215 (1997). Fresh whole blood from normal human donors or Sprague-Dawley rats was collected into sodium heparin and an aliquot was centrifuged to verify a hemolysis-free sample. Negative controls consisted of normal saline (0.9%) or excipient only. A red blood cell (RBC) lysis buffer (10 mM $KHCO_3$, 150 mM $NH_4Cl$, 0.1 mM EDTA, pH 7.5) was used as a positive control. Aliquots of 0.02 mL of control or formulated test sample were mixed with 0.98 mL of blood to achieve varying final concentrations of the Chk1 inhibitor compound (10-1000 μg/mL). Alternatively, other blood/test article volume ratios also were tested using 0.1 mL of test sample with 0.9 mL of whole blood. Samples were incubated at 25° C. for 3 minutes and then centrifuged at 3000 rpm for 10 min. The plasma supernatant was collected for a qualitative determination of hemolysis, based on visual analysis using a rated score as follows: 0-no hemolysis; 1-trace hemolysis; 2-slight to moderate hemolysis; 3-marked hemolysis; 4-gross hemolysis. For some samples, quantitative analysis was performed by measuring absorption of hemoglobin in the plasma supernatant at 540 nm by UV spectrometry to calculate percent hemolysis. Osmolality readings also were measured on the test samples from the assays. The osmolality measurements of all test solutions in these experiments were interpreted as within a normal range. Therefore, an osmolality-induced imbalance of the formulated solutions did not contribute to the experimental results. Results for the assay in various formulations are reported in Table II, below. As seen in Table II, the formulation containing Captisol and free base of Chk1 inhibitor A was able to better protect the erythrocytes from hemolysis at concentrations of 100 μg/mL than the corresponding composition having the monomesylate salt of the Chk1 inhibitor.

For the in vitro hemolysis studies, two Chk1 inhibitor formulations were prepared for analyses. The first was a stock formulation of the free base form of Chk1 inhibitor A, which was prepared at a concentration of 50 mg/mL in 16.67% (w/v) Captisol in sterile water. To prepare the stock formulation, the appropriate amount of the free base form of Chk1 inhibitor A was weighed and placed in an appropriate sized container. The formulation was brought up to 90% of the desired volume with a 16.67% (w/v) Captisol in sterile water solution. The solution then was sonicated to break up any aggregates of the Chk1 inhibitor. While stirring the solution, a calibrated pH meter was used to measure the pH. The pH was gradually adjusted to 4.5±0.1 with HCl (hydrochloric acid). Finally, the formulation was brought up to final volume with the 16.67% (w/v) Captisol in sterile water solution to achieve the 50 mg/mL target concentration of Chk1 inhibitor A. To prepare all other Chk1 inhibitor A solutions, the 50 mg/mL stock solution was diluted to the desired final concentration with 5% Dextrose Injection USP (D5W). This procedure was implemented to maintain a constant ratio of test compound to Captisol throughout all of the formulations. A second formulation was prepared with the monomesylate salt of Chk1 inhibitor A in 5% dextrose. For this formulation, the appropriate amount of the monomesylate salt of Chk1 inhibitor A (adjusted for increased formula weight (FW) due to the addition of the mesylate ion) was weighed and placed in an appropriate sized container. The formulation was brought up to the desired final volume with 5% D5W to yield a 50 mg/mL Chk1 inhibitor A monomesylate salt stock solution. The solution then was sonicated to break up any Chk1 inhibitor aggregates. While stirring the solution, a calibrated pH meter was used to measure the pH. The pH was within the desired range of 4.5±0.1 and therefore did not require adjustment. To prepare all of the other Chk1 inhibitor A monomesylate salt solutions, the 50 mg/mL stock solution was diluted to the desired final concentration with 5% D5W.

TABLE II

| Control or Test Sample | Chk1 inhibitor (μg/mL) | Hemolysis scoring | | | |
|---|---|---|---|---|---|
| | | rat | Human A | Human B | Human C |
| RBC lysis buffer | NA | 4 | 4 | 4 | 4 |
| 0.9% NaCl | NA | 0 | 0 | 0 | 0 |
| Mesylate salt in 5% dextrose | NA | 0 | 0 | 0 | 0 |
| 16.67% Captisol | NA | 0 | 0 | 0 | 0 |
| Free base of Chk1 inhibitor A formulated in 16.67% Captisol | 1000 | 3 | 3 | NA | 2 |
| Free base of Chk1 inhibitor A formulated in 1.67% Captisol | 100 | 1 | 0 | 0 | 0 |
| Free base of Chk1 inhibitor A formulated in 0.17% Captisol | 10 | 0 | 0 | 0 | 0 |
| monomesylate salt of Chk1 inhibitor A formulated in 5% dextrose | 1000 | 3 | 3 | 3 | 3 |
| | 100 | 2 | 2 | 2 | 0 |
| | 10 | 0 | 0 | 0 | 0 |

In Vivo Hemolysis Studies

In vivo pharmacokinetic studies were performed in Sprague-Dawley rats for both the Chk1 inhibitor A and Chk1 inhibitor B of formula (X). A single 5 mg/kg intravenous bolus dose was administered at 1 mL/kg to at least three rats. Both Chk1 inhibitors A and B were administered in the following formulations: (1) 2.5 mM sodium acetate and 5% dextrose; (2) 30-50% polyethylene glycol 400; or (3) 10% Captisol. The rats then were observed for adverse side effects. The results are summarized in Table III, below. Adverse reactions were defined as labored breathing immediately post dosing, hemolyzed plasma samples, and bloody-colored urine immediately post dosing, mildly persisting for up to one hour post dosing.

The formulations for the in vivo pharmacokinetic studies were prepared as follows.

(1) For the Chk1 inhibitor A monomesylate salt in 2.5 mM sodium acetate and 5% dextrose, the appropriate amount of monomesylate salt form (adjusted for FW) was weighed and placed in an appropriate sized container. The appropriate volume of 2.5 mM sodium acetate and 5% dextrose was added to the formulation to achieve the final target concentration. The solution then was sonicated to break up any Chk1 inhibitor aggregates. While stirring the solution, a calibrated pH meter was used to measure the pH. The pH was within the desired range of 4.2±0.3 and therefore did not require adjustment.

For the Chk1 inhibitor B free base in 2.5 mM sodium acetate and 5% dextrose, the appropriate amount of Chk1 inhibitor free base was weighed out and placed in an appropriate sized container. An in-situ salt of the compound was made by the addition of 1.1 molar equivalent of hydrochloric acid to the compound. The compound and acid were vortexed in order to uniformly "wet" the compound. The formulation was brought up to 90% of the desired volume with 2.5 mM sodium acetate and 5% dextrose. The solution then was sonicated to break up any Chk1 inhibitor aggregates. While stirring the solution, a calibrated pH meter was used to measure the pH. The pH was gradually adjusted to 4.2±0.3 with NaOH (sodium hydroxide). Finally, the formulation was brought up to final volume with 2.5 mM sodium acetate and 5% Dextrose.

(2) For the Chk1 inhibitor A in 50% polyethylene glycol 400 and the Chk1 inhibitor B in 30%/o polyethylene glycol 400, the appropriate amount of Chk1 inhibitor free base was weighed and placed in an appropriate sized container. The appropriate volume of 50% polyethylene glycol 400 in water for injection or 30% polyethylene glycol 400 in water for injection, respectively, was added to the formulation to achieve the final target concentration. The formulations were sonicated for 5 minutes, then placed on a wrist action shaker overnight to facilitate complete dissolution of the test article.

(3) For the Chk1 inhibitor A in 10% Captisol and the Chk1 inhibitor B in 10% Captisol, the appropriate amount of the Chk1 inhibitor free base was weighed and placed in an appropriate sized container, respectively. Each formulation was brought up to 90% of the desired volume with a 10% (w/v) Captisol in sterile water solution. The solutions were then sonicated to break up any Chk1 inhibitor aggregates. While stirring the solutions, a calibrated pH meter was used to measure the pH. The pH was gradually adjusted to 4.2±0.3 with HCl. Finally, the formulation was brought up to final volume with the 10% (w/v) Captisol in sterile water solution to yield the desired target concentration of each Chk1 inhibitor.

TABLE III

|  | 2.5 mM sodium acetate, 5% dextrose | PEG400 (30-50%) | 10% Captisol |
|---|---|---|---|
| Chk1 inhibitor A-free base | No data | Normal | Normal |
| Chk1 inhibitor A-monomesylate salt (5% dextrose only) | Adverse reactions | No data | No data |
| Chk1 inhibitor B | Adverse reactions | Slight reaction (labored breathing only; no hemolysis or bloody urine) | Slight reaction (labored breathing only; no hemolysis or bloody urine) |

Solubility Studies

The equilibrium solubility of Chk1 inhibitor A as its free base is low (2.6 mg/mL of water, pH 6, 25° C.). The following studies were made in order to increase solubility via addition of cosolvents and surfactants, adjustment of the pH, and complexation with cyclodextrins. The solvents selected are relevant for clinical dosing via an intravenous route.

Solubility was determined by placing an excess of Chk1 inhibitor A in a vial with the solvent/co-solvent. The vial was agitated at constant temperature for approximately 24 hours. The drug suspensions were then filtered or centrifuged. Appropriate volumes of the sample solutions were analyzed by HPLC. Table IV, below, shows the solubilities of various solvent/co-solvent combinations of Chk1 inhibitor A at 25° C., and Table V shows the solubilities in the presence of cyclodextrin.

TABLE IV

| Solvent | Solubility (mg/mL) |
|---|---|
| Water, pH 6 | 2.6 |
| 10% ethanol | 2.1 |
| 10% Cremophor ® EL | 4.1 |
| 30% PEG 400/0.9% NaCl | 6.6 |
| 2.5% glycerol | 3.0 |
| 20% propylene glycol | 3.6 |
| 20% PEG 400/10% propylene glycol | 7.0 |
| 3% dimethylacetamide | 3.1 |
| 0.5% polysorbate 80 | 4.1 |
| 0.5% Pluronic F68/0.9% NaCl | 1.0 |
| 2.5 mM sodium acetate, pH 5/5% dextrose | 3.2 |

TABLE V

| Cyclodextrin | Cyclodextrin concentration (% w/v) | Solubility (mg/mL) |
|---|---|---|
| Hydroxypropyl-β-cyclodextrin, pH 6.0 | 10 | 18.6 |
| Captisol, pH 4.0 | 10 | ≧74.0 |
| Captisol, (pH range 6.47 to 6.70) | 2.5 | 4.6 |
|  | 5.0 | 7.4 |
|  | 10 | 14.6 |
|  | 20 | 29.6 |
|  | 40 | 58.2 |
| Captisol, pH 7.6 | 1 | 0.6 |
|  | 3 | 1.4 |
|  | 5 | 2.0 |
| Captisol, pH 8.3 | 3 | 0.5 |
|  | 5 | 0.7 |

Improvements in the solubility of Chk1 inhibitor A were achieved by the addition of clinically relevant solvents for dosing via an intravenous route. Ionization of the compound through adjustment of pH also improved the solubility of Chk1 inhibitor A. Ten-fold increases in solubility were achieved by the addition of cyclodextrins to the solution. Solubilization with cyclodextrins was enhanced by lowering pH.

Stability Studies

Two solution formulations of Chk1 inhibitor A were manufactured and tested for stability. One formulation contained Chk1 inhibitor A as its free base in 16.66% Captisol pH 4.5 (Table VI). The other formulation contained the mesylate salt of Chk1 inhibitor A in 5% dextrose, pH 4.5 (Table VII). Both formulations contained 50 mg/mL of the Chk1 inhibitor. The formulations were packaged in 20 mL borosilicate glass vials with a 20 mm FLUROTEC® stopper, aluminum seal and flip-off lid.

Each formulation was stored at 25° C./60% relative humidity (RH) and 40° C./75% RH and assessed for stability of appearance, chiral purity, assay and related substances, osmolality, pH, and particulates. The total related substances from high pressure liquid chromatography (HPLC) data for vials stored upright in the stability study with and without Captisol are given in Tables VIII and IX, respectively.

Solutions of Chk1 inhibitor A in Captisol had improved chemical stability compared to solutions of the mesylate salt of Chk1 inhibitor A in the absence of Captisol when stored at 40° C./75% RH. Degradation of Chk1 inhibitor A was found to be accelerated by moisture and heat. After storage at 40° C./75% RH, the Captisol containing formulation contained 3.06 and 4.96% of related impurities after 1 and 2 months, respectively, while the non-Captisol containing formulation contained 4.41 and 7.10% at the respective timepoints.

TABLE VI

| Component | Amount per mL | Function |
| --- | --- | --- |
| Chk1 inhibitor A - free base | 50 mg | Active ingredient |
| Captisol | 16.66 mg | Solubilizer |
| HCl, NF | q.s. to pH 4.5 | pH adjustment |
| NaOH, NF | q.s. to pH 4.5 | pH adjustment |
| Water for Injection, USP | q.s. to 1 mL | Solubilizer |

TABLE VII

| Component | Amount per mL | Function |
| --- | --- | --- |
| Chk1 inhibitor A - mesylate salt | 50 mg | Active ingredient |
| Dextrose | 50 mg | Tonicity adjustment |
| HCl, NF | q.s. to pH 4.5 | pH adjustment |
| NaOH, NF | q.s. to pH 4.5 | pH adjustment |
| Water for Injection, USP | q.s. to 1 mL | Solubilizer |

TABLE VIII

| Storage conditions | T = 0 | T = 1 month | T = 2 month | T = 3 month | T = 6 month |
| --- | --- | --- | --- | --- | --- |
| 25° C./60% RH | 1.53% | 1.48% | 2.26% | 1.72% | 3.99% |
| 40° C./75% RH | 1.53% | 3.06% | 4.96% | | |

TABLE IX

| Storage conditions | T = 0 | T = 1 month | T = 2 month |
| --- | --- | --- | --- |
| 25° C./60% RH | 1.07% | 1.16% | 2.07% |
| 40° C./75% RH | 1.07% | 4.41% | 7.10% |

Numerous modifications and variations in the invention as set forth in the above illustrative examples are expected to occur to those skilled in the art. Consequently, only such limitations as appear in the appended claims should be placed on the invention.

What is claimed is:

1. A composition comprising a compound which is:

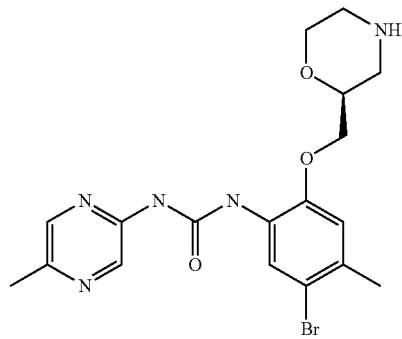 [SMILES: Cc1cnc(NC(=O)Nc2cc(Br)c(C)cc2OC[C@@H]2CNCCO2)cn1]

or a pharmaceutically acceptable salt thereof, and a specific cyclodextrin which is sulfobutylether-7-β-cyclodextrin.

2. The composition of claim 1, wherein the mole ratio of the compound to the sulfobutylether-7-β-cyclodextrin is from at least about 1:1 to at least about n:1, where n represents the total number of complexation sites of the sulfobutylether-7-β-cyclodextrin.

3. The composition of claim 1, further comprising a pH-adjusting agent.

4. The composition of claim 1, having a pH of from about 3 to about 5 in an aqueous solution.

5. The composition of claim 1, wherein the composition is substantially anhydrous.

6. The composition of claim 5, wherein water is present in an amount less than about 5% by weight.

7. The composition of claim 1, wherein the composition is lyophilized.

* * * * *

UNITED STATES PATENT AND TRADEMARK OFFICE
CERTIFICATE OF CORRECTION

| | | |
|---|---|---|
| PATENT NO. | : 8,455,471 B2 | Page 1 of 1 |
| APPLICATION NO. | : 12/442529 | |
| DATED | : June 4, 2013 | |
| INVENTOR(S) | : Wisdom et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this
Fifteenth Day of October, 2013

Teresa Stanek Rea
*Deputy Director of the United States Patent and Trademark Office*